(12) United States Patent
Yoshida et al.

(10) Patent No.: US 10,138,470 B2
(45) Date of Patent: Nov. 27, 2018

(54) MUTATED ENZYME HAVING DEHYDROGENASE ACTIVITY AND USE THEREOF

(71) Applicant: Amano Enzyme Inc., Nagoya-shi (JP)

(72) Inventors: Kazunori Yoshida, Kakamigahara (JP); Kyoichi Nishio, Kakamigahara (JP)

(73) Assignee: AMANO ENZYME INC., Nagoya-shi (JP)

( * ) Notice: Subject to any disclaimer, the term of this patent is extended or adjusted under 35 U.S.C. 154(b) by 0 days.

(21) Appl. No.: 15/522,798

(22) PCT Filed: Oct. 28, 2015

(86) PCT No.: PCT/JP2015/080466
§ 371 (c)(1),
(2) Date: Apr. 28, 2017

(87) PCT Pub. No.: WO2016/068218
PCT Pub. Date: May 6, 2016

(65) Prior Publication Data
US 2017/0327798 A1     Nov. 16, 2017

(30) Foreign Application Priority Data

Oct. 28, 2014  (JP) .................................. 2014-219593

(51) Int. Cl.
| | |
|---|---|
| *C12N 9/96* | (2006.01) |
| *C12N 9/04* | (2006.01) |
| *C12Q 1/60* | (2006.01) |
| *C12Q 1/32* | (2006.01) |
| *C12Q 1/26* | (2006.01) |

(52) U.S. Cl.
CPC ............ *C12N 9/0006* (2013.01); *C12Q 1/26* (2013.01); *C12Q 1/32* (2013.01); *C12Q 1/60* (2013.01); *C12Y 101/01* (2013.01); *C12Y 101/03006* (2013.01); *G01N 2333/904* (2013.01)

(58) Field of Classification Search
CPC .................................................. C12N 9/0006
USPC .............................................................. 435/188
See application file for complete search history.

(56) References Cited

U.S. PATENT DOCUMENTS

| | | | |
|---|---|---|---|
| 9,284,534 B2 * | 3/2016 | Kojima | .................... C12Q 1/26 |
| 2014/0255959 A1 | 9/2014 | Kojima et al. | |

FOREIGN PATENT DOCUMENTS

| | | |
|---|---|---|
| JP | 09-500528 A | 1/1997 |
| JP | 1999-002618 A | 1/1999 |
| JP | 2000-329738 A | 11/2000 |
| JP | 2001-343348 A | 12/2001 |
| JP | 2003-149247 A | 5/2003 |
| WO | 95/01098 A2 | 1/1995 |
| WO | 2013/026576 A2 | 2/2013 |

OTHER PUBLICATIONS

Kojima, K. et al., "Mutational analysis of the oxygen-binding site of cholesterol oxidase and its impact on dye-mediated dehydrogenase activity," J. Mol. Catal. B Enzym., 2013, vol. 88, p. 41-46.
International Search Report dated Dec. 22, 2015, issued for PCT/JP2015/080466.

* cited by examiner

*Primary Examiner* — Tekchand Saidha
(74) *Attorney, Agent, or Firm* — Locke Lord LLP

(57) ABSTRACT

The object is to provide a novel enzyme exhibiting cholesterol dehydrogenase activity. Provided is a mutant enzyme having an amino acid sequence of a microorganism-derived cholesterol oxidase, which is composed of: (1) an amino acid corresponding to the amino acid at the position 113 of the amino acid sequence of SEQ ID NO: 1; (2) an amino acid corresponding to the amino acid at the position 362 of the amino acid sequence of SEQ ID NO: 1; (3) an amino acid corresponding to the amino acid at the position 402 of the amino acid sequence of SEQ ID NO: 1; (4) an amino acid corresponding to the amino acid at the position 412 of the amino acid sequence of SEQ ID NO: 1; (5) an amino acid corresponding to the amino acid at the position 468 of the amino acid sequence of SEQ ID NO: 1; and others.

12 Claims, 9 Drawing Sheets

Specification includes a Sequence Listing.

```
                  ....|....| ....|.... ....|....| ....|....| ....|....| ....|....| ....|....|
                       10         20         30         40         50         60         70
CHO         ---MTAQQHL SRRRMLGMAA FGAAALAGGT TIA-APRAAA AAKSAA--DN GGYVPAVVIG TGYGAAVSAL
S.albulus   MFENQQNQHL SRRRLLGLAA LSGAAVTGLT TISAAPRAAA ADKRSPRADS GSLVPAVVIG TGYGAAVSAL
S.virginia  -----MEQHL SRRRLLGMTA LGAAALAGST TIG-APRALA ADRAD----G VAFFPAVVIG TGYGAAVSAL
S.lavendul  ---------- ----MLGLAA LGAAAMAGST TIG-ATRALA ADRAG----T PAFVPAVVIG TGYGAAVTAL
S.chattano  MFENQQNQHL SRRRLLGLAA LSGAAAVAGMT TISAAPRAAA ADKRSPKAGS GSFVPAVVIG TGYGAAVSAL
S.natalens  MFEN---QHL SRRRLLGLAA LGGAAAAGMT TITSAPHAAA ADRRSPQARS GSFVPAVVIG TGYGAAVSAL
S.avermiti  ---MIAHQPL SRRRMLGVAA LGAAALAGQT TITAAPRAAA ATATSG--SG CTFVPAVVVG TGYGAAVSAL
S.griseus   MFENQQNQHL SRRRLLGLAA LSCAAVACLT TISAAPQAAA AGRRAPRAGD GSFVEAVVIG TGYGAAVSAL
S.hygrospi  MFENQQNQHL SRRRLLGLAA LSGAAVTGLT TISAAPRAAA ADKRSPRADS GSFVPAVVIG TGYGAAVSAL
S.rimosus   MIEN---QHL SRRRLLGLAA LGGAAVAGMT TISAAPRAAA ACQQSPRACD CAFVPAVVIG TGYGAAVSAL
S.durhamen  ---MFAHQPL SRRRMLGMAA LGAAALAGQT TIAAAPRAAA ATATSG--SG GTFVPAVVVG TGYGAAVSAL
S.scleroti  ---MNAHQPL SRRRMLGLAA LGAAALAGQT TITAAPRAAA ATTTGV--SD GTFVPAVVVG TGYGAAVSAL
S.mutabili  ---MNAHQPL SRRRMLGLAA LGAAALAGQT TITAAPRAAA ATRTGV--SD GTLVPAVVVG TGYGAAVSAL
S.scabiei   -----MQRQL TRRHILGMAA LQTAAGLGLT RIGLQSARAA EP------DA VDNAPALVIG SGYGAAVAAL
S.mobaraen  ---------- -----MGAAA FGGGILSGAS GAEAAEAADV A-------RD GAFVPAVVVG TGYGAAVTAL
S.cellulos  ---------- -------MAA LQSAAALGFT RVGLQSARAA EP------DA VESAPAIVIG SGYGAAVAAL
S.prunicol  ---------- -------MIA LQTAATAGLT RIGLQSAQAV EP------AA VETAPAIVVG SGYGGAVAAL
S.bottrope  ---------- -------MAA LQTAATLGLT RIGLQSARAA EP------DA VDNAPAIVIG SGYGAAVAAL
Clustal Co                 *  :   .   * :                .          *:*:*  :***.**:**

L113
                  ....|....| ....|....| ....|....| ....|....| ....|....| ....|....| ....|....|
                       80         90        100        110        120        130        140
CHO         RLGEAGVQTL MLEMGQLWNQ PGPDGNIFCG MLNPDKRSSW FKNRTEAPLG SFLWLDVVNR NIDPYAGVLD
S.albulus   RLGEAGVETL MLEMGQLWNK PAEDGNVFCG MLTPDRRSSW FKSRTEAPLG SFLWLDVINR DIEPYAGVLD
S.virginia  RLGEAGVRTV MLEMGQLWNQ PGPDGNVFAG MLKPDKRSSW FKNRTEAPLG SFLWLDLANR DIDPYAGVLD
S.lavendul  RLGEAGVRTV MLEMGQLWNQ QGPDGNVFCG MLKPDKRSSW FKTRTEAPLG SFLWLDLANR DIDPYAGVLD
S.chattano  RLGEAGIPTL MLEMGQLWNK PADDGNVFCG MLKPDRRSSW FKSRTEAPLG SFLWLDVINR DIDPYAGVLD
S.natalens  RLGEAGIPTL MLEMGQLWNK PADDGNVFCG MLSPDRRSSW FKSRTEAPLG SFLWLDVINR DIDPYAGVLD
S.avermiti  RLGEAGVPTL MLEMGRLWNQ PGPDCNVFSG MLKPDKRSSW FKTRTEAPLG SFLWLDLANR DIEPYAGVLD
S.griseus   RLGEAGVPTL MLEMGRLWNK PAEDGNVFCG MLKPDRRSTW FKSRTEAPLG SFLWLDVVNR DIDPYAGVLD
S.hygrospi  RLGEAGVETL MLEMGQLWNK PAEDGNVFCG MLTPDRRSSW FKSRTEAPLG SFLWLDVINR DIEPYAGVLD
S.rimosus   RLGEAGIPTL MLEMGQLWNK PADDGNIFCG MLKPDRRSSW FKSRTEAPLG SFLWLDVINR NIDPYAGVLD
S.durhamen  RLGEAGVTTL MLEMGQLWNQ AGPDGNVFCG MLKPDKRSSW FKNRTEAPLG SFLWLDLANR DIDPYAGVLD
S.scleroti  RLGEAGISTL MLEMGQLWNQ PGPDGNIFCG TLAPDKRSSW FKTRTEAPLG SFLWLDLANR DIEPYAGVLD
S.mutabili  RLGEAGISTL MLEMGQLWNQ PGPDGNIFCG TLAPDKRSSW FKTRTEAPLG SFLWLDLANR DIEPYAGVLD
S.scabiei   RLGQAGIRTL VLEMGRAWTT PGADGKIFCS TKEPDERSMW FKTRTEAPLA TFLWLDVVNQ DISRYPGVLD
S.mobaraen  RIAEAGERVL MLEMGRKWDR PGADGRVFCG MLDPDRRSSW FRTRTAAPLG SFLWLDVVDR NIEPYAGVLD
S.cellulos  RLGQAGIRTL VLEMGRLWNT PGSDGKVFCS TAAPDQRSMW FKTRTEAPLG TFLWLDLVNR DITPYPGVLD
S.prunicol  RLGQAGITTL VLEMGRLWNT PGTDGKIFCS TAAPDKRSMW FKTRTEAPLA SFLWLDVVNK DITAYPGALD
S.bottrope  RLGQAGIRTL VLEMGRAWTT PGADGKIFCS TREPDERSMW FKTRTEAPLA TFLWLDVVNQ DISSYPGVLD
Clustal Co  **.:**   .: :****:  *   .**.:*..  **.**  *  *:.** **:. :*****: ::  :*   *.*.**

....|....| ....|....| ....|....| ....|....| ....|....| ....|....| ....|....|
                      150        160        170        180        190        200        210
CHO         RVNYDQMSVY VGRGVGGGSL VNGGMAVEPK RSYFEEILPR VDSSEMYDRY FPRANSMLRV NHIDTKWFED
S.albulus   RVHFDQMSVY VGRGVGGGSL VNGGMAVVPK RAYFEEVLPQ VDAAQMYERY FPRANAALKV NHIDPAWFEK
S.virginia  RVNFDQMSVY VGRGVGGGSL VNGGMAVAPK RSYFEEVLPR VDSAEMYSRY FPRANSMLRV NHIDDGWFES
S.lavendul  RVNYDQMSVY VGRGVGGGSL VNGGMAVVPK RSYFEEVLPR VDSAAMYDRY FPRANSMLRV NHIDNGWFEG
S.chattano  KVHFDQMSVY VGRGVGGGSL VNGGMAVVPK RSYFEEVLPR VDAAEMYDRY FPRANSMLKV NHIDKGWFEE
S.natalens  KVHFDQMSVY VGRGVGGGSL VNGGMAVVPK RSYFEEVLPR VDAAEMYDRY FPRANSMLKV NHIDKGWFEE
S.avermiti  RVNFDQMSVY LGRGVGGGSL VNGGMAVTPR RSYFEEVLPQ VDAEEMYTKY FPRANSTLRV NNIDKSWFEQ
S.griseus   RVHFDEMSVY VGRGVGGGSL VNGGMAVVPK RAYFEEVLPK VDAAEMYERY FPRANAALKV NHIDPAWFEK
S.hygrospi  RVHFDQMSVY VGRGVGGGSL VNGGMAVVPK RAYFEEVLPQ VDAAQMYERY FPRANAALKV NHIDPAWFEK
S.rimosus   KVHFDEMSVY VGRGVGGGSL VNGGMAVVPK RSYFEEVLPR VDAAQMYDRY FPRANSMLKV NHIDKGWFED
S.durhamen  RVNFDQMSVY VGRGVGGGSL VNGGMAVTPR RSYFEEVLPQ VDAEEMYTKY FPRANSTLRV NTVDKSWFEQ
S.scleroti  RVNFDQMSVY VGRGVGGGSL VNGGMAVTPR RSYFEEVLPQ VDADEMYSTY FPRANSGLRV KNIDEAWFEQ
S.mutabili  RVNFDQMSVY VGRGVGGGSL VNGGMAVTPR RSYFEEVLPQ VDADEMYSTY FPRANSGLRV KNVDEAWFEQ
S.scabiei   RVRHANMSVF LGRGVGGGSL VNGSMAVTPL RSYFAEQFPT VDTAEMYSTY FPRARSMLGV NTVDPAWFES
S.mobaraen  RVDFGSMAVY AGRGVGGGSL VNGGMAVAPR RDYLQRVLPR VDAAEMYRRY FPRARAMLRV NGIDRTWFEG
S.cellulos  RVHYDAMSVY VGRGVGGGSL VNGGMAVTPL RSYFAEQFPT VDSAEMYGTY FPRARSMLGV NSIDPAWFES
S.prunicol  RVHYDNMSVY VGRGVGGGSL VNGGMAVTPL QSYFAEQFPT VDATAMYGTY FPRARTMLGV NTVDPTWFES
S.bottrope  RVRYANMSVF LGRGVGGGSL VNGSMAVTPL QSYFAEQFPT VDTAEMYSTY FPRARSMLGV NTIDPAWFES
Clustal Co  :* .  *:*: ********* ***.*** *   : *: . :*  **: **  *  ****.: * *  :  :*  ***
```

*FIG. 1*

```
                    ....|....|    ....|....|    ....|....|    ....|....|    ....|....|    ....|....|    ....|....|
                         220            230            240            250            260            270            280
CHO         TEWYKFARVS REQAGKAGLG TVFVPNVYDF GYMQREAAGE VPKSALATEV IYGNNHGKQS LDKTYLAAAL
S.albulus   TEWYNFARVS REQAGKAGLS TTFVPNVYDF DHMQREAAGT APKSALAGEV IYGNNHGKQS LDKTYLAAAL
S.virginia  TEWYKFARVS RDQAQKAGLG TVHVPNVYDF DHMRREAAGE APKSALAGEV IYGNNHGKQS LDKTYLAAAL
S.lavendul  TDWYKFARVS RDQAQKAGLG TVHVPNVYDF DYMRREANGE VPKSALAAEV IYGNNHGKQS LDKTYLAAAL
S.chattano  TEWYKFARVS REQAGKAGLS TTFVPNVYDF DYMRREANGE SPKSALATEV IYGNNHGKQS LDKTYLAAAL
S.natalens  TEWYKFARVS REQAGKAGLG TTFVPNVYDF DYMRREANGE SPKSALATEV IYGNNHGKQS LDKTYLAAAL
S.avermiti  TDWYKFARVS RRQASNAGLS TTFVPNVYDW DYMRREADGA VPKSALAAEV IYGNNHCKVS LDKSYLAAAL
S.griseus   TEWYKFARVS REQASKAGLS ITFVFNVYDF GHMRREATGE APKSALAGEV IYGNNHGKQS LDKTYLAAAL
S.hygrospi  TEWYNFARVS REQAGKAGLS ITFVPNVYDF DHMQREAAGT APKSALAGEV IYGNNHGKQS LDKTYLAAAL
S.rimosus   TEWYKYARVS REQAGKAGLS TTFVPNVYDF GHMRREADGT APKSALAGEV IYGNNHGKQS LDKTYLAAAL
S.durhamen  TDWYTFARVS RQQAANAGLS TTFVPNVYDW DYMRREADGT VPKSALAAEV IYGNNHGKVS LDKSYLAAAL
S.scleroti  TEWYKYARVG RDQAANAGLS ITFVPNVYDW DYMRREADGS VPKSALAAEV IYGNNHGKVS LDKSYLADAL
S.mutabili  TEWYQYARVG REQARNAGLS ITFVPNVYDW DYMRREADGS VPKSALAAEV IYGNNHGKVS LDKSYLADAL
S.scabiei   TEWYRFSRVS RAHAAKAGLR ITFVPSVYDF DHMQREAAGT ATKSALAGEV IYGNNHGKKS LDKTYLAAAL
S.mobaraen  TEWYRYSRVA REQAARAGLR SVFLDNVYDF RHMRREADGT APRSALAGEL IYGNNHGRMS LDKTYVAAAL
S.cellulos  TEWYQFTRTS RKAADNTGLK TTFVPNVYDF GHMQREAAGT ATKSALGQEV IYGNNSGKKS LDKTYLASAL
S.prunicol  TEWYQFTRTS RKAAINTGLK TTFVPNVYDF GYMQQEAAGT ATKSALAQEV IYGNNYGKKS LDKTYLASAL
S.bottrope  TEWYRFSRVS RAHAEKAGLR TTFVPSVYDF GHMRREAAGT APKSALAGEV IYGNNHGKKS LDKTYLAAAL
Clustal Co  *:** ::*..  *  *  .:**   :..: .***:  :*::** *   .:***. *:  ***** *: *  ***;*:* **

....|....|    ....|....|    ....|....|    ....|....|    ....|....|    ....|....|    ....|....|
                         290            300            310            320            330            340            350
CHO         GTGKVTIQTL HQVKTIRQTK DGGYALTVEQ KDTDGKLLAT KEISCRYLFL GAGSLGSTEL LVRARDTGTL
S.albulus   GTGKVTIETL HRVTAIRQQA DGSYVLSVDQ SDANGTVIAH KEIACRHLFL GAGSLGSTEL LVRARDTGAL
S.virginia  GTGKVTIETL HQARTIRQQK DGTYLLTVEQ RDADGRLLAT KEISCRHLFL GAGSLGSTEL LLRARETGTL
S.lavendul  GTGKVTIETL HQARTIRQQK DGTYLLTVEQ KDADGRLLAT REISCRHLFL GAGSLGSTEL LLRARETGTL
S.chattano  CTGKVTIETL HQVKAIHQQP DGSYVLSVDQ IDTAGQTVAH KEIACRHLFL GAGSLGSTEL LVRARDTGAL
S.natalens  GTGKVTIETL HQVRAIHQQP DGSYVLSVDQ IDIAGQTVAH KEISCRHLFL GACSLGSTEL LVRARDTGAL
S.avermiti  GTGKVTIETL HQVKTIRQQN DGTYLLTVEQ RDIGGKLLGT KEVSCRHLFL GAGSLGSTEL LLRARETGTL
S.griseus   GTGKVTIETL HQVKAIRQQK DGGYVLSVDQ TDADGKTVGH KEIGCRHLFL GAGSLGSTEL LVRARDTGAL
S.hygrospi  GTGKVTIETL HRVTAIRQQA DGSYVLSVDQ SDANGTVIAH KEIACRHLFL GAGSLGSTEL LVRARDTGAL
S.rimosus   GTGKVTIETL HQVKAIRRQP DGSYVLSVVQ SDADGKVVAQ KEIGCRHLFL GAGSLGSIEL LVRARDTGTL
S.durhamen  GTGKVTIETL HQVRTIRQQN DGTYLLTVEQ RDADGKLLAT KEVSCRHLFL GAGSLGSTEL LLRARETGTL
S.scleroti  GTGKVAIETL HQVRTIRQRN DGTYLLTVEQ KDAQGGLIAT KEISCRHLFL GAGSLGSTEL LLRARETGTL
S.mutabili  GTGKVAIETL HQVKTIRQRN DGTYLLTVEQ KDAQGGLLAT KEISCRHLFL GAGSLGSTEL LLRARETGTL
S.scabiei   GTGNVTIHTM ERARGIRRLG DGTYVVTADR IDGTGAVVET KEYGCTYLFL GAGSVGTTEL LVRARAKGTL
S.mobaraen  RTGRVTIAPL HRAKSLRRRR AGGYVLTVER SDETGRRTAV KEIGCRRLFL GAGSLGTTEL LLRARETGAL
S.cellulos  GTGNVTIHTL EKVRAISRAA DGTYVLTADR IDLTGKVVET KQYGCTYLFL GGGSIGTTEL LVRARETGTL
S.prunicol  GTGKVTIHTM HQVKTIRQRN DGTYLLTVEQ KDAQGGLLAT KEISCRHLFL GGGSLGTTEL LVRARETGTL
S.bottrope  GTGNVTIHTM ERARGIRRLS DGTYVVTVDR LDDTGAVVET KEYGCTYLFL GAGSVGTTEL LVRARAKGTL
Clustal Co  **.*:*  .: .:.  : :       *  *  ::. :  *  *    :: .*  ***  *.**:*:*** *:*** .*:*

M362                                    M402        L412
                    ....|....|    ....|....|    ....|....|    ....|....|    ....|....|    ....|....|    ....|....|
                         360            370            380            390            400            410            420
CHO         PNLNSEVGAG WGPNGNIMTA RANHMWNPTG AHQSSIPALG IDAWDNSDSS VFAEIAPMPA GLETWVSLYL
S.albulus   PHLNAEVGEG WGPNGNIMTG RANHVWNPTG AHQSSIPALG IDDWDNPDAP VFAEIAPMPA GLETWVSLYL
S.virginia  PDLSSEIGAG WGPNGNIMTA RANHVWNPTG ANQSSIPALG IDDWDNPQNP VFAEIAPMPA GLETWVSLYL
S.lavendul  PDLSSEIGAG WGPNGNIMTA RANHVWNPTG ASQSSIPALG IDDWDNPAAP VFAEIAPMPA GVETWVSLYL
S.chattano  PDLNAEVGAG WGPNGNIMTG RANHVWNTTG AHQSSIPALG IDDWDNPAAP VFAEIAPMPA GLETWVSLYL
S.natalens  PDLNAEVGAG WGPNGNIMTG RANHVWNPTG AHQSSIPALG IDDWNNPTAP VFAEIAPMPA GLETWVSLYL
S.avermiti  PGLSPEVGGG WGPNGNIMTA RANHMWNPTG TKQSSIPALG IDDWDNPDTP VFAEIAPIPA GVETWVSTYL
S.griseus   PDLNAEVGGG WGPNGNIMTG RANHVWNPTG AHQSSTPALG IDDWNNAAAP VFAEIAPMPA GAETWVSLYL
S.hygrospi  PHLNAEVGEG WGPNGNIMTG RANHVWNPTG AHQSSIPALG IDDWDNPDAP VFAEIAPMPA GLETWVSLYL
S.rimosus   PELNAEVGAG WGPNGNIMIG RANHVWNPTG AHQSSIPALG IDDWDNPAAP VFAEIAPMPA GLETWVSLYL
S.durhamen  PDLSSEIGGG WGPNGNIMTA RANHMWNPTG TKQSSTPALG IDDWDNPNNP VFAEIAPMPA GVETWVSLYL
S.scleroti  ANLSSEIGGG WGPNGNIMTA RANHVWNTTG SNQSSIPALG IDDWDNPDSP VFAEIAPMPA GLETWVSLYL
S.mutabili  ADLSPEIGGG WGPNGNIMTA RANHMWNPTG SNQSSIPALG IDDWDNPDNP VFAEIAPMPA GLETWVSLYL
S.scabiei   PALNASVGAG WGPNGNVMLG RANHLWDTVG ANQSTMPVMG IDDWANTANP VFAEIAPLPT GLEHWVSLYL
S.mobaraen  PDLGPEIGRG WGPNGNVMAA RANHGTDPTG CHQSTVPALG LDDWDDPRHP VFAEVTPVPA GTETWISLYI
S.cellulos  PALNASVGSG WGTNGNVMLG RANHVWDTVG ANQSTMPVMG IDDWANASNP VFAEIAPLPI GLEHWVSLYL
S.prunicol  PALNSSVGAG WGPNGNIMVG RANHIWDTVG ANQSTMPVMG IDDWANTDNP VFAEIAPLPI GFETWVSLYL
S.bottrope  PALHASVGAG WGSNGNVMLG RANHLWDTVG ANQSTMPVMG IDDWANTANP VFAEIAPLPT GLEHWVSLYL
Clustal Co  . *  ..:*  *  **.***  *  . ****  :..*   **:*.:*  :* * :.    *****::*:*   * *  *:*:**:
```

*FIG. 2*

```
                                                                            D468          Y483
              ....|....| ....|....| ....|....| ....|....| ....|....| ....|....| ....|....|
                      430        440        450        460        470        480        490
CHO           AITKNPQRGT FVYDAATDRA KLNWTRDQNA PAVNAAKALF DRINKANGTI YRYDLFGTQL KAFADDFCYH
S.albulus     AITKNPERGS FVYDKATDRA MLRWTREQNA PAVAAAKSLF DRINKANTTM YRYDLFGPQL KNFADDFCYH
S.virginia    AITKNPERGT FAYDAATDRA ALRWTRDQNT PAVSAAKSLF DRINKANTTM YRYDLFGKQL KAFSDDFTYH
S.lavendul    AITKNPERGA FVYDAANDRA NLRWTRDQNT PAVNAAKSLF DRVNRANTTM YRYDLFGKQL KAFSDDFCYH
S.chattano    AITKNPERGT FVYDKATDRA ALRWTRDQNT PAVNAAKSLF DRINKANTTM YRYDLFGPQL KNFSDDFCYH
S.natalens    AITKNPERGT FVYDKATDRA ALRWTRDQNT PAVNAARSLF DRINKANGTM YRYDLFGPQL KNFSDDFCYH
S.avermiti    AITKNPERGT FVYDAAKDRA DLRWTRDQNA PAIAAAKSLF DRINKANATI YRYDLFGKQI KAFADDFCYH
S.griseus     AITKNPERGT FVYDKATDRV ALRWTRDQNT PAVNAAKSLF DRINQANITV YRYDLFGKQV KAFSDDFSYH
S.hygrospi    AITKNPQRGS FVYDKATDRA MLRWTREQNA PAVAAAKSLF DRINKANTTM YRYDLFGPQL KNFADDFCYH
S.rimosus     AITKNPERGT FVYDKATDRA KLRWTRDQNT PAVNAAKSLF DRINKANTTM YRYDLFGSQL KNFSDDFSYH
S.durhamen    AITKNPERGT FVYDAAKDRA DLRWTRDQNA PAVNAAKSLF DRINKANITI YRYDLFGKQI KAFADDFCYH
S.scleroti    AITKNPERGT FVYDAAKDRA DLRWTREQNA PAVAAAKSLF DRINRANSTI YRYDLFGPQI KAFADDFCYH
S.mutabili    AIAKNPERGT FVYDAAKDRA DLRWTREQNA PAVAAAKSLF DRINKANSTI YRYDLFGSQI KAFADDFCYH
S.scabiei     AITKNTERAS KLGWSAAQSA VSSSMAKKLF DRINSANSTM YRYDLFGSSN KVFADDFTYH
S.mobaraen    AITRNPERGT FVYDRATDRM GLRWTRDQNR PAVDAARSFF DRVNRANRTD YRYDLFGPRA KAFADDFTYH
S.cellulos    AITKNPQRAS FTYDSGSDGV RLSWTAAQSA VSVNMAKKLF DRINSANSTI YRYDLFGSSS KVFADDFCYH
S.prunicol    AITKNPQRAS FAYDSASGTV KLGWTAAQSA VSVAMAKKLF DRINSANATL YRYDLFGSTS KVFADDFCYH
S.bottrope    AITKNPERAS FTYDAASDSA KLGWSAAQSA VSSSMAKKLF DRINSANSTM YRYDLFGSSN KVFADDFTYH
Clustal Co    **::*.:*.:  *.**  ...       *  *:    *.:  :       :  *   *  **:*  **   *  ***:***    *  *:***  **

S518 V519
              ....|....| ....|....| ....|....| ....|....| ....|....| ....|....| ....|....|
                      500        510        520        530        540        550
CHO           PLGGCVLGKA TDDYGRVAGY KNLYVTDGSL IPGSVGVNPF VTITALAERN VERIIKQDVT AS---
S.albulus     PLGGCVLGKA TDDYGRVAGY HNLYVTDGAL TPGSIGVNPF VTITALAERN IERVIAEDVR TAA--
S.virginia    PLGGCVLGKA TDDYGRVAGY KNLYVTDGSL IPGSIGVNPF VTITALAERN IERVIRQDVT AA---
S.lavendul    PLGGCVLGKA TDDYGRVSGY KNLYVTDGAL IPGSIGVNPF VTITALAERN IERVIQQDIK AS---
S.chattano    PLGGCVLGKA TDGYGRVAGY RNLYVTDGAL IPGSIGVNPF VTITALAERN IERIIAEDVK AA---
S.natalens    PLGGCVLGKA TDGYGRVAGY HNLYVTDGAL IPGSIGVNPF VTITALAERN IERIIAEDVK AA---
S.avermiti    PLGGCVLGKA TDDYGRVTGY KNLYVTDGSL IPGSIGVNPF VTIAALAERN IERVIKQDIA DS---
S.griseus     PLGGCVLGKA TDLYGRVAGH RNLYVTDGSL IPGSIGVNPF VTITALAERN IERIIAEDVK AA---
S.hygrospi    PLGGCVLGKA TDDYGRVAGY HNLYVTDGAL IPGSIGVNPF VTITALAERN IERVIAEDVR TAA--
S.rimosus     PLGGCVLGKA TDLYGRVAGY RNLYVMDGAL VPGSIGVNPF VTITALAERN IERIIAEDVK AA---
S.durhamen    PLGGCVLGKA TDNYGRVAGY KNLYVTDGSL IPGSIGVNPF VTITALAERN VERIIKEDVA NS---
S.scleroti    PLGGCVLGKA TDNYGRVTGY KNLYVTDGSL IPGSIGVNPF VTITALAERN VERIIKEDVT GS---
S.mutabili    PLGGCVLGKA TDNYGRVTGY KNLYVTDGSL IPGSIGVNPF VTITALAERN VERIIKEDVT GS---
S.scabiei     PLGGCVLGRA TDDYGRVKGY ENLYVTDGSL VPGSIGVNPF VTITALAERN VARVLVEDTA P----
S.mobaraen    PLGGCVLGRA TDPYGRIPGH PGLYVTDGSL VPGSIGVNPF LTITALAERN IERIVRQDVL PASGR
S.cellulos    PLGGCVLGRA TDDYGRVKGY SKLYVTDGSL VPGSIGVNPF VTITALAERT MARVLAEDTA P----
S.prunicol    PLGGCVLGSA TDNYGRVKGY SKLYVTDGSL VPGNIGVNPF VTITALAERT LERVLAEDF- -----
S.bottrope    PLGGCVLGRA TDDYARVKGY SKLYITDGSL VPGSIGVNPF VTITALAERT MARILVEDTA P----
Clustal Co    ******** *  ** *.*: *:    **: **:*  :**:*****  :**:*****. :  *:: :*
```

*FIG. 3*

◎ Around substrate-binding site
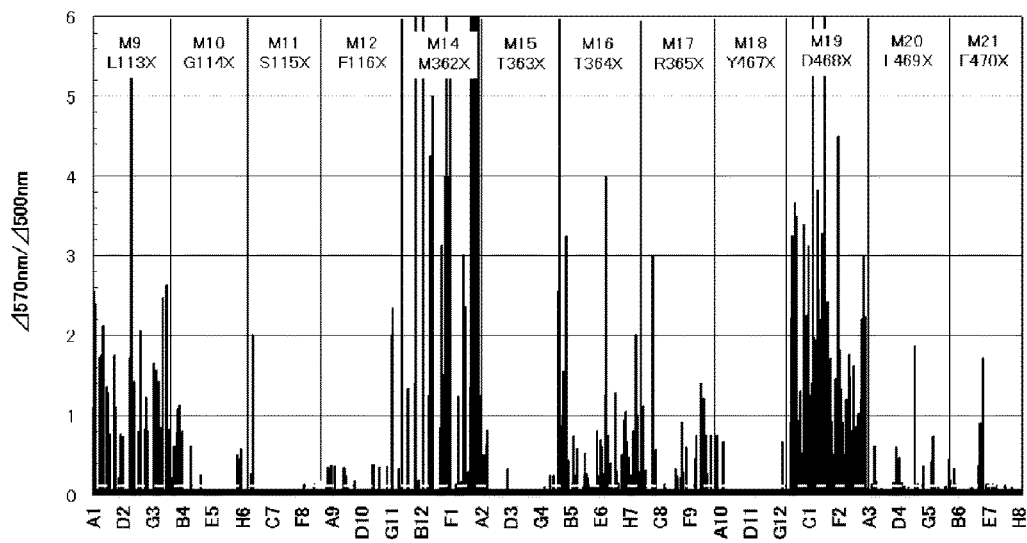
◎ Around active center
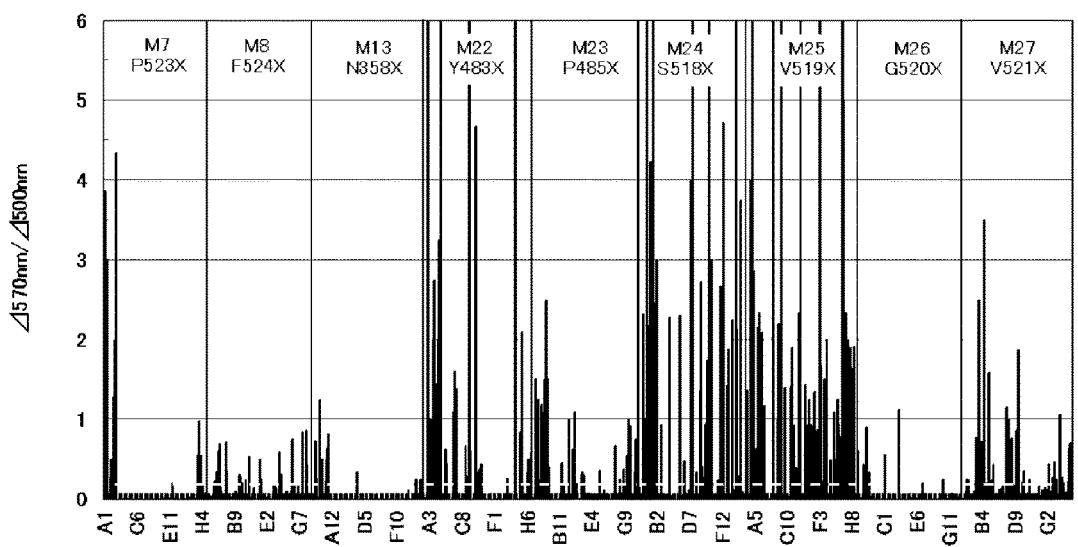
FIG. 4

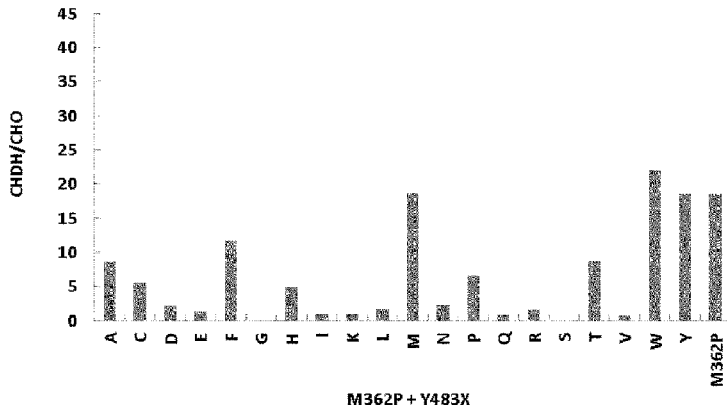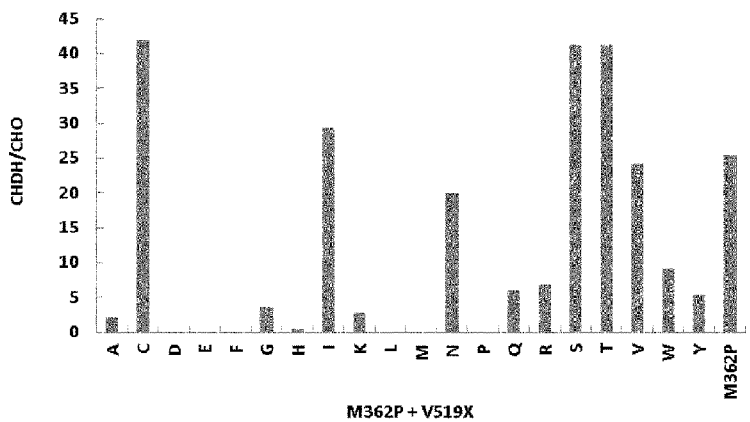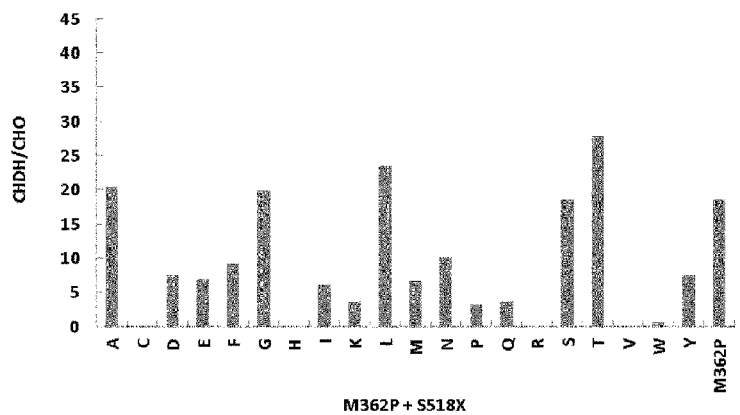
*FIG. 7*

| Sample | Protein mg/mL | Activity value (U/mL) | | Specific activity (U/mg) | | Ratio | Increase ratio (times) |
|---|---|---|---|---|---|---|---|
| | | CHO | CHDH | CHO | CHDH | CHDH/CHO | |
| Wild type | 2.15 | 107.0 | 0.0008 | 49.8 | 0.0004 | 0.000007 | 1 |
| V228A | 6.03 | 0.05 | 0.20 | 0.008 | 0.034 | 4 | 614,831 |
| M362P | 5.41 | 0.03 | 0.47 | 0.006 | 0.086 | 14 | 1,918,801 |
| M362P + L412Y | 4.65 | 0.01 | 0.18 | 0.002 | 0.039 | 17 | 2,392,857 |
| M362P + Y483W | 9.53 | 0.01 | 2.41 | 0.001 | 0.253 | 265 | 36,942,356 |
| M362P + S518T | 0.40 | 0.02 | 0.51 | 0.061 | 1.292 | 21 | 2,963,340 |
| M362P + V519C | 0.77 | 0.04 | 1.25 | 0.048 | 1.631 | 34 | 4,785,714 |

*FIG. 8*

| No | Mutation site of Streptomyces sp. | Corresponding position of Brevibacterium sterolicum |
|---|---|---|
| 1 | L113 | P76 |
| 2 | M362 | M325 |
| 3 | M402 | L365 |
| 4 | L412 | L375 |
| 5 | D468 | D431 |
| 6 | Y483 | Y446 |
| 7 | S518 | N481 |
| 8 | V519 | V482 |

FIG. 9

MUTATED ENZYME HAVING DEHYDROGENASE ACTIVITY AND USE THEREOF

TECHNICAL FIELD

The present invention relates to a technique for mutating an enzyme, and use thereof, and specifically to a cholesterol oxidase having dehydrogenase activity and its gene, and their preparation and use. The present application claims priority based on Japanese Patent Application No. 2014-21959 filed on Oct. 28, 2014, and the whole content of the patent application is incorporated herein by reference.

BACKGROUND ART

Simple cholesterol measuring instruments using electrochemical biosensors are widely used. These biosensors use cholesterol oxidase (hereinafter abbreviated as "CHO") and cholesterol dehydrogenase (hereinafter abbreviated as "CHDH"), each of which is an enzyme acting on cholesterol as substrate (for example, see Patent Documents 1 to 3). Both of CHO and CHDH have high specificity for cholesterol.

PRIOR ART DOCUMENTS

Patent Documents

Patent document 1: JP H11-002618 A
Patent document 2: JP 2001-343348 A
Patent document 3: JP 2000-329738 A Non-Patent Document Non-Patent document 1: Katsuhiro Kojima et al., Journal of molecular catalysis B: Enzymatic 88 (2013) 41-46

SUMMARY OF INVENTION

Technical Problems

The measurement using CHO may be affected by dissolved oxygen in the sample to be measured by a biosensor, and the risk of influence of the dissolved oxygen on the measurement result has been pointed out. In contrast, the measurement using CHDH has the advantage of being not affected by the dissolved oxygen in the sample to be measured by a biosensor. However, CHDH requires NAD as a coenzyme, so that NAD must be further added to the measurement system. Accordingly, the operation of the measurement using CHDH is complicated, NAD is relatively expensive, and thus the industrial use of the method is disadvantageous in regard to cost. Therefore, demanded is a novel enzyme which is safe from the influence of dissolved oxygen and requires no addition of NAD. In order to satisfy this demand, the object of the present invention is to provide an enzyme which can be used for the measurement of cholesterol, and has high practicality.

Solutions to the Problems

As a means for solving the above-mentioned problems, approximation of CHO to CHDH (imparting dehydrogenase activity) can be contemplated. This method may allow acquiring an enzyme having the advantage of CHO, more specifically, inclusion of FAD as a coenzyme. This enzyme allows the measurement of cholesterol without the addition of NAD and without being influenced by dissolved oxygen. In prior art, imparting dehydrogenase activity to CHO has been attempted by enzyme modification using a gene modification technique (Non-Patent Document 1), but this method is not suitable for industrial use from the viewpoint of activity value.

As shown in Examples mentioned below, the inventors conducted various experiments under the strategy of "imparting dehydrogenase activity to CHO", and succeeded in identification of mutation sites (amino acid residues) which are effective for imparting dehydrogenase activity to CHO. The mutant with a mutation (amino acid substitution) at the identified mutation site showed much higher dehydrogenase activity than that in the previous report (Non-Patent Document 1).

Meanwhile, it is often experienced that it is highly possible that an additive or synergistic effect is generated by combining effective two amino acid mutations. Through actual study of the effect of the combination of mutation sites, it was found that the combination of mutation sites was effective, and the particularly effective combinations of mutation sites were successfully identified.

Furthermore, considering the technical common knowledge that enzymes of the same kind are highly similar in structures (primary structure and steric structure) and that it is highly possible that similar mutation generates a similar effect, it can be said that the mutation technique found by the present inventors can be applied to the other CHOs having high similarity in structure with the *Streptomyces* microorganism (*Streptomyces* sp.)-derived CHO as shown in the Examples mentioned below.

The present invention shown below is based on the above-mentioned accomplishment and observation.

[1] A mutant enzyme consisting of an amino acid sequence in which one or more amino acid(s) selected from the group consisting of the following (1) to (8) has/have been substituted by another amino acid in the amino acid sequence of a microorganism-derived cholesterol oxidase, the mutant enzyme having a higher ratio of cholesterol dehydrogenase activity to cholesterol oxidase activity (CHDH activity/CHO activity) than the microorganism-derived cholesterol oxidase:

(1) an amino acid corresponding to the amino acid at the position 113 of the amino acid sequence of SEQ ID NO: 1;
(2) an amino acid corresponding to the amino acid at the position 362 of the amino acid sequence of SEQ ID NO: 1;
(3) an amino acid corresponding to the amino acid at the position 402 of the amino acid sequence of SEQ ID NO: 1;
(4) an amino acid corresponding to the amino acid at the position 412 of the amino acid sequence of SEQ ID NO: 1;
(5) an amino acid corresponding to the amino acid at the position 468 of the amino acid sequence of SEQ ID NO: 1;
(6) an amino acid corresponding to the amino acid at the position 483 of the amino acid sequence of SEQ ID NO: 1;
(7) an amino acid corresponding to the amino acid at the position 518 of the amino acid sequence of SEQ ID NO: 1; and
(8) an amino acid corresponding to the amino acid at the position 519 of the amino acid sequence of SEQ ID NO: 1.

[2] The mutant enzyme according to [1], wherein the amino acid sequence of the microorganism-derived cholesterol oxidase shows an identity of 65% or more with the amino acid sequence of SEQ ID NO: 1.

[3] The mutant enzyme according to [1] or [2], wherein the amino acid to be substituted is the amino acid of (2), and the amino acid after substitution is proline.

[4] The mutant enzyme according to [1] or [2], wherein the amino acid to be substituted is the combination of the amino acids of (2) and (4), the combination of the amino acids of (2) and (6), the combination of the amino acids of (2) and (7), or the combination of the amino acids of (2) and (8).

[5] The mutant enzyme according to [4], wherein the amino acid after substitution is proline for the amino acid of (2), tyrosine for the amino acid of (4), methionine or tryptophan for the amino acid of (6), glycine, leucine, threonine or alanine for the amino acid of (7), and cysteine, isoleucine, serine, or threonine for the amino acid of (8).

[6] The mutant enzyme according to [1], which consists of any of the amino acid sequences of SEQ ID NOs: 2 to 18.

[7] A gene coding for the mutant enzyme according to any one of [1] to [6].

[8] The gene according to [7], which comprises any of the base sequences of SEQ ID NOs: 20 to 36.

[9] A recombinant DNA comprising the gene according to [7] or [8].

[10] A microorganism having the recombinant DNA according to [9].

[11] A method for measuring cholesterol in a sample using the mutant enzyme according to any one of [1] to [6].

[12] A reagent for measuring cholesterol, comprising the mutant enzyme according to any one of [1] to [6].

[13] A kit for measuring cholesterol, comprising the reagent for measuring cholesterol according to [12].

[14] An enzyme preparation comprising the mutant enzyme according to any one of [1] to [6].

[15] A method for preparing a mutant enzyme, comprising the following steps (I) to (III):
(I) a step of preparing a nucleic acid that codes for any of the amino acid sequences of SEQ ID NOs: 2 to 18;
(II) a step of expressing the nucleic acid, and
(III) a step of collecting an expressed product.

BRIEF DESCRIPTION OF THE DRAWINGS

FIG. 1 compares the amino acid sequences of *Streptomyces* sp.-derived CHO, indicating that the L113, M362, L412, D468, and Y483 derived from *Streptomyces* sp. (CHO in the figure) are highly conserved. The homology of the amino acid sequences of the CHOs to the amino acid sequence (SEQ ID NO: 1) of the *Streptomyces* sp.-derived CHO sp. are as follows.
*Streptomyces albulus*-derived CHO (SEQ ID NO: 37): 81%
*Streptomyces virginiae*-derived CHO (SEQ ID NO: 38): 85%
*Streptomyces lavendulae*-derived CHO (SEQ ID NO: 39): 84%
*Streptomyces chattanoogensis*-derived CHO (SEQ ID NO: 40): 82%
*Streptomyces natalensis*-derived CHO (SEQ ID NO: 41): 82%
*Streptomyces avermitilis*-derived CHO (SEQ ID NO: 42): 82%
*Streptomyces griseus*-derived CHO (SEQ ID NO: 43): 81%
*Streptomyces hygrospinosus*-derived CHO (SEQ ID NO: 44): 81%
*Streptomyces rimosus*-derived CHO (SEQ ID NO: 45): 84%
*Streptomyces durhamensis*-derived CHO (SEQ ID NO: 46): 83%
*Streptomyces sclerotialus*-derived CHO (SEQ ID NO: 47): 82%
*Streptomyces mutabilis*-derived CHO (SEQ ID NO: 48): 82%
*Streptomyces scabiei*-derived CHO (SEQ ID NO: 49): 67%
*Streptomyces mobaraensis*-derived CHO (SEQ ID NO: 50): 67%
*Streptomyces cellulosae*-derived CHO (SEQ ID NO: 51): 67%
*Streptomyces prunicolor*-derived CHO (SEQ ID NO: 52): 67%
*Streptomyces bottropensis*-derived CHO (SEQ ID NO: 53): 66%

FIG. 2 is continued from FIG. 1.

FIG. 3 is continued from FIG. 2.

FIG. 4 shows the result of the experiment using a random mutagenesis library. Random mutation was introduced into the amino acid residues (18 points) around the substrate-binding site and the amino acid residues (9 points) around the active center of the *Streptomyces* sp.-derived CHO by a PCR method using a random mutagenesis primer.

FIG. 7 shows the evaluation of double variants. The effect of the combination of the mutation M362P and other mutations (saturation mutagenesis of Y483, saturation mutagenesis of 5518, and saturation mutagenesis of V519 as mutagenesis around the active center) was studied.

FIG. 8 compares the activity ratio (CHDH activity/CHO activity). The CHDH activity (specific activity) and CHO activity (specific activity) were measured, and the activity ratio (CHDH activity/CHO activity) was calculated. The activity ratios of the variants were compared using a wild type as the standard.

FIG. 9 compares the structures of *Streptomyces* sp.-derived CHO and Brevibacterium sterolicum-derived CHO. For *Streptomyces* sp.-derived CHO, the methionine at the head of the presequence of the precursor (prepro protein) was numbered 1, and the positions of each amino acid residue were identified. For Brevibacterium sterolicum-derived CHO, the methionine at the head of the mature protein was numbered 1, and the positions of each amino acid residue were identified.

DESCRIPTION OF EMBODIMENTS

Figure 5:
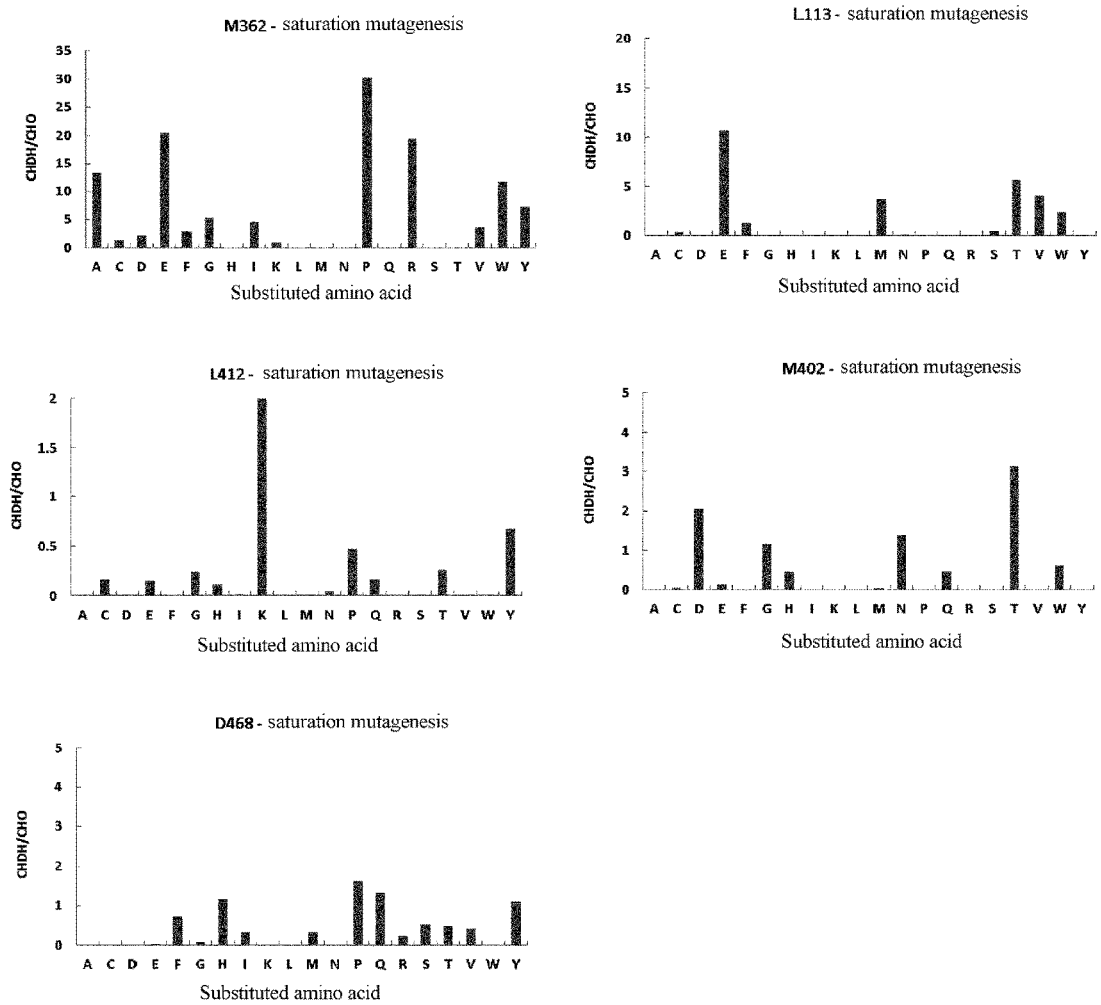
FIG. 5 shows the result of the experiment using a saturation mutagenesis library. Saturation mutation was introduced into the mutation sites (5 points) around the substrate-binding site by a PCR method using the primers corresponding to each of the 20 amino acids.

For convenience in explanation, a part of the terms used with respect to the present invention will be defined below.
(Terms)

The term "mutant enzyme" is an enzyme that is obtained by mutating or modifying "a base enzyme" by the means disclosed by the present specification. In the present specification, the term "mutant enzyme", the term "mutant-type enzyme" and the term "modified enzyme" are interchangeably used. The base enzyme is typically a wild type enzyme. However, this does not interfere with the application of enzyme that has already undergone an artificial operation to the present invention as the "base enzyme". The "base enzyme" is also referred to as "enzyme to be mutated" or "enzyme to be mutated" in the present specification.

Approximation of a certain enzyme (referred to as enzyme A for convenience in explanation) to another enzyme (referred to as enzyme B for convenience in explanation), more specifically, modification of one or more characteristics of the enzyme A for approximating them to the corresponding characteristics of the enzyme B is referred to as "approximation of the enzyme A to the enzyme B". In the present invention, cholesterol oxidase (CHO) is approximated to cholesterol dehydrogenase (CHDH), more specifically, oxidase activity of CHO is decreased while cholesterol dehydrogenase activity is imparted or increased. This modification is herein referred to as "imparting dehydrogenase activity". The mutant enzyme of the present invention having dehydrogenase activity has a higher ratio of CHDH activity to CHO activity (CHDH activity/CHO activity) in comparison with the original enzyme (CHO before imparting dehydrogenase activity).

In the present invention, "substitution of amino acid" is conducted as mutation or modification. Accordingly, differences are found in some amino acid residues in comparison between the mutant enzyme and enzyme to be mutated.

In the specification, amino acids are designated according to the common practice, as their single letters as described below:

methionine: M; serine: S; alanine: A; threonine: T; valine: V; tyrosine: Y; leucine: L; asparagine: N; isoleucine: I; glutamine: Q; proline: P; aspartic acid: D; phenylalanine: F; glutamic acid: E; tryptophan: W; lysine: K; cysteine: C; arginine: R; glycine: G; and histidine: H.

In addition, an amino acid residue at a mutation site (an amino acid residue to be substituted with another amino acid) is expressed in a combination of the above-described single letter representing the kind of the amino acid residue and the figure representing the position of the amino acid residue. For example, if methionine at position 362 is a mutation site, then the amino acid is designated as "M362."

(Enzyme Prepared by Mutating Cholesterol Oxidase)

The first aspect of the present invention relates to an enzyme prepared by mutating a microorganism-derived cholesterol oxidase (CHO) (hereinafter may be referred to as "mutant CHO"). The mutant CHO of the present invention has an amino acid sequence in which one or two or more of the amino acid(s) selected from the group consisting of the following (1) to (8) has/have been substituted by (an)other amino acid(s) in the amino acid sequence of a microorganism-derived CHO (enzyme to be mutated).

(1) an amino acid corresponding to the amino acid at the position 113 of the amino acid of SEQ ID NO: 1
(2) an amino acid corresponding to the amino acid at the position 362 of the amino acid of SEQ ID NO: 1
(3) an amino acid corresponding to the amino acid at the position 402 of the amino acid of SEQ ID NO: 1
(4) an amino acid corresponding to the amino acid at the position 412 of the amino acid of SEQ ID NO: 1
(5) an amino acid corresponding to the amino acid at the position 468 of the amino acid of SEQ ID NO: 1
(6) an amino acid corresponding to the amino acid at the position 483 of the amino acid of SEQ ID NO: 1
(7) an amino acid corresponding to the amino acid at the position 518 of the amino acid of SEQ ID NO: 1
(8) an amino acid corresponding to the amino acid at the position 519 of the amino acid of SEQ ID NO: 1

As shown in Examples mentioned below, the amino acid at the position 113, the amino acid at the position 362, the amino acid at the position 402, the amino acid at the position 412, and the amino acid at the position 468 in the amino acid sequence shown in SEQ ID NO: 1 are around the substrate-binding site of Streptomyces sp.-derived CHO, and expected to be important for the interaction with the substrate. On the other hand, the amino acid at the position 483, the amino acid at the position 518, and the amino acid at the position 519 in the amino acid sequence shown in SEQ ID NO: 1 are located around the active center of Streptomyces sp.-derived CHO, and expected to be important for the enzyme activity. In the present invention, dehydrogenase activity is imparted by modifying the amino acids corresponding to these amino acids, which are expected to be important for the characteristics of CHO. The mutant enzyme of the present invention shows a characteristic that the ratio of cholesterol dehydrogenase activity to cholesterol oxidase activity (CHDH activity/CHO activity) is higher in comparison with the enzyme before mutation (more specifically, microorganism-derived cholesterol oxidase as the enzyme to be mutated). The "CHDH activity/CHO activity" of the mutant enzyme (in terms of specific activity) is, for example, 5 or more, preferably 10 or more, more preferably 20 or more, and even more preferably 30 or more. As compared with the enzyme to be mutated, the mutant enzyme shows "CHDH activity/ CHO activity" of, for example, $1.0 \times 10^6$ times or more, preferably $1.5 \times 10^6$ times or more, more preferably $2.0 \times 10^6$ times or more, and even more preferably $1.0 \times 10^7$ times or more (comparison based on specific activity).

Herein, the term "corresponding" when used for an amino acid residue in the present specification means contributing equally to exhibition of functions among proteins (enzymes) being compared. For example, when an amino acid sequence for comparison to the base amino acid sequence (that is, the amino acid sequence set forth in SEQ ID NO: 1) is aligned while considering partial homology of the primary structure (that is, an amino acid sequence) so that the most appropriate comparison can be achieved (in this event, the alignment may be optimized by introducing gaps if necessary), an amino acid located at a position corresponding to a specific amino acid in the base amino acid sequence can be specified as a "corresponding amino acid". The "corresponding amino acid" can also be specified by comparison between conformations (three-dimensional structures) in place of or in addition to the comparison between primary structures. Utilization of conformational information can give highly credible comparison results. In this case, a technique of performing an alignment with comparing atomic coordinates of conformations of a plurality of enzymes can be adopted. Conformational information of an enzyme to be mutated is available from, for example, the Protein Data Bank (http://www.pdbj.org/index_j.html).

One example of a method for determination of a protein conformation by the X-ray crystal structure analysis will be shown below.

(1) A protein is crystallized. Crystallization is essential to determine a conformation, and in addition, crystallization is industrially useful as a purification method of a protein at high purity and a stable preservation method of a protein at high density. In this case, it is preferable that a protein to which a substrate or its analogous compound as a ligand is bound is used for crystallization.

(2) The prepared crystal is irradiated with X-ray to collect diffraction data. There are many cases that a protein crystal is damaged due to X-ray irradiation and the diffraction ability is deteriorated. In such cases, a low-temperature measurement technique of rapidly cooling the crystal to about −173° C. and collecting diffraction data in the state has recently prevailed. In addition, ultimately, synchrotron orbit radiation having high luminance is utilized to collect high resolution data that is used for structural determination.

(3) In addition to the diffraction data, phase information is necessary in order to perform the crystal structure analysis. When a crystal structure of an analogous protein to a desired protein is unknown, it is impossible to determine the structure in a molecular substitution method, and a phase problem has to be solved by a heavy-atom isomorphous replacement method. The heavy-atom isomorphous replacement method is a method in which a metallic atom having a high atomic number such as mercury or platinum is introduced into a crystal and contribution of a large X-ray scattering ability of such a metallic atom to X ray diffraction data is utilized to collect phase information. The determined phase is possibly improved by smoothing an electron density of a solvent region in the crystal. Since a water molecule in the solvent region has large fluctuation, the electron density is hardly observed, and thus adjusting the electron density in this region to close to 0 makes it possible to approach the real electron density, which results in improving a phase. When plural molecules are contained in an asymmetrical unit, equation of electron densities of these molecules makes it possible to more significantly improve a phase. A model of a protein is fit to an electron density map calculated using the phase improved as described above. This process is performed on computer graphics using a program such as QUANTA made by MSI Co. (USA). After the process, structure refinement is performed using a program such as X-PLOR made by MSI Co. to complete the structure analysis. When a crystal structure of an analogous protein to a desired protein is known, it can be determined in a molecular substitution method using the atomic coordinate of the known protein. Molecular substitution and structure refinement can be performed using a program such as CNS_SOLVE ver.11.

The microorganism-derived CHO as the enzyme to be mutated is preferably a *Streptomyces* sp.-derived CHO (an example of the amino acid sequence is shown in SEQ ID NO: 1), or the one having high homology to the *Streptomyces* sp.-derived CHO. A specific example of the latter is a CHO having an amino acid sequence showing homology of 65% or more, preferably 80% or more, and more preferably 90% or more to the amino acid sequence of SEQ ID NO: 1. Examples of the CHO having such high homology include *Streptomyces albulus*-derived CHO (SEQ ID NO: 37), *Streptomyces virginiae*-derived CHO (an example of the amino acid sequence is shown in SEQ ID NO: 38), *Streptomyces lavendulae*-derived CHO (an example of the amino acid sequence is shown in SEQ ID NO: 39), *Streptomyces chattanoogensis*-derived CHO (an example of the amino acid sequence is shown in SEQ ID NO: 40), *Streptomyces natalensis*-derived CHO (an example of the amino acid sequence is shown in SEQ ID NO: 41), *Streptomyces avermitilis*-derived CHO (an example of the amino acid sequence is shown in SEQ ID NO: 42), *Streptomyces griseus*-derived CHO (an example of the amino acid sequence is shown in SEQ ID NO: 43), *Streptomyces hygrospinosus*-derived CHO (an example of the amino acid sequence is shown in SEQ ID NO: 44), *Streptomyces rimosus*-derived CHO (an example of the amino acid sequence is shown in SEQ ID NO: 45), *Streptomyces durhamensis*-derived CHO (an example of the amino acid sequence is shown in SEQ ID NO: 46), *Streptomyces sclerotialus*-derived CHO (an example of the amino acid sequence is shown in SEQ ID NO: 47), *Streptomyces mutabilis*-derived CHO (an example of the amino acid sequence is shown in SEQ ID NO: 48), *Streptomyces scabiei*-derived CHO (an example of the amino acid sequence is shown in SEQ ID NO: 49), *Streptomyces mobaraensis*-derived CHO (an example of the amino acid sequence is shown in SEQ ID NO: 50), *Streptomyces cellulosae*-derived CHO (an example of the amino acid sequence is shown in SEQ ID NO: 51), *Streptomyces prunicolor*-derived CHO (an example of the amino acid sequence is shown in SEQ ID NO: 52), and *Streptomyces bottropensis*-derived CHO (an example of the amino acid sequence is shown in SEQ ID NO: 53). FIGS. 1 to 3 compare the alignments of SEQ ID NOs: 1, 37 to 53. On the other hand, other specific examples of the microorganism-derived CHO include Brevibacterium sterolicum-derived CHO (an example of the amino acid sequence is shown in SEQ ID NO: 54), Nocardia sp.-derived CHO (an example of the amino acid sequence is shown in SEQ ID NO: 55), and Burkholderia cepacia-derived CHO (an example of the amino acid sequence is shown in SEQ ID NO: 56). For these CHOs, for example, the "corresponding amino acid" may be identified by the comparison of their steric structures (three-dimensional structures).

When the *Streptomyces* sp.-derived CHO having the amino acid sequence of SEQ ID NO: 1 is used as the enzyme to be mutated, the amino acid of (1) is the amino acid at the position 113 of SEQ ID NO: 1, the amino acid of (2) is the amino acid at the position 362 of SEQ ID NO: 1, the amino acid of (3) is the amino acid at the position 402 of SEQ ID NO: 1, the amino acid of (4) is the amino acid at the position 412 of SEQ ID NO: 1, the amino acid of (5) is the amino acid at the position 468 of SEQ ID NO: 1, the amino acid of (6) is the amino acid at the position 483 of SEQ ID NO: 1, the amino acid of (7) is the amino acid at the position 518 of SEQ ID NO: 1, and the amino acid of (8) is the amino acid at the position 519 of SEQ ID NO: 1.

On the other hand, when the Brevibacterium sterolicum-derived CHO having an amino acid sequence of SEQ ID NO: 54 (protein data bank (PDB): 3COX, SEQ ID NO: 54) is used as the enzyme to be mutated, the amino acid of (1) is the amino acid at the position 76 of SEQ ID NO: 54, the amino acid of (2) is the amino acid at the position 325 of SEQ ID NO: 54, the amino acid of (3) is the amino acid at the position 365 of SEQ ID NO: 54, the amino acid of (4) is the amino acid at the position 375 of SEQ ID NO: 54, the amino acid of (5) is the amino acid at the position 431 of SEQ ID NO: 54, the amino acid of (6) is the amino acid at the position 446 of SEQ ID NO: 54, the amino acid of (7) is the amino acid at the position 481 of SEQ ID NO: 54, and the amino acid of (8) is the amino acid at the position 482 of SEQ ID NO: 54.

The amino acid to be substituted is preferably the amino acid of (1) or (2). These amino acids have been, as shown in Examples mentioned below, confirmed to be extremely effective for imparting dehydrogenase activity by themselves. The mutant CHOs in which any these amino acids have been substituted exhibit much higher activity ratios (CHDH activity/CHO activity) in comparison with the enzyme before mutation.

The amino acid after substitution is not particularly limited. Examples of the amino acid after substitution include: glutamic acid, threonine, valine, methionine, and tryptophan for the amino acid of (1); proline, glutamic acid, arginine, alanine, and tryptophan for the amino acid of (2); aspartic acid, asparagine, glycine, tryptophan, and threonine for the amino acid of (3); lysine, tyrosine, proline, threonine, and glycine for the amino acid of (4); proline, glutamine, histidine, tyrosine, and phenylalanine for the amino acid of (5); methionine and tryptophan for the amino acid of (6); glycine, leucine, threonine, and alanine for the amino acid of (7); and cysteine, isoleucine, serine, and threonine for the amino acid of (8).

Specific examples of the mutant enzyme obtained by applying the above-mentioned mutation (mutant CHO obtained by applying the above-mentioned mutation to the *Streptomyces* sp.-derived CHO) are shown below.

Mutant enzyme L113E: SEQ ID NO: 2: the mutant of (1), and the amino acid after substitution is glutamic acid.

Mutant enzyme M362P: SEQ ID NO: 3: the mutant of (2), and the amino acid after substitution is proline.

Mutant enzyme M362E: SEQ ID NO: 4: the mutant of (2), and the amino acid after substitution is glutamic acid.

Mutant enzyme M362R: SEQ ID NO: 5: the mutant of (2), and the amino acid after substitution is arginine.

Mutant enzyme M362A: SEQ ID NO: 6: the mutant of (2), and the amino acid after substitution is alanine.

Mutant enzyme M362W: SEQ ID NO: 7: the mutant of (2), and the amino acid after substitution is tryptophan.

Of the amino acids of (1) to (8), two or more of the amino acids may be substituted. Preferred combinations of the amino acids to be substituted are listed below.

Combination of (2) and (4)
Combination of (2) and (6)
Combination of (2) and (7)
Combination of (2) and (8)

Specific examples of the mutant enzyme obtained by applying the above combinations (the mutant CHOs obtained by applying the above-mentioned combinations of mutation to the *Streptomyces* sp.-derived CHO) are shown below.

Mutant enzyme (M362P+L412Y): SEQ ID NO: 8: the combination of (2) and (4), and the amino acid after substitution of (2) is proline, and the amino acid after substitution of (4) is tyrosine.

Mutant enzyme (M362P+Y483M): SEQ ID NO: 9: the combination of (2) and (6), and the amino acid after substitution of (2) is proline, the amino acid after substitution of (6) is methionine.

Mutant enzyme (M362P+Y483W): SEQ ID NO: 10: the combination of (2) and (6), the amino acid after substitution of (2) is proline, and the amino acid after substitution of (6) is tryptophan.

Mutant enzyme (M362P+S518G): SEQ ID NO: 11: the combination of (2) and (7), the amino acid after substitution of (2) is proline, and the amino acid after substitution of (7) is glycine.

Mutant enzyme (M362P+S518L): SEQ ID NO: 12: the combination of (2) and (7), the amino acid after substitution of (2) is proline, and the amino acid after substitution of (7) is leucine.

Mutant enzyme (M362P+S518T): SEQ ID NO: 13: the combination of (2) and (7), the amino acid after substitution of (2) is proline, and the amino acid after substitution of (7) is threonine.

Mutant enzyme (M362P+S518A): SEQ ID NO: 14: the combination of (2) and (7), the amino acid after substitution of (2) is proline, and the amino acid after substitution of (7) is alanine.

Mutant enzyme (M362P+V519C): SEQ ID NO: 15: the combination of (2) and (8), the amino acid after substitution of (2) is proline, and the amino acid after substitution of (8) is cysteine.

Mutant enzyme (M362P+V519I): SEQ ID NO: 16: the combination of (2) and (8), the amino acid after substitution of (2) is proline, and the amino acid after substitution of (8) is isoleucine.

Mutant enzyme (M362P+V519S): SEQ ID NO: 17: the combination of (2) and (8), the amino acid after substitution of (2) is proline, and the amino acid after substitution of (8) is serine.

Mutant enzyme (M362P+V519T): SEQ ID NO: 18: the combination of (2) and (8), the amino acid after substitution of (2) is proline, and the amino acid after substitution of (8) is threonine.

In consideration of the experimental results shown in the below-described Examples (confirmation of the effect of the combinations of mutation), among the above-mentioned combinations, the combination of (2) and (6), the combination of (2) and (7), and the combination of (2) and (8) are preferred. The particularly preferred combination is the combination of (2) and (6). The mutant to which the combination of (2) and (6) had been applied (SEQ ID NO: 10) showed an extremely high activity ratio (CHDH activity/CHO activity).

Generally, when a part of an amino acid sequence of a certain protein is modified, the modified protein may have the equal function to that of the protein before the modification. That is to say, the modification of the amino acid sequence may not have a substantial effect on the function of the protein, so that the function of the protein may be maintained before and after the modification. When this technical common sense is considered, an enzyme that has a recognizable slight difference in the amino acid sequence (provided that the difference occurs in sites other than the sites in which the above (1) to (8) substitutions have been made) and has no substantially recognizable difference in the function can be regarded as an enzyme that is substantially the same as the above mutant CHO in comparison with the mutant CHO comprising the amino acid sequence in which one or more amino acids selected from the group consisting of the above (1) to (8) have been substituted with another amino acid. The term "slight difference in the amino acid sequence" as used herein typically means that the amino acid sequence is mutated (changed) by the deletion or substitution of one to several amino acids (the upper limit: e.g. 3, 5, 7, or 10 amino acids) constituting the amino acid sequence, or by the addition, insertion, or combination thereof, of one to several amino acids (the upper limit: e.g. 3, 5, 7, or 10 amino acids). The identity (%) of between the amino acid sequence in the "substantially the same enzyme" and the amino acid sequence of the above mutant CHO as a standard is preferably 90% or more, more preferably 95% or more, yet more preferably 98% or more, and most preferably 99% or more. In addition, the difference in the amino acid sequence may occur in a plurality of positions. The "slight difference in the amino acid sequences" is preferably generated by a conservative amino acid substitution.

(Nucleic Acid Coding for Mutant CHO, etc.)

The second aspect of the present invention provides a nucleic acid relating to the mutant CHO of the invention. That is, provided are a gene coding for the mutant CHO, a nucleic acid that can be used as a probe for identifying a nucleic acid coding for the mutant CHO, and a nucleic acid that can be used as a primer for amplifying or mutating a nucleic acid coding for the mutant CHO.

The gene coding for a mutant CHO is typically used in preparation of the mutant CHO. According to a genetic engineering procedure using the gene coding for a mutant CHO, a mutant CHO in a more homogeneous state can be obtained. Further, the method can be a preferable method also in the case of preparing a large amount of a mutant CHO. Note that uses of the gene coding for a mutant CHO are not limited to preparation of a mutant CHO. For example, the nucleic acid can also be used as a tool for an experiment intended for clarification of action mechanisms of a mutant CHO or a tool for designing or preparing a further mutant of an enzyme.

The "gene coding for a mutant CHO" herein refers to a nucleic acid capable of obtaining the mutant CHO when it is expressed, and includes, as a matter of course of a nucleic acid having a nucleotide sequence corresponding to the amino acid sequence of the mutant CHO, also a nucleic acid obtained by adding a sequence that does not code for an amino acid sequence to such a nucleic acid. Degeneracy of a codon is also considered.

Examples of the sequence of the gene coding for a mutant CHO are shown in the SEQ ID NOs: 20 to 36. These sequences are the genes coding for the mutant CHO treated with specific amino acid substitution to Streptomyces sp.-derived CHO. The amino acid substitutions in these sequences are as follows.

SEQ ID NO: 20: L113E
SEQ ID NO: 21: M362P
SEQ ID NO: 22: M362E
SEQ ID NO: 23: M362R
SEQ ID NO: 24: M362A
SEQ ID NO: 25: M362W
SEQ ID NO: 26: M362P and L412Y
SEQ ID NO: 27: M362P and Y483M
SEQ ID NO: 28: M362P and Y483W
SEQ ID NO: 29: M362P and S518G
SEQ ID NO: 30: M362P and S518L
SEQ ID NO: 31: M362P and S518T
SEQ ID NO: 32: M362P and S518A
SEQ ID NO: 33: M362P and V519C
SEQ ID NO: 34: M362P and V519I
SEQ ID NO: 35: M362P and V519S
SEQ ID NO: 36: M362P and V519T The nucleic acid of the present invention can be prepared in an isolated state by use of a standard genetic engineering technique, molecular biological technique, biochemical technique, and the like in reference to the present specification or the sequence information disclosed in the appended sequence listing.

Another embodiment of the present invention provides a nucleic acid different in a nucleotide sequence in a part (hereinafter also referred to as a "homologous nucleic acid", and a nucleotide sequence defining a homologous nucleic acid is also referred to as a "homologous nucleotide sequence") as compared to the nucleotide sequence of the gene coding for the mutant CHO of the invention, although functions of a protein coded by the nucleic acid are equal. An example of the homologous nucleic acid includes a DNA composed of a nucleotide sequence containing substitution, deletion, insertion, addition or inversion of 1 to several nucleotides on the basis of the nucleotide sequence of the nucleic acid coding for the mutant CHO of the present invention and coding for a protein having enzyme activity characteristic to the mutant CHO (i.e. CHDH activity). Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

Such a homologous nucleic acid as described above can be obtained by, for example, a restriction enzyme treatment, a treatment with exonuclease, DNA ligase, etc., and introduction of mutation by a site-directed mutagenesis method (Molecular Cloning, Third Edition, Chapter 13, Cold Spring Harbor Laboratory Press, New York), and a random mutagenesis method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having the complementary nucleotide sequence to the nucleotide sequence of the gene coding for the mutant CHO of the invention. Another embodiment of the present invention provides a nucleic acid having a nucleotide sequence with an identity of at least about 60%, 70%, 80%, 90%, 95%, 99%, or 99.9% to the nucleotide sequence of the gene coding for the mutant CHO of the invention or the complementary nucleotide sequence Another embodiment of the present invention relates to a nucleic acid having a nucleotide sequence hybridizing to the complementary nucleotide sequence to the nucleotide sequence of the gene coding for the mutant CHO of the invention or its homologous nucleotide sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 µg/ml of denatured salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 µg/ml of denatured salmon sperm DNA, and a 50 mM phosphate buffer (pH 7.5) as a hybridization liquid.

Another embodiment of the present invention provides a nucleic acid (nucleic acid fragment) having a part of the nucleotide sequence of the gene coding for the mutant CHO of the invention or the complementary nucleotide sequence. Such a nucleic acid fragment can be used in detection, identification, and/or amplification of a nucleic acid having the nucleotide sequence of the gene coding for the muntant CHO of the present invention. For example, the nucleic acid fragment is designed so as to at least contain a part being hybridized to a sequential nucleotide moiety (for example, about 10 to about 100 nucleotides length, preferably about 20 to about 100 bases length, more preferably about 30 to about 100 bases length) in the nucleotide sequence of the gene coding for the mutant CHO of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a mutant CHO). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

For the host cell, microorganisms such as *Escherichia coli* and budding yeasts (*Saccharomyces cerevisiae*) are preferably used from the viewpoint of easiness of handling, and host cells capable of duplicating a recombinant DNA and expressing a gene of a modified enzyme can be used. Examples of *Escherichia coli* include *Escherichia coli* BL21 (DE3)pLysS in the case of using a T7 promoter, and *Escherichia coli* JM109 in other cases. Examples of budding yeasts include budding yeast SHY2, AH22, or INVSc1 (Invitrogen Ltd.).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, the electroporation method (Potter, H. et al., Proc. Natl. Acad. Sci. U.S.A. 81, 7161-7165 (1984)), and the lipofectin method (Feigner, P. L. et al., Proc. Natl. Acad. Sci. U.S.A. 84, 7413-7417 (1984)). Note that the microorganism of the present invention can be used in producing the mutant CHO of the present invention (see the section of the preparation method of mutant enzyme described later).

(Use of Mutant CHO)

The third aspect of the present invention relates to a use of a mutant CHO. In this aspect, a cholesterol measurement method using a mutant CHO is provided. In the cholesterol measurement method of the present invention, the amount of cholesterol in a sample is measured using oxidation-reduction reaction by the present enzyme. The present invention is used for, for example, measuring the amount of cholesterol in the blood and food.

The present invention also provides a cholesterol measurement reagent containing the present enzyme. The reagent is used in the above-mentioned cholesterol measurement method of the present invention.

The present invention further provides a kit for conducting the cholesterol measurement method of the present invention (cholesterol measurement kit). The kit of the present invention contains optional elements such as a reaction reagent, a buffer, and a cholesterol standard solution besides the cholesterol measurement reagent containing the present enzyme. In addition, an instruction is usually attached to the cholesterol measurement kit of the present invention.

(Preparation Method of Mutant CHO)

A further aspect of the present invention relates to a preparation method of a modified enzyme. In one embodiment of the preparation method of a modified enzyme of the present invention, the mutant CHO that the present inventors succeeded in obtaining is prepared in a genetic engineering technique. In the case of this embodiment, a nucleic acid coding for any one of the amino acid sequences of SEQ ID NOs: 2 to 18, is prepared (step (I)). Herein, "a nucleic acid coding for a specific amino acid sequence" is a nucleic acid capable of obtaining a polypeptide having the amino acid sequence in the case of being expressed, and as a matter of course of a nucleic acid having a nucleotide sequence corresponding to the amino acid sequence, may be a nucleic acid added with an extra sequence (may be a sequence coding for an amino acid sequence or a sequence not coding for an amino acid sequence). Degeneracy of a codon is also considered. "A nucleic acid coding for any one of the amino acid sequences of SEQ ID NOs: 2 to 18" can be prepared into a state of being isolated by using a standard genetic engineering technique, molecular biological technique, biochemical technique, and the like in reference to sequence information disclosed in the present specification or the appended sequence listing. Herein, all of the amino acid sequences of SEQ ID NOs: 2 to 18 are obtained by mutation to the amino acid sequence of the *Streptmyces* sp.-derived CHO. Therefore, a nucleic acid (gene) coding for any one of the amino acid sequences of SEQ ID NO: 2 to 18 can be obtained also by adding necessary mutation to the gene coding for the *Streptmyces* sp.-derived CHO (SEQ ID NO: 19). A large number of methods for site-directed mutagenesis have been known in the present technical field (for example, see Molecular Cloning, Third Edition, Cold Spring Harbor Laboratory Press, New York), and among those methods, a suitable method can be selected to be used. A method of saturation mutagenesis can be adopted as the method of site-directed mutagenesis. The method of saturation mutagenesis is a "semi-rational, semi-random" technique of assuming a position which relates to a desired function based on a conformation of a protein and introducing amino acid saturation (J. Mol. Biol. 331,585-592 (2003)). For example, use of a kit such as KOD-Plus-Mutagenesis Kit (TOYOBO CO., LTD.), Quick change (Stratagene Corporation) and Overlap extension PCR (Nucleic Acid Res. 16, 7351-7367 (1988)) makes it possible to introduce position specific amino acid saturation. A Taq polymerase and the like can be used for a DNA polymerase used in PCR. Provided that a DNA polymerase having high precision such as KOD-PLUS-(TOYOBO CO., LTD.) or Pfu turbo (Stratagene Corporation) is preferably used.

Following the step (I), the prepared nucleic acid is expressed (step (II)). For example, firstly, an expression vector inserted with the above described nucleic acid is prepared and a host cell is transformed using this constructed vector. The "expression vector" refers to a vector that can introduce a nucleic acid inserted therein into a desired cell (host cell) and is capable of being expressed in the cell. The expression vector generally contains a promoter sequence that is necessary for expression of an inserted nucleic acid, an enhancer sequence that promotes expression, and the like. An expression vector containing a selection marker can also be used. When such an expression vector is used, presence or absence (and its degree) of the expression vector can be confirmed by using a selection marker.

Then, a transformant is cultured under the condition of producing a modified enzyme that is an expressed product. Culture of the transformant may follow a general method. An assimilable carbon compound may be used as a carbon source used for a medium, and examples such as glucose, sucrose, lactose, maltose, molasses, and pyruvic acid are used. An available nitrogen compound may be used as a nitrogen source, and examples such as peptone, meat extract, yeast extract, casein hydrolysate, and soybean bran alkali extract are used. Other than those substances, phosphate, carbonate, sulfate, salts of magnesium, calcium, potassium, iron, manganese and zinc, specific amino acids, specific vitamins, and the like are used according to necessity.

On the other hand, a culture temperature can be set within the range from 30 to 40° C. (preferably at around 37° C.). A culture time can be set by considering growing characteristics of a transformant to be cultured and production characteristics of a mutant-type enzyme. A pH of a medium is set within the range wherein a transformant grows and an enzyme is produced. The pH of a medium is preferably set at about 6.0 to 9.0 (preferably at around pH 7.0).

Subsequently, the expressed product (mutant enzyme) is collecte (step (III)). A culture liquid containing fungas bodies after culture may be used as an enzyme solution directly or after undergoing condensation, removal of impurities, or the like, but the expressed product is generally once collected from the culture liquid or fungas bodies. When the expressed product is a secretion type protein, it can be collected from the culture liquid, and in other cases, the expressed product can be collected from cells. In the case of collecting from the culture liquid, for example, an undissolved substance is removed by filtration and centrifugation on a culture supernatant, and then, a purified product of a modified enzyme can be obtained by separation and purification in combination of vacuum concentration, membrane concentration, salting out using ammonium sulfate or sodium sulfate, fractional precipitation by methanol, ethanol, or acetone, dialysis, heating treatment, isoelectric treatment, various kinds of chromatography such as gel filtration, adsorption chromatography, ion exchange chromatography, and affinity chromatography (for example, gel filtration with Sephadex gel (GE Healthcare Life Sciences), etc., DEAE sepharose CL-6B (GE Healthcare Life Sciences), octyl sepharose CL-6B (GE Healthcare Life Sciences), CM sepharose CL-6B (GE Healthcare Life Sciences)). On the other hand, in the case of collecting the expressed product from cells, a culture liquid is subjected to filtration, centrifugation, or the like, to thus obtain the cells, then the cells are crushed by a mechanical method such as a pressure treatment and an ultrasonic treatment, or an enzymatic method with a lysozyme or the like, thereafter carrying out separation and purification in the same manner as described above, and a purified product of a mutant enzyme can be thus obtained.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

Generally, genetic expression and collection of the expressed product (modified enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al. Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

EXAMPLES

With the aim of creating a highly practical enzyme for measuring cholesterol, the following study was carried out under the strategy of imparting dehydrogenase activity to cholesterol oxidase.

A. Identification of Mutation Site

Based on the steric structure information (protein data bank (PDB): 1MXT) of a known cholesterol oxidase (*Streptomyces* sp. SA-COO), the steric structure of *Streptomyces* sp.-derived cholesterol oxidase (CHO) (SEQ ID NO: 1) was predicted, and the mutation sites were selected. The mutation sites were selected around the substrate-binding site (18 points), and around the active center (9 points).

B. Selection of Mutation Site Effective for Imparting Dehydrogenase Activity

Of the mutation sites identified in A, those effective for imparting dehydrogenase activity were selected using a random library.

<Method>

The mutation site effective for imparting dehydrogenase activity was selected by the following method.

1. Random mutagenesis was introduced by a PCR method (reaction liquid: 25 μL/tube). The template was pC4-CHOA1 No. 1 (plasmid: pColdIV, insertion gene: cho gene (BspHI-HindIII)).
2. A restriction enzyme DpnI (1.5 μL/tube) was added to the PCR reaction liquid (25 μL/tube), and treated (37° C., 1 h).
3. Ligation treatment (16° C., 2 h) was carried out using a DpnI treatment liquid (2 μL).
4. *E. coli* DH5a was transformed using a ligation reaction liquid (10 μL/tube).
5. SOC (100 μL/tube) was added, and subjected to rehabilitation culture (37° C., 1h).
6. The total amount was applied to an LB+Amp (100 μg/mL) plate, and cultured (37° C., O/N).
7. Plasmid was extracted using QIA Prep (Qiagen).
8. *E. coli* BL21 (pGKJE-8) was transformed using the extracted plasmid (4 μL).
9. SOC (1 mL/tube) was added, and subjected to rehabilitation culture (37° C., 1 h).
10. The product was applied to an LB+Amp (100 μg/mL)+Cm (20 μg/mL) plate, and cultured (37° C., O/N).
11. After preculture in an LB Broth (Invitrogen Ltd.), main culture was carried out in Teriffic Broth (Invitrogen Ltd.).
12. After main culture, the cell bodies were collected, and the enzyme was extracted using B-per (TaKaRa Bio Inc.).
13. The activity was confirmed using the CHO activity measurement method and CHDH activity measurement method.
14. The activity ratio (CHDH/CHO) was compared.

<CHO Activity Measurement Method>

The enzyme extracted from cell bodies (or the enzyme extracted from cell bodies, and purified) was diluted 1 to 1,000 times with a diluting buffer (50 mM PIPES, 0.1% Triton X-100, and 0.1% BSA (pH 7.0)). 0.02 mL of the thus-prepared sample was mixed with 0.2 mL of reaction liquid (a mixture of 25.5 mL of 0.1 M phosphate buffer (pH 7.0), 2 mL of substrate solution (5.3% cholesterol solution (w/v)), 0.5 mL of 1.76 g/dL 4-A.A solution, 1 mL of 5 g/dL phenol solution, and 1 mL of 250 U/mL PO-3 (PO "Amano" 3) solution), allowed to react at 37° C. for 0.5 hours, and the absorbance at 500 nm was measured. Under these measurement conditions, the enzyme activity (U) was calculated, setting the amount of enzyme forming 1 μmol of $H_2O_2$ in 1 minute as 1 U.

<CHDH Activity Measurement Method>

The enzyme extracted from cell bodies (or the enzyme extracted from cell bodies and purified) was diluted 1 to 1,000 times with a diluting buffer (50 mM PIPES, 0.1% Triton X-100, and 0.1% BSA (pH 7.0)). 0.02 mL of the thus-prepared sample was mixed with 0.2 mL of reaction liquid (a mixture of 25 mL of 0.1 M phosphate buffer (pH 7.0), 2 mL of substrate solution (5.3% cholesterol solution (w/v)), 2 mL of 3 mmol/L PMS solution, and 1 mL of 6.6 mmol/L NTB solution), allowed to react at 37° C. for 0.5 hours, and the absorbance at 570 nm was measured. Under these measurement conditions, the enzyme activity (U) was calculated, setting the amount of enzyme forming 0.5 μmol of diformazan dye in 1 minute as 1 U.

<Result>

FIG. 4 shows the result (a part of the experimental data; the data of M402 and L412 are not shown). On the basis of the activity ratio (Δ570 nm/Δ500 nm), five mutation sites around the substrate-binding site (L113, M362, M402, L412, and D468) and three mutation sites around the active center (Y483, S518, and V519) were selected. The Δ570 is the difference between the OD value of the sample at the completion of the reaction for 0.5 hours in the CHDH activity measurement method and the OD value of the blank, and the Δ500 is the difference between the OD value of the sample at the completion of the reaction for 0.5 hours in the CHO activity measurement method and the OD value of the blank.

C. Identification of Amino Acid After Substitution Effective for Imparting Dehydrogenase Activity For the mutation sites selected in B, the amino acids effective for imparting dehydrogenase activity were studied using saturation library.

<Method>

The amino acids effective for imparting dehydrogenase activity were identified by the following method. The reaction conditions and culture conditions are the same as those in the method of B.

1. Saturation mutagenesis was introduced by a PCR method (reaction liquid: 25 μL/tube). The template was pC4-CHOA1 No. 1 (plasmid: pColdIV, insertion gene: cho gene (BspHI-HindIII)).
2. A restriction enzyme DpnI (1.5 μL/tube) was added to the PCR reaction liquid (25 μL/tube), and treated (37° C., 1 h).
3. Ligation treatment (16° C., 2 h) was carried out using a DpnI treatment liquid (2 μL).
4. *E. coli* BL21 (pGKJE-8) was transformed using a ligation reaction liquid (10 μL/tube).
5. The product was applied to an LB+Amp (100 μg/mL)+Cm (20 μg/mL) plate, and cultured (37° C., O/N).
6. After preculture in an LB Broth (Invitrogen Ltd.), and main culture was carried out in Teriffic Broth (Invitrogen Ltd.).
7. After main culture, the cell bodies were collected, and the enzyme was extracted using B-per (TaKaRa Bio Inc.).
8. The activity was confirmed using the CHO activity measurement method and CHDH activity measurement method.
9. The activity ratio (CHDH/CHO) was compared.

<Result>

The result is shown in FIG. 5. For each mutation site, as mentioned below, effective amino acids after substitution were identified. For the mutation sites (Y483, S518, and V519) around the active center, the effective amino acids after substitution were identified in consideration of the effect of combination with other mutation sites (FIG. 7). The activity ratio (CHDH/CHO) in FIGS. 5 to 7 were calculated in terms of U/mL for CHO and CHDH from the difference of OD values of the sample at the points of 20 minutes and 30 minutes (completion of reaction) during the reaction for 0.5 hours in the activity measurement method, and represented by the ratio.

L113: glutamic acid, threonine, valine, methionine, tryptophan

M362: proline, glutamic acid, arginine, alanine, tryptophan

M402: asparatic acid, asparagine, glycine, tryptophan, threonine

L412: lysine, tyrosine, proline, threonine, glycine

D468: proline, glutamine, histidine, tyrosine, phenylalanine

Y483: methionine, tryptophan

S518: glycine, leucine, threonine, alanine

V519: cysteine, isoleucine, serine, threonine

D. Effect of Combining Mutation Sites

The effect of combining mutation sites was studied.

<Method>

The effect of combination of the mutation sites was studied by the following method. The reaction conditions and culture conditions are the same as those in the method of B.

1. Saturation mutagenesis was introduced by a PCR method (reaction liquid: 25 µL/tube). The template was pC4-CHOA1 No. 1-M362P (plasmid: pColdIV, insertion gene: cho gene containing M362P mutation (BspHI-HindIII)).

2. A restriction enzyme DpnI (1.5 µL/tube) was added to the PCR reaction liquid (25 µL/tube), and treated (37° C., 1 h).

3. Ligation treatment (16° C., 2 h) was carried out using a DpnI treatment liquid (2 µL).

4. E. coli BL21 (pGKJE-8) was transformed using a ligation reaction liquid (10 µL/tube).

5. The product was applied to an LB+Amp (100 µg/mL)+ Cm (20 µg/mL) plate, and cultured (37° C., O/N).

6. After preculture in an LB Broth (Invitrogen Ltd.), and main culture was carried out in Teriffic Broth (Invitrogen Ltd.). 7. After main culture, the cell bodies were collected, and the enzyme was extracted using B-per (TaKaRa Bio Inc.).

8. The activity was confirmed using the CHO activity measurement method and CHDH activity measurement method.

9. The activity ratio (CHDH/CHO) was compared.

<Result>

Figure 6:
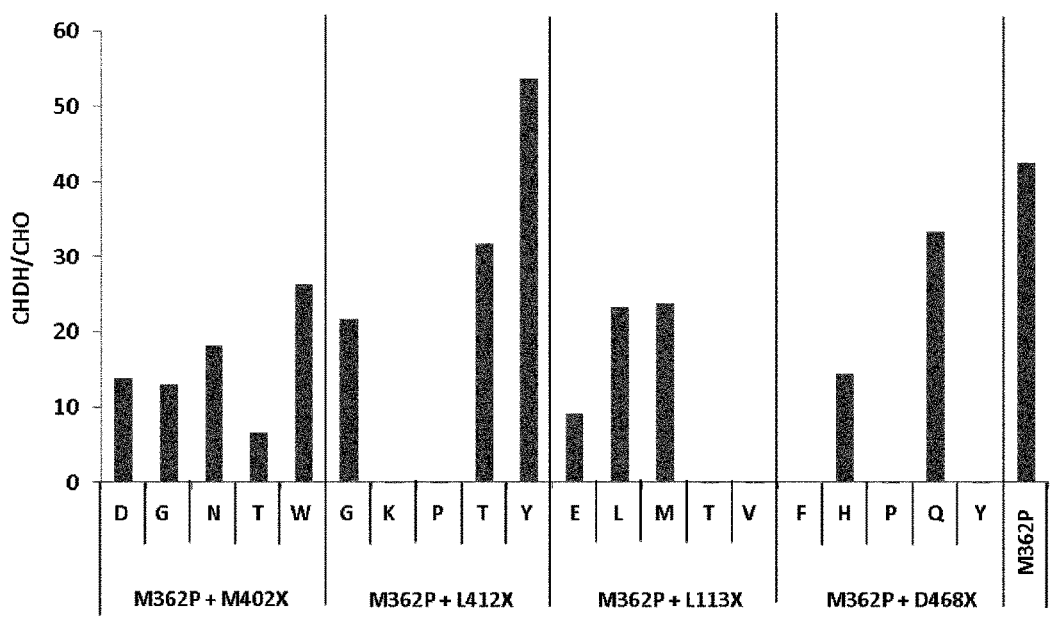
FIG. 6 shows the evaluation of double variants. The effect of the combination of the mutagenesis M362P and other mutagenesis (L113E, L113T, L113V, L113M, L113L, L412K, L412Y, L412P, L412T, L412G, M402D, M402N, M402G, M402W, M402T, D468P, D468Q, D468H, D468Y, and D468F as mutagenesis around the substrate-binding site) was studied.

The results are shown in FIGS. 6 and 7. As a result of the combination of the mutation sites, it was confirmed that imparting of dehydrogenase activity was improved. The combinations of mutations having higher activity ratio (CHDH/CHO) than M362P (alone) are shown below. Among these combinations, the combination 1 (M362P+L412Y) showed a particularly high activity ratio. For each combination, the amino acid sequences of mutant enzymes are shown in SEQ ID NO: 8 (combination 1), SEQ ID NO: 9 (combination 2), SEQ ID NO: 10 (combination 3), SEQ ID NO: 11 (combination 4), SEQ ID NO: 12 (combination 5), SEQ ID NO: 13 (combination 6), SEQ ID NO: 14 (combination 7), SEQ ID NO: 15 (combination 8), SEQ ID NO: 16 (combination 9), SEQ ID NO: 17 (combination 10), and SEQ ID NO: 18 (combination 11).

Combination 1: M362P+L412Y
Combination 2: M362P+Y483M
Combination 3: M362P+Y483W
Combination 4: M362P+S518G
Combination 5: M362P+S518L
Combination 6: M362P+S518T
Combination 7: M362P+S518A
Combination 8: M362P+V519C
Combination 9: M362P+V519I
Combination 10: M362P+V519S
Combination 11: M362P+V519T E. Evaluation of Activity of Mutant Enzyme The mutant enzyme having dehydrogenase activity was purified, and the specific activity was confirmed.

<Method>

The specific activity of the mutant enzymes having dehydrogenase activity (M362P, M362P+L412Y, M362P+Y483W, M362P+S518T, and M362P+V519C) was determined by the following method. For comparison, specific activities of a wild type enzyme and a previously reported mutant enzyme (V228A) were also calculated.

1. The Escherichia coli after transformation was cultured (preculture and main culture) for each mutant enzyme. The culture conditions were the same as those in the abovementioned experiments.

2. The cell bodies were collected from the culture solution, and subjected to purification (collection of cell bodies→homogenation of cell bodies (beads homogenation)→collection of supernatant→flocculation treatment→column purification (DEAE Sepharose, Buthyl-S Sepharose)→desaltation and concentration).

3. The activity (CHO and CHDH) and protein concentration were measured, and specific activity was calculated.

4. CHDH/CHO (specific activity) was compared.

<Result>

The result is shown in FIG. 8. It was confirmed that each of the mutant enzymes had higher dehydrogenase activity than the wild type. Surprisingly, even the single mutation (M362P) showed about $1.9 \times 10^6$ times higher activity ratio (CHDH activity/CHO activity) than the wild type. The degree of imparting dehydrogenase activity was far higher than the mutant enzyme (V228A: a mutant in which the amino acid residue V228 corresponding to V191 has been substituted with alanine) corresponding to the known mutation (V191A reported in Katsuhiro Kojima et al., Journal of molecular catalysis B: Enzymatic 88 (2013) 41-46). In addition, as a result of the combination of mutations, the activity ratio (CHDH activity/CHO activity) became about 2 to 20 times that by the single mutation. The activity value U/mL in FIG. 8 was calculated from the difference of the OD value at the time points of 3 minutes and 5 minutes in the reaction for 0.5 hour in the activity measurement method.

F. Comparison of Structures of Streptomyces sp.-Derived CHO and Brevibacterium Sterolicum-Derived CHO The structures of Streptomyces sp.-derived CHO (SEQ ID NO: 1) and Brevibacterium sterolicum-derived CHO (SEQ ID NO: 54), which had been used for the preparation of the mutant enzymes, were superposed by FAD using a computer software (Molecule Operating Environment (Chemical Computing Group)). These structures showed a high identity, and the amino acid residues generally accorded. FIG. 9 shows the amino acid residues of Brevibacterium CHO corresponding to the amino acid residues which had been found to be involved in imparting dehydrogenase activity to Streptomyces sp.-derived CHO (L113, M362, M402, L412, D468, Y483, S518, and V519). It is naturally expected that the mutation of these amino acid residues (P76 corresponding to L113, M325 corresponding to M362, L365 corresponding to M402, L375 corresponding to L412, D431 corresponding to D468, Y446 corresponding to Y483, N481 corresponding to S518, and V482 corresponding to V519) will impart dehydrogenase activity to Brevibacterium sterolicum-derived CHO.

INDUSTRIAL APPLICABILITY

The mutant CHO of the present invention is useful for the detection and quantification of cholesterol in a sample. The mutant CHO of the present invention has the advantage of CHO (unnecessity of addition of coenzyme for measurement) and the advantage of CHDH (imperviousness to influence of dissolved oxygen), and the use value is high. Since the mutant CHO of the present invention includes a coenzyme FAD, it does not require the addition of a coenzyme (NAD for CHDH), and allows simple and low-cost measurement.

This invention is not limited at all by the above-mentioned embodiments for carrying out the invention and the explanations in the Examples. Various modified embodiments are also encompassed in this invention within a scope that does not deviate from the recitation of the claims and can be easily conceived by a person skilled in the art. All of the contents of the articles, patent publications and patent gazettes that are clearly indicated in the present specification are incorporated herein by reference.

The invention claimed is:

1. A mutant enzyme consisting of an amino acid sequence that is 95% identical to SEQ ID NO: 1 and in which one or two or more of the amino acid(s) selected from the group consisting of the following (1) to (8) has/have been substituted by another amino acid in the amino acid sequence of a microorganism-derived cholesterol oxidase, the mutant enzyme having higher cholesterol dehydrogenase activity to cholesterol oxidase activity (CHDH activity/CHO activity) in comparison with the microorganism-derived cholesterol oxidase:

(1) an amino acid corresponding to the amino acid at the position 113 of the amino acid sequence of SEQ ID NO: 1;

(2) an amino acid corresponding to the amino acid at the position 362 of the amino acid sequence of SEQ ID NO: 1;

(3) an amino acid corresponding to the amino acid at the position 402 of the amino acid sequence of SEQ ID NO: 1;

(4) an amino acid corresponding to the amino acid at the position 412 of the amino acid sequence of SEQ ID NO: 1;

(5) an amino acid corresponding to the amino acid at the position 468 of the amino acid sequence of SEQ ID NO: 1;

(6) an amino acid corresponding to the amino acid at the position 483 of the amino acid sequence of SEQ ID NO: 1;

(7) an amino acid corresponding to the amino acid at the position 518 of the amino acid sequence of SEQ ID NO: 1; and (8) an amino acid corresponding to the amino acid at the position 519 of the amino acid sequence of SEQ ID NO: 1.

2. The mutant enzyme according to claim 1, wherein the amino acid sequence of the microorganism-derived cholesterol oxidase is a sequence showing an identity of 65% or more with the amino acid sequence of SEQ ID NO: 1.

3. The mutant enzyme according to claim 1, wherein the amino acid to be substituted is the amino acid of (2), and the amino acid after substitution is proline.

4. The mutant enzyme according to claim 1, wherein the amino acid to be substituted is the combination of the amino acids of (2) and (4), the combination of the amino acids of (2) and (6), the combination of the amino acids of (2) and (7), or the combination of the amino acids of (2) and (8).

5. The mutant enzyme according to claim 4, wherein the amino acid after substitution is proline for the amino acid of (2), tyrosine for the amino acid of (4), methionine or tryptophan for the amino acid of (6), glycine, leucine, threonine, or alanine for the amino acid of (7), and cysteine, isoleucine, serine, or threonine for the amino acid of (8).

6. The mutant enzyme according to claim 1, which consists of any of the amino acid sequences of SEQ ID NOs: 2 to 18.

7. A gene coding for the mutant enzyme according to claim 1.

8. The gene according to claim 7, comprising the base sequence of any of SEQ ID NOs: 20 to 36.

9. A recombinant DNA comprising the gene according to claim 7.

10. A microorganism having the recombinant DNA according to claim 9.

11. A method for measuring cholesterol, comprising measuring cholesterol in a sample using the mutant enzyme according to claim 1.

12. An enzyme preparation comprising the mutant enzyme according to claim 1.

* * * * *

SEQUENCE LISTING

<160> NUMBER OF SEQ ID NOS: 56

<210> SEQ ID NO 1
<211> LENGTH: 546
<212> TYPE: PRT
<213> ORGANISM: Streptomyces sp.

<400> SEQUENCE: 1

```
Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
                20                  25                  30

Arg Ala Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
    50                  55                      60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
    130                 135                 140

Val Gly Arg Gly Val Gly Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
                180                 185                 190

Arg Val Asn His Ile Asp Thr Lys Trp Phe Glu Asp Thr Glu Trp Tyr
            195                 200                 205

Lys Phe Ala Arg Val Ser Arg Glu Gln Ala Gly Lys Ala Gly Leu Gly
    210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
                260                 265                 270

Ala Leu Gly Thr Gly Lys Val Thr Ile Gln Thr Leu His Gln Val Lys
            275                 280                 285
```

```
Thr Ile Arg Gln Thr Lys Asp Gly Gly Tyr Ala Leu Thr Val Glu Gln
    290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Met Thr Ala Arg Ala Asn His
        355                 360                 365

Met Trp Asn Pro Thr Gly Ala His Gln Ser Ser Ile Pro Ala Leu Gly
    370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
        435                 440                 445

Ala Ala Lys Ala Leu Phe Asp Arg Ile Asn Lys Ala Asn Gly Thr Ile
    450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Ser Val Gly Val Asn Pro Phe Val Thr Ile Thr
        515                 520                 525

Ala Leu Ala Glu Arg Asn Val Glu Arg Ile Ile Lys Gln Asp Val Thr
    530                 535                 540

Ala Ser
545

<210> SEQ ID NO 2
<211> LENGTH: 546
<212> TYPE: PRT
<213> ORGANISM: Artificial Sequence
<220> FEATURE:
<223> OTHER INFORMATION: Mutant L113E

<400> SEQUENCE: 2

Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
            20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
    50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95
```

```
Asn Pro Asp Lys Arg Ser Ser Trp Phe Lys Asn Arg Thr Glu Ala Pro
            100                 105                 110
Glu Gly Ser Phe Leu Trp Leu Asp Val Val Asn Arg Asn Ile Asp Pro
        115                 120                 125
Tyr Ala Gly Val Leu Asp Arg Val Asn Tyr Asp Gln Met Ser Val Tyr
    130                 135                 140
Val Gly Arg Gly Val Gly Gly Ser Leu Val Asn Gly Gly Met Ala
145                 150                 155                 160
Val Glu Pro Lys Arg Ser Tyr Phe Glu Glu Ile Leu Pro Arg Val Asp
                165                 170                 175
Ser Ser Glu Met Tyr Asp Arg Tyr Phe Pro Arg Ala Asn Ser Met Leu
            180                 185                 190
Arg Val Asn His Ile Asp Thr Lys Trp Phe Glu Asp Thr Glu Trp Tyr
        195                 200                 205
Lys Phe Ala Arg Val Ser Arg Glu Gln Ala Gly Lys Ala Gly Leu Gly
    210                 215                 220
Thr Val Phe Val Pro Asn Val Tyr Asp Phe Gly Tyr Met Gln Arg Glu
225                 230                 235                 240
Ala Ala Gly Glu Val Pro Lys Ser Ala Leu Ala Thr Glu Val Ile Tyr
                245                 250                 255
Gly Asn Asn His Gly Lys Gln Ser Leu Asp Lys Thr Tyr Leu Ala Ala
            260                 265                 270
Ala Leu Gly Thr Gly Lys Val Thr Ile Gln Thr Leu His Gln Val Lys
        275                 280                 285
Thr Ile Arg Gln Thr Lys Asp Gly Gly Tyr Ala Leu Thr Val Glu Gln
    290                 295                 300
Lys Asp Thr Asp Gly Lys Leu Leu Ala Thr Lys Glu Ile Ser Cys Arg
305                 310                 315                 320
Tyr Leu Phe Leu Gly Ala Gly Ser Leu Gly Ser Thr Glu Leu Leu Val
                325                 330                 335
Arg Ala Arg Asp Thr Gly Thr Leu Pro Asn Leu Asn Ser Glu Val Gly
            340                 345                 350
Ala Gly Trp Gly Pro Asn Gly Asn Ile Met Thr Ala Arg Ala Asn His
        355                 360                 365
Met Trp Asn Pro Thr Gly Ala His Gln Ser Ser Ile Pro Ala Leu Gly
    370                 375                 380
Ile Asp Ala Trp Asp Asn Ser Asp Ser Ser Val Phe Ala Glu Ile Ala
385                 390                 395                 400
Pro Met Pro Ala Gly Leu Glu Thr Trp Val Ser Leu Tyr Leu Ala Ile
                405                 410                 415
Thr Lys Asn Pro Gln Arg Gly Thr Phe Val Tyr Asp Ala Ala Thr Asp
            420                 425                 430
Arg Ala Lys Leu Asn Trp Thr Arg Asp Gln Asn Ala Pro Ala Val Asn
        435                 440                 445
Ala Ala Lys Ala Leu Phe Asp Arg Ile Asn Lys Ala Asn Gly Thr Ile
    450                 455                 460
Tyr Arg Tyr Asp Leu Phe Gly Thr Gln Leu Lys Ala Phe Ala Asp Asp
465                 470                 475                 480
Phe Cys Tyr His Pro Leu Gly Gly Cys Val Leu Gly Lys Ala Thr Asp
                485                 490                 495
Asp Tyr Gly Arg Val Ala Gly Tyr Lys Asn Leu Tyr Val Thr Asp Gly
            500                 505                 510
Ser Leu Ile Pro Gly Ser Val Gly Val Asn Pro Phe Val Thr Ile Thr
```

```
                     515                 520                 525
Ala Leu Ala Glu Arg Asn Val Glu Arg Ile Ile Lys Gln Asp Val Thr
            530                 535                 540

Ala Ser
545

<210> SEQ ID NO 3
<211> LENGTH: 546
<212> TYPE: PRT
<213> ORGANISM: Artificial Sequence
<220> FEATURE:
<223> OTHER INFORMATION: Mutant M362P

<400> SEQUENCE: 3

Met Thr Ala Gln Gln His Leu Ser Arg Arg Met Leu Gly Met Ala
1               5                   10                  15

Ala Phe Gly Ala Ala Ala Leu Ala Gly Gly Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
130                 135                 140

Val Gly Arg Gly Val Gly Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
            195                 200                 205

Lys Phe Ala Arg Val Ser Arg Glu Gln Ala Gly Lys Ala Gly Leu Gly
210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
            275                 280                 285

Thr Ile Arg Gln Thr Lys Asp Gly Gly Tyr Ala Leu Thr Val Glu Gln
            290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
```

```
                    325                 330                 335
Arg Ala Arg Asp Thr Gly Thr Leu Pro Asn Leu Asn Ser Glu Val Gly
            340                 345                 350
Ala Gly Trp Gly Pro Asn Gly Asn Ile Pro Thr Ala Arg Ala Asn His
            355                 360                 365
Met Trp Asn Pro Thr Gly Ala His Gln Ser Ser Ile Pro Ala Leu Gly
            370                 375                 380
Ile Asp Ala Trp Asp Asn Ser Asp Ser Ser Val Phe Ala Glu Ile Ala
385                 390                 395                 400
Pro Met Pro Ala Gly Leu Glu Thr Trp Val Ser Leu Tyr Leu Ala Ile
            405                 410                 415
Thr Lys Asn Pro Gln Arg Gly Thr Phe Val Tyr Asp Ala Ala Thr Asp
            420                 425                 430
Arg Ala Lys Leu Asn Trp Thr Arg Asp Gln Asn Ala Pro Ala Val Asn
            435                 440                 445
Ala Ala Lys Ala Leu Phe Asp Arg Ile Asn Lys Ala Asn Gly Thr Ile
            450                 455                 460
Tyr Arg Tyr Asp Leu Phe Gly Thr Gln Leu Lys Ala Phe Ala Asp Asp
465                 470                 475                 480
Phe Cys Tyr His Pro Leu Gly Gly Cys Val Leu Gly Lys Ala Thr Asp
            485                 490                 495
Asp Tyr Gly Arg Val Ala Gly Tyr Lys Asn Leu Tyr Val Thr Asp Gly
            500                 505                 510
Ser Leu Ile Pro Gly Ser Val Gly Val Asn Pro Phe Val Thr Ile Thr
            515                 520                 525
Ala Leu Ala Glu Arg Asn Val Glu Arg Ile Ile Lys Gln Asp Val Thr
            530                 535                 540
Ala Ser
545

<210> SEQ ID NO 4
<211> LENGTH: 546
<212> TYPE: PRT
<213> ORGANISM: Artificial Sequence
<220> FEATURE:
<223> OTHER INFORMATION: Mutant M362E

<400> SEQUENCE: 4

Met Thr Ala Gln Gln His Leu Ser Arg Arg Arg Met Leu Gly Met Ala
1               5                   10                  15
Ala Phe Gly Ala Ala Ala Leu Ala Gly Gly Thr Thr Ile Ala Ala Pro
            20                  25                  30
Arg Ala Ala Ala Ala Lys Ser Ala Ala Asp Asn Gly Gly Tyr Val
            35                  40                  45
Pro Ala Val Val Ile Gly Thr Gly Tyr Gly Ala Ala Val Ser Ala Leu
50                  55                  60
Arg Leu Gly Glu Ala Gly Val Gln Thr Leu Met Leu Glu Met Gly Gln
65                  70                  75                  80
Leu Trp Asn Gln Pro Gly Pro Asp Gly Asn Ile Phe Cys Gly Met Leu
            85                  90                  95
Asn Pro Asp Lys Arg Ser Ser Trp Phe Lys Asn Arg Thr Glu Ala Pro
            100                 105                 110
Leu Gly Ser Phe Leu Trp Leu Asp Val Val Asn Arg Asn Ile Asp Pro
            115                 120                 125
Tyr Ala Gly Val Leu Asp Arg Val Asn Tyr Asp Gln Met Ser Val Tyr
```

```
                    130                 135                 140
    Val Gly Arg Gly Val Gly Gly Ser Leu Val Asn Gly Met Ala
    145                 150                 155                 160
    Val Glu Pro Lys Arg Ser Tyr Phe Glu Ile Leu Pro Arg Val Asp
                        165                 170                 175
    Ser Ser Glu Met Tyr Asp Arg Tyr Phe Pro Arg Ala Asn Ser Met Leu
                180                 185                 190
    Arg Val Asn His Ile Asp Thr Lys Trp Phe Glu Asp Thr Glu Trp Tyr
                195                 200                 205
    Lys Phe Ala Arg Val Ser Arg Glu Gln Ala Gly Lys Ala Gly Leu Gly
                210                 215                 220
    Thr Val Phe Val Pro Asn Val Tyr Asp Phe Gly Tyr Met Gln Arg Glu
    225                 230                 235                 240
    Ala Ala Gly Glu Val Pro Lys Ser Ala Leu Ala Thr Glu Val Ile Tyr
                        245                 250                 255
    Gly Asn Asn His Gly Lys Gln Ser Leu Asp Lys Thr Tyr Leu Ala Ala
                        260                 265                 270
    Ala Leu Gly Thr Gly Lys Val Thr Ile Gln Thr Leu His Gln Val Lys
                275                 280                 285
    Thr Ile Arg Gln Thr Lys Asp Gly Gly Tyr Ala Leu Thr Val Glu Gln
                290                 295                 300
    Lys Asp Thr Asp Gly Lys Leu Leu Ala Thr Lys Glu Ile Ser Cys Arg
    305                 310                 315                 320
    Tyr Leu Phe Leu Gly Ala Gly Ser Leu Gly Ser Thr Glu Leu Leu Val
                        325                 330                 335
    Arg Ala Arg Asp Thr Gly Thr Leu Pro Asn Leu Asn Ser Glu Val Gly
                        340                 345                 350
    Ala Gly Trp Gly Pro Asn Gly Asn Ile Glu Thr Ala Arg Ala Asn His
                355                 360                 365
    Met Trp Asn Pro Thr Gly Ala His Gln Ser Ser Ile Pro Ala Leu Gly
                370                 375                 380
    Ile Asp Ala Trp Asp Asn Ser Asp Ser Ser Val Phe Ala Glu Ile Ala
    385                 390                 395                 400
    Pro Met Pro Ala Gly Leu Glu Thr Trp Val Ser Leu Tyr Leu Ala Ile
                        405                 410                 415
    Thr Lys Asn Pro Gln Arg Gly Thr Phe Val Tyr Asp Ala Ala Thr Asp
                        420                 425                 430
    Arg Ala Lys Leu Asn Trp Thr Arg Asp Gln Asn Ala Pro Ala Val Asn
                435                 440                 445
    Ala Ala Lys Ala Leu Phe Asp Arg Ile Asn Lys Ala Asn Gly Thr Ile
                450                 455                 460
    Tyr Arg Tyr Asp Leu Phe Gly Thr Gln Leu Lys Ala Phe Ala Asp Asp
    465                 470                 475                 480
    Phe Cys Tyr His Pro Leu Gly Gly Cys Val Leu Gly Lys Ala Thr Asp
                        485                 490                 495
    Asp Tyr Gly Arg Val Ala Gly Tyr Lys Asn Leu Tyr Val Thr Asp Gly
                        500                 505                 510
    Ser Leu Ile Pro Gly Ser Val Gly Val Asn Pro Phe Val Thr Ile Thr
                515                 520                 525
    Ala Leu Ala Glu Arg Asn Val Glu Arg Ile Ile Lys Gln Asp Val Thr
                530                 535                 540
    Ala Ser
    545
```

<210> SEQ ID NO 5
<211> LENGTH: 546
<212> TYPE: PRT
<213> ORGANISM: Artificial Sequence
<220> FEATURE:
<223> OTHER INFORMATION: Mutant M362R

<400> SEQUENCE: 5

```
Met Thr Ala Gln Gln His Leu Ser Arg Arg Arg Met Leu Gly Met Ala
1               5                   10                  15

Ala Phe Gly Ala Ala Ala Leu Ala Gly Gly Thr Thr Ile Ala Ala Pro
            20                  25                  30

Arg Ala Ala Ala Ala Lys Ser Ala Ala Asp Asn Gly Gly Tyr Val
        35                  40                  45

Pro Ala Val Val Ile Gly Thr Gly Tyr Gly Ala Ala Val Ser Ala Leu
    50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
            100                 105                 110

Leu Gly Ser Phe Leu Trp Leu Asp Val Val Asn Arg Asn Ile Asp Pro
        115                 120                 125

Tyr Ala Gly Val Leu Asp Arg Val Asn Tyr Asp Gln Met Ser Val Tyr
    130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
        195                 200                 205

Lys Phe Ala Arg Val Ser Arg Glu Gln Ala Gly Lys Ala Gly Leu Gly
    210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
        275                 280                 285

Thr Ile Arg Gln Thr Lys Asp Gly Gly Tyr Ala Leu Thr Val Glu Gln
    290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Arg Thr Ala Arg Ala Asn His
        355                 360                 365
```

```
Met Trp Asn Pro Thr Gly Ala His Gln Ser Ser Ile Pro Ala Leu Gly
            370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
            435                 440                 445

Ala Ala Lys Ala Leu Phe Asp Arg Ile Asn Lys Ala Asn Gly Thr Ile
            450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
                500                 505                 510

Ser Leu Ile Pro Gly Ser Val Gly Val Asn Pro Phe Val Thr Ile Thr
            515                 520                 525

Ala Leu Ala Glu Arg Asn Val Glu Arg Ile Ile Lys Gln Asp Val Thr
            530                 535                 540

Ala Ser
545

<210> SEQ ID NO 6
<211> LENGTH: 546
<212> TYPE: PRT
<213> ORGANISM: Artificial Sequence
<220> FEATURE:
<223> OTHER INFORMATION: Mutant M362A

<400> SEQUENCE: 6

Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
    50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
            100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
    130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175
```

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
        195                 200                 205

Lys Phe Ala Arg Val Ser Arg Glu Gln Ala Gly Lys Ala Gly Leu Gly
    210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
        275                 280                 285

Thr Ile Arg Gln Thr Lys Asp Gly Gly Tyr Ala Leu Thr Val Glu Gln
    290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Ala Thr Ala Arg Ala Asn His
        355                 360                 365

Met Trp Asn Pro Thr Gly Ala His Gln Ser Ser Ile Pro Ala Leu Gly
    370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
        435                 440                 445

Ala Ala Lys Ala Leu Phe Asp Arg Ile Asn Lys Ala Asn Gly Thr Ile
    450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Ser Val Gly Val Asn Pro Phe Val Thr Ile Thr
        515                 520                 525

Ala Leu Ala Glu Arg Asn Val Glu Arg Ile Ile Lys Gln Asp Val Thr
    530                 535                 540

Ala Ser
545

<210> SEQ ID NO 7
<211> LENGTH: 546
<212> TYPE: PRT
<213> ORGANISM: Artificial Sequence
<220> FEATURE:

<223> OTHER INFORMATION: Mutant M362W

<400> SEQUENCE: 7

```
Met Thr Ala Gln Gln His Leu Ser Arg Arg Met Leu Gly Met Ala
1               5                   10                  15

Ala Phe Gly Ala Ala Leu Ala Gly Gly Thr Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
195                 200                 205

Lys Phe Ala Arg Val Ser Arg Glu Gln Ala Gly Lys Ala Gly Leu Gly
210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
                260                 265                 270

Ala Leu Gly Thr Gly Lys Val Thr Ile Gln Thr Leu His Gln Val Lys
            275                 280                 285

Thr Ile Arg Gln Thr Lys Asp Gly Gly Tyr Ala Leu Thr Val Glu Gln
290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
                340                 345                 350

Ala Gly Trp Gly Pro Asn Gly Asn Ile Trp Thr Ala Arg Ala Asn His
            355                 360                 365

Met Trp Asn Pro Thr Gly Ala His Gln Ser Ser Ile Pro Ala Leu Gly
370                 375                 380

Ile Asp Ala Trp Asp Asn Ser Asp Ser Ser Val Phe Ala Glu Ile Ala
385                 390                 395                 400
```

```
Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
        435                 440                 445

Ala Ala Lys Ala Leu Phe Asp Arg Ile Asn Lys Ala Asn Gly Thr Ile
    450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Ser Val Gly Val Asn Pro Phe Val Thr Ile Thr
        515                 520                 525

Ala Leu Ala Glu Arg Asn Val Glu Arg Ile Ile Lys Gln Asp Val Thr
    530                 535                 540

Ala Ser
545

<210> SEQ ID NO 8
<211> LENGTH: 546
<212> TYPE: PRT
<213> ORGANISM: Artificial Sequence
<220> FEATURE:
<223> OTHER INFORMATION: Mutant M362P+L412Y

<400> SEQUENCE: 8

Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
    50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
130                 135                 140

Val Gly Arg Gly Val Gly Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
        195                 200                 205
```

```
Lys Phe Ala Arg Val Ser Arg Glu Gln Ala Gly Ala Gly Leu Gly
    210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
        275                 280                 285

Thr Ile Arg Gln Thr Lys Asp Gly Gly Tyr Ala Leu Thr Val Glu Gln
290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
        355                 360                 365

Met Trp Asn Pro Thr Gly Ala His Gln Ser Ser Ile Pro Ala Leu Gly
370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Tyr Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
        435                 440                 445

Ala Ala Lys Ala Leu Phe Asp Arg Ile Asn Lys Ala Asn Gly Thr Ile
    450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Ser Val Gly Val Asn Pro Phe Val Thr Ile Thr
        515                 520                 525

Ala Leu Ala Glu Arg Asn Val Glu Arg Ile Ile Lys Gln Asp Val Thr
    530                 535                 540

Ala Ser
545

<210> SEQ ID NO 9
<211> LENGTH: 546
<212> TYPE: PRT
<213> ORGANISM: Artificial Sequence
<220> FEATURE:
<223> OTHER INFORMATION: Mutant M362P+Y483M

<400> SEQUENCE: 9

Met Thr Ala Gln Gln His Leu Ser Arg Arg Arg Met Leu Gly Met Ala
1               5                   10                  15
```

```
Ala Phe Gly Ala Ala Ala Leu Ala Gly Gly Thr Thr Ile Ala Ala Pro
             20                  25                  30

Arg Ala Ala Ala Ala Lys Ser Ala Ala Asp Asn Gly Gly Tyr Val
         35                  40                  45

Pro Ala Val Val Ile Gly Thr Gly Tyr Gly Ala Ala Val Ser Ala Leu
         50                  55                  60

Arg Leu Gly Glu Ala Gly Val Gln Thr Leu Met Leu Glu Met Gly Gln
 65                  70                  75                  80

Leu Trp Asn Gln Pro Gly Pro Asp Gly Asn Ile Phe Cys Gly Met Leu
                 85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
        130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
                180                 185                 190

Arg Val Asn His Ile Asp Thr Lys Trp Phe Glu Asp Thr Glu Trp Tyr
            195                 200                 205

Lys Phe Ala Arg Val Ser Arg Glu Gln Ala Gly Lys Ala Gly Leu Gly
        210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
                260                 265                 270

Ala Leu Gly Thr Gly Lys Val Thr Ile Gln Thr Leu His Gln Val Lys
        275                 280                 285

Thr Ile Arg Gln Thr Lys Asp Gly Gly Tyr Ala Leu Thr Val Glu Gln
290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
        355                 360                 365

Met Trp Asn Pro Thr Gly Ala His Gln Ser Ser Ile Pro Ala Leu Gly
        370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
```

```
                435                 440                 445
Ala Ala Lys Ala Leu Phe Asp Arg Ile Asn Lys Ala Asn Gly Thr Ile
            450                 455                 460
Tyr Arg Tyr Asp Leu Phe Gly Thr Gln Leu Lys Ala Phe Ala Asp Asp
465                 470                 475                 480
Phe Cys Met His Pro Leu Gly Gly Cys Val Leu Gly Lys Ala Thr Asp
                485                 490                 495
Asp Tyr Gly Arg Val Ala Gly Tyr Lys Asn Leu Tyr Val Thr Asp Gly
            500                 505                 510
Ser Leu Ile Pro Gly Ser Val Gly Val Asn Pro Phe Val Thr Ile Thr
            515                 520                 525
Ala Leu Ala Glu Arg Asn Val Glu Arg Ile Ile Lys Gln Asp Val Thr
            530                 535                 540
Ala Ser
545

<210> SEQ ID NO 10
<211> LENGTH: 546
<212> TYPE: PRT
<213> ORGANISM: Artificial Sequence
<220> FEATURE:
<223> OTHER INFORMATION: Mutant M362P+Y483W

<400> SEQUENCE: 10

Met Thr Ala Gln Gln His Leu Ser Arg Arg Arg Met Leu Gly Met Ala
1               5                   10                  15
Ala Phe Gly Ala Ala Ala Leu Ala Gly Gly Thr Thr Ile Ala Ala Pro
            20                  25                  30
Arg Ala Ala Ala Ala Lys Ser Ala Ala Asp Asn Gly Gly Tyr Val
            35                  40                  45
Pro Ala Val Val Ile Gly Thr Gly Tyr Gly Ala Ala Val Ser Ala Leu
        50                  55                  60
Arg Leu Gly Glu Ala Gly Val Gln Thr Leu Met Leu Glu Met Gly Gln
65                  70                  75                  80
Leu Trp Asn Gln Pro Gly Pro Asp Gly Asn Ile Phe Cys Gly Met Leu
                85                  90                  95
Asn Pro Asp Lys Arg Ser Ser Trp Phe Lys Asn Arg Thr Glu Ala Pro
            100                 105                 110
Leu Gly Ser Phe Leu Trp Leu Asp Val Val Asn Arg Asn Ile Asp Pro
        115                 120                 125
Tyr Ala Gly Val Leu Asp Arg Val Asn Tyr Asp Gln Met Ser Val Tyr
    130                 135                 140
Val Gly Arg Gly Val Gly Gly Ser Leu Val Asn Gly Gly Met Ala
145                 150                 155                 160
Val Glu Pro Lys Arg Ser Tyr Phe Glu Glu Ile Leu Pro Arg Val Asp
                165                 170                 175
Ser Ser Glu Met Tyr Asp Arg Tyr Phe Pro Arg Ala Asn Ser Met Leu
            180                 185                 190
Arg Val Asn His Ile Asp Thr Lys Trp Phe Glu Asp Thr Glu Trp Tyr
        195                 200                 205
Lys Phe Ala Arg Val Ser Arg Glu Gln Ala Gly Lys Ala Gly Leu Gly
    210                 215                 220
Thr Val Phe Val Pro Asn Val Tyr Asp Phe Gly Tyr Met Gln Arg Glu
225                 230                 235                 240
Ala Ala Gly Glu Val Pro Lys Ser Ala Leu Ala Thr Glu Val Ile Tyr
```

```
            245                 250                 255
Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
            275                 280                 285

Thr Ile Arg Gln Thr Lys Asp Gly Gly Tyr Ala Leu Thr Val Glu Gln
            290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
                340                 345                 350

Ala Gly Trp Gly Pro Asn Gly Asn Ile Pro Thr Ala Arg Ala Asn His
                355                 360                 365

Met Trp Asn Pro Thr Gly Ala His Gln Ser Ser Ile Pro Ala Leu Gly
            370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
            435                 440                 445

Ala Ala Lys Ala Leu Phe Asp Arg Ile Asn Lys Ala Asn Gly Thr Ile
            450                 455                 460

Tyr Arg Tyr Asp Leu Phe Gly Thr Gln Leu Lys Ala Phe Ala Asp Asp
465                 470                 475                 480

Phe Cys Trp His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Ser Val Gly Val Asn Pro Phe Val Thr Ile Thr
            515                 520                 525

Ala Leu Ala Glu Arg Asn Val Glu Arg Ile Ile Lys Gln Asp Val Thr
            530                 535                 540

Ala Ser
545

<210> SEQ ID NO 11
<211> LENGTH: 546
<212> TYPE: PRT
<213> ORGANISM: Artificial Sequence
<220> FEATURE:
<223> OTHER INFORMATION: Mutant M362P+S518G

<400> SEQUENCE: 11

Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
```

```
             50                  55                  60
Arg Leu Gly Glu Ala Gly Val Gln Thr Leu Met Leu Glu Met Gly Gln
 65                  70                  75                  80

Leu Trp Asn Gln Pro Gly Pro Asp Gly Asn Ile Phe Cys Gly Met Leu
                 85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
                115                 120                 125

Tyr Ala Gly Val Leu Asp Arg Val Asn Tyr Asp Gln Met Ser Val Tyr
            130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
                180                 185                 190

Arg Val Asn His Ile Asp Thr Lys Trp Phe Glu Asp Thr Glu Trp Tyr
            195                 200                 205

Lys Phe Ala Arg Val Ser Arg Glu Gln Ala Gly Lys Ala Gly Leu Gly
210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
                260                 265                 270

Ala Leu Gly Thr Gly Lys Val Thr Ile Gln Thr Leu His Gln Val Lys
            275                 280                 285

Thr Ile Arg Gln Thr Lys Asp Gly Gly Tyr Ala Leu Thr Val Glu Gln
            290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
            355                 360                 365

Met Trp Asn Pro Thr Gly Ala His Gln Ser Ser Ile Pro Ala Leu Gly
    370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
                420                 425                 430

Arg Ala Lys Leu Asn Trp Thr Arg Asp Gln Asn Ala Pro Ala Val Asn
            435                 440                 445

Ala Ala Lys Ala Leu Phe Asp Arg Ile Asn Lys Ala Asn Gly Thr Ile
        450                 455                 460

Tyr Arg Tyr Asp Leu Phe Gly Thr Gln Leu Lys Ala Phe Ala Asp Asp
465                 470                 475                 480
```

```
Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Gly Val Gly Val Asn Pro Phe Val Thr Ile Thr
        515                 520                 525

Ala Leu Ala Glu Arg Asn Val Glu Arg Ile Ile Lys Gln Asp Val Thr
    530                 535                 540

Ala Ser
545

<210> SEQ ID NO 12
<211> LENGTH: 546
<212> TYPE: PRT
<213> ORGANISM: Artificial Sequence
<220> FEATURE:
<223> OTHER INFORMATION: Mutant M362P+S518L

<400> SEQUENCE: 12

Met Thr Ala Gln Gln His Leu Ser Arg Arg Met Leu Gly Met Ala
1               5                   10                  15

Ala Phe Gly Ala Ala Ala Leu Ala Gly Gly Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
        50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
        130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
        195                 200                 205

Lys Phe Ala Arg Val Ser Arg Glu Gln Ala Gly Lys Ala Gly Leu Gly
    210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
        275                 280                 285
```

Thr Ile Arg Gln Thr Lys Asp Gly Gly Tyr Ala Leu Thr Val Glu Gln
    290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
        355                 360                 365

Met Trp Asn Pro Thr Gly Ala His Gln Ser Ser Ile Pro Ala Leu Gly
370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
        435                 440                 445

Ala Ala Lys Ala Leu Phe Asp Arg Ile Asn Lys Ala Asn Gly Thr Ile
450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Leu Val Gly Val Asn Pro Phe Val Thr Ile Thr
        515                 520                 525

Ala Leu Ala Glu Arg Asn Val Glu Arg Ile Ile Lys Gln Asp Val Thr
530                 535                 540

Ala Ser
545

<210> SEQ ID NO 13
<211> LENGTH: 546
<212> TYPE: PRT
<213> ORGANISM: Artificial Sequence
<220> FEATURE:
<223> OTHER INFORMATION: Mutant M362P+S518T

<400> SEQUENCE: 13

Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
        50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

-continued

```
Asn Pro Asp Lys Arg Ser Ser Trp Phe Lys Asn Arg Thr Glu Ala Pro
            100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
            130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
            195                 200                 205

Lys Phe Ala Arg Val Ser Arg Glu Gln Ala Gly Lys Ala Gly Leu Gly
            210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
            275                 280                 285

Thr Ile Arg Gln Thr Lys Asp Gly Gly Tyr Ala Leu Thr Val Glu Gln
            290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
            355                 360                 365

Met Trp Asn Pro Thr Gly Ala His Gln Ser Ser Ile Pro Ala Leu Gly
370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
            435                 440                 445

Ala Ala Lys Ala Leu Phe Asp Arg Ile Asn Lys Ala Asn Gly Thr Ile
            450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510
```

```
Ser Leu Ile Pro Gly Thr Val Gly Val Asn Pro Phe Thr Ile Thr
    515                 520                 525

Ala Leu Ala Glu Arg Asn Val Glu Arg Ile Ile Lys Gln Asp Val Thr
530                 535                 540

Ala Ser
545

<210> SEQ ID NO 14
<211> LENGTH: 546
<212> TYPE: PRT
<213> ORGANISM: Artificial Sequence
<220> FEATURE:
<223> OTHER INFORMATION: Mutant M362P+S518A

<400> SEQUENCE: 14

Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
            20                  25                  30

Arg Ala Ala Ala Ala Lys Ser Ala Ala Asp Asn Gly Gly Tyr Val
        35                  40                  45

Pro Ala Val Val Ile Gly Thr Gly Tyr Gly Ala Ala Val Ser Ala Leu
50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
            100                 105                 110

Leu Gly Ser Phe Leu Trp Leu Asp Val Val Asn Arg Asn Ile Asp Pro
        115                 120                 125

Tyr Ala Gly Val Leu Asp Arg Val Asn Tyr Asp Gln Met Ser Val Tyr
130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
        195                 200                 205

Lys Phe Ala Arg Val Ser Arg Glu Gln Ala Gly Lys Ala Gly Leu Gly
210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
        275                 280                 285

Thr Ile Arg Gln Thr Lys Asp Gly Gly Tyr Ala Leu Thr Val Glu Gln
290                 295                 300

Lys Asp Thr Asp Gly Lys Leu Leu Ala Thr Lys Glu Ile Ser Cys Arg
305                 310                 315                 320
```

Tyr Leu Phe Leu Gly Ala Gly Ser Leu Gly Ser Thr Glu Leu Leu Val
            325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
            355                 360                 365

Met Trp Asn Pro Thr Gly Ala His Gln Ser Ser Ile Pro Ala Leu Gly
370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
            405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
            435                 440                 445

Ala Ala Lys Ala Leu Phe Asp Arg Ile Asn Lys Ala Asn Gly Thr Ile
            450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
            485                 490                 495

Asp Tyr Gly Arg Val Ala Gly Tyr Lys Asn Leu Tyr Val Thr Asp Gly
            500                 505                 510

Ser Leu Ile Pro Gly Ala Val Gly Val Asn Pro Phe Val Thr Ile Thr
            515                 520                 525

Ala Leu Ala Glu Arg Asn Val Glu Arg Ile Ile Lys Gln Asp Val Thr
            530                 535                 540

Ala Ser
545

<210> SEQ ID NO 15
<211> LENGTH: 546
<212> TYPE: PRT
<213> ORGANISM: Artificial Sequence
<220> FEATURE:
<223> OTHER INFORMATION: Mutant M362P+V519C

<400> SEQUENCE: 15

Met Thr Ala Gln Gln His Leu Ser Arg Arg Met Leu Gly Met Ala
1               5                   10                  15

Ala Phe Gly Ala Ala Leu Ala Gly Gly Thr Thr Ile Ala Ala Pro
            20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
            85                  90                  95

Asn Pro Asp Lys Arg Ser Ser Trp Phe Lys Asn Arg Thr Glu Ala Pro
            100                 105                 110

Leu Gly Ser Phe Leu Trp Leu Asp Val Val Asn Arg Asn Ile Asp Pro
            115                 120                 125

```
Tyr Ala Gly Val Leu Asp Arg Val Asn Tyr Asp Gln Met Ser Val Tyr
130                 135                 140

Val Gly Arg Gly Val Gly Gly Ser Leu Val Asn Gly Gly Met Ala
145                 150                 155                 160

Val Glu Pro Lys Arg Ser Tyr Phe Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
        195                 200                 205

Lys Phe Ala Arg Val Ser Arg Glu Gln Ala Gly Lys Ala Gly Leu Gly
210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
        275                 280                 285

Thr Ile Arg Gln Thr Lys Asp Gly Gly Tyr Ala Leu Thr Val Glu Gln
290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
        355                 360                 365

Met Trp Asn Pro Thr Gly Ala His Gln Ser Ser Ile Pro Ala Leu Gly
370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
            420                 425                 430

Arg Ala Lys Leu Asn Trp Thr Arg Asp Gln Asn Ala Pro Ala Val Asn
        435                 440                 445

Ala Ala Lys Ala Leu Phe Asp Arg Ile Asn Lys Ala Asn Gly Thr Ile
450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Ser Cys Gly Val Asn Pro Phe Val Thr Ile Thr
        515                 520                 525

Ala Leu Ala Glu Arg Asn Val Glu Arg Ile Ile Lys Gln Asp Val Thr
530                 535                 540

Ala Ser
```

<210> SEQ ID NO 16
<211> LENGTH: 546
<212> TYPE: PRT
<213> ORGANISM: Artificial Sequence
<220> FEATURE:
<223> OTHER INFORMATION: Mutant M362P+V519I

<400> SEQUENCE: 16

```
Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
    50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
    130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
    195                 200                 205

Lys Phe Ala Arg Val Ser Arg Glu Gln Ala Gly Lys Ala Gly Leu Gly
210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
            260                 265                 270

Ala Leu Gly Thr Gly Lys Val Thr Ile Gln Thr Leu His Gln Val Lys
    275                 280                 285

Thr Ile Arg Gln Thr Lys Asp Gly Gly Tyr Ala Leu Thr Val Glu Gln
290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
```

```
                355                 360                 365
Met Trp Asn Pro Thr Gly Ala His Gln Ser Ser Ile Pro Ala Leu Gly
        370                 375                 380

Ile Asp Ala Trp Asp Asn Ser Asp Ser Ser Val Phe Ala Glu Ile Ala
385                 390                 395                 400

Pro Met Pro Ala Gly Leu Glu Thr Trp Val Ser Leu Tyr Leu Ala Ile
                405                 410                 415

Thr Lys Asn Pro Gln Arg Gly Thr Phe Val Tyr Asp Ala Ala Thr Asp
                420                 425                 430

Arg Ala Lys Leu Asn Trp Thr Arg Asp Gln Asn Ala Pro Ala Val Asn
                435                 440                 445

Ala Ala Lys Ala Leu Phe Asp Arg Ile Asn Lys Ala Asn Gly Thr Ile
        450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
                500                 505                 510

Ser Leu Ile Pro Gly Ser Ile Gly Val Asn Pro Phe Val Thr Ile Thr
        515                 520                 525

Ala Leu Ala Glu Arg Asn Val Glu Arg Ile Ile Lys Gln Asp Val Thr
        530                 535                 540

Ala Ser
545

<210> SEQ ID NO 17
<211> LENGTH: 546
<212> TYPE: PRT
<213> ORGANISM: Artificial Sequence
<220> FEATURE:
<223> OTHER INFORMATION: Mutant M362P+V519S

<400> SEQUENCE: 17

Met Thr Ala Gln Gln His Leu Ser Arg Arg Met Leu Gly Met Ala
1               5                   10                  15

Ala Phe Gly Ala Ala Ala Leu Ala Gly Gly Thr Thr Ile Ala Ala Pro
            20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
    50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
            100                 105                 110

Leu Gly Ser Phe Leu Trp Leu Asp Val Val Asn Arg Asn Ile Asp Pro
        115                 120                 125

Tyr Ala Gly Val Leu Asp Arg Val Asn Tyr Asp Gln Met Ser Val Tyr
    130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
```

165                 170                 175
Ser Ser Glu Met Tyr Asp Arg Tyr Phe Pro Arg Ala Asn Ser Met Leu
            180                 185                 190
Arg Val Asn His Ile Asp Thr Lys Trp Phe Glu Asp Thr Glu Trp Tyr
            195                 200                 205
Lys Phe Ala Arg Val Ser Arg Glu Gln Ala Gly Lys Ala Gly Leu Gly
            210                 215                 220
Thr Val Phe Val Pro Asn Val Tyr Asp Phe Gly Tyr Met Gln Arg Glu
225                 230                 235                 240
Ala Ala Gly Glu Val Pro Lys Ser Ala Leu Ala Thr Glu Val Ile Tyr
            245                 250                 255
Gly Asn Asn His Gly Lys Gln Ser Leu Asp Lys Thr Tyr Leu Ala Ala
            260                 265                 270
Ala Leu Gly Thr Gly Lys Val Thr Ile Gln Thr Leu His Gln Val Lys
            275                 280                 285
Thr Ile Arg Gln Thr Lys Asp Gly Gly Tyr Ala Leu Thr Val Glu Gln
            290                 295                 300
Lys Asp Thr Asp Gly Lys Leu Leu Ala Thr Lys Glu Ile Ser Cys Arg
305                 310                 315                 320
Tyr Leu Phe Leu Gly Ala Gly Ser Leu Gly Ser Thr Glu Leu Leu Val
            325                 330                 335
Arg Ala Arg Asp Thr Gly Thr Leu Pro Asn Leu Asn Ser Glu Val Gly
            340                 345                 350
Ala Gly Trp Gly Pro Asn Gly Asn Ile Pro Thr Ala Arg Ala Asn His
            355                 360                 365
Met Trp Asn Pro Thr Gly Ala His Gln Ser Ser Ile Pro Ala Leu Gly
            370                 375                 380
Ile Asp Ala Trp Asp Asn Ser Asp Ser Ser Val Phe Ala Glu Ile Ala
385                 390                 395                 400
Pro Met Pro Ala Gly Leu Glu Thr Trp Val Ser Leu Tyr Leu Ala Ile
            405                 410                 415
Thr Lys Asn Pro Gln Arg Gly Thr Phe Val Tyr Asp Ala Ala Thr Asp
            420                 425                 430
Arg Ala Lys Leu Asn Trp Thr Arg Asp Gln Asn Ala Pro Ala Val Asn
            435                 440                 445
Ala Ala Lys Ala Leu Phe Asp Arg Ile Asn Lys Ala Asn Gly Thr Ile
            450                 455                 460
Tyr Arg Tyr Asp Leu Phe Gly Thr Gln Leu Lys Ala Phe Ala Asp Asp
465                 470                 475                 480
Phe Cys Tyr His Pro Leu Gly Gly Cys Val Leu Gly Lys Ala Thr Asp
            485                 490                 495
Asp Tyr Gly Arg Val Ala Gly Tyr Lys Asn Leu Tyr Val Thr Asp Gly
            500                 505                 510
Ser Leu Ile Pro Gly Ser Ser Gly Val Asn Pro Phe Val Thr Ile Thr
            515                 520                 525
Ala Leu Ala Glu Arg Asn Val Glu Arg Ile Ile Lys Gln Asp Val Thr
            530                 535                 540
Ala Ser
545

<210> SEQ ID NO 18
<211> LENGTH: 546
<212> TYPE: PRT
<213> ORGANISM: Artificial Sequence
<220> FEATURE:
<223> OTHER INFORMATION: Mutant M362P+V519T

<400> SEQUENCE: 18

```
Met Thr Ala Gln Gln His Leu Ser Arg Arg Met Leu Gly Met Ala
1               5                   10                  15

Ala Phe Gly Ala Ala Leu Ala Gly Gly Thr Thr Ile Ala Ala Pro
                20                  25                  30

Arg Ala Ala Ala Ala Lys Ser Ala Ala Asp Asn Gly Gly Tyr Val
            35                  40                  45

Pro Ala Val Val Ile Gly Thr Gly Tyr Gly Ala Ala Val Ser Ala Leu
50                  55                  60

Arg Leu Gly Glu Ala Gly Val Gln Thr Leu Met Leu Glu Met Gly Gln
65                  70                  75                  80

Leu Trp Asn Gln Pro Gly Pro Asp Gly Asn Ile Phe Cys Gly Met Leu
                85                  90                  95

Asn Pro Asp Lys Arg Ser Ser Trp Phe Lys Asn Arg Thr Glu Ala Pro
                100                 105                 110

Leu Gly Ser Phe Leu Trp Leu Asp Val Val Asn Arg Asn Ile Asp Pro
            115                 120                 125

Tyr Ala Gly Val Leu Asp Arg Val Asn Tyr Asp Gln Met Ser Val Tyr
130                 135                 140

Val Gly Arg Gly Val Gly Gly Ser Leu Val Asn Gly Gly Met Ala
145                 150                 155                 160

Val Glu Pro Lys Arg Ser Tyr Phe Glu Glu Ile Leu Pro Arg Val Asp
                165                 170                 175

Ser Ser Glu Met Tyr Asp Arg Tyr Phe Pro Arg Ala Asn Ser Met Leu
            180                 185                 190

Arg Val Asn His Ile Asp Thr Lys Trp Phe Glu Asp Thr Glu Trp Tyr
195                 200                 205

Lys Phe Ala Arg Val Ser Arg Glu Gln Ala Gly Lys Ala Gly Leu Gly
            210                 215                 220

Thr Val Phe Val Pro Asn Val Tyr Asp Phe Gly Tyr Met Gln Arg Glu
225                 230                 235                 240

Ala Ala Gly Glu Val Pro Lys Ser Ala Leu Ala Thr Glu Val Ile Tyr
                245                 250                 255

Gly Asn Asn His Gly Lys Gln Ser Leu Asp Lys Thr Tyr Leu Ala Ala
                260                 265                 270

Ala Leu Gly Thr Gly Lys Val Thr Ile Gln Thr Leu His Gln Val Lys
            275                 280                 285

Thr Ile Arg Gln Thr Lys Asp Gly Gly Tyr Ala Leu Thr Val Glu Gln
290                 295                 300

Lys Asp Thr Asp Gly Lys Leu Leu Ala Thr Lys Glu Ile Ser Cys Arg
305                 310                 315                 320

Tyr Leu Phe Leu Gly Ala Gly Ser Leu Gly Ser Thr Glu Leu Leu Val
                325                 330                 335

Arg Ala Arg Asp Thr Gly Thr Leu Pro Asn Leu Asn Ser Glu Val Gly
            340                 345                 350

Ala Gly Trp Gly Pro Asn Gly Asn Ile Pro Thr Ala Arg Ala Asn His
            355                 360                 365

Met Trp Asn Pro Thr Gly Ala His Gln Ser Ile Pro Ala Leu Gly
            370                 375                 380

Ile Asp Ala Trp Asp Asn Ser Asp Ser Ser Val Phe Ala Glu Ile Ala
385                 390                 395                 400
```

```
Pro Met Pro Ala Gly Leu Glu Thr Trp Val Ser Leu Tyr Leu Ala Ile
            405                 410                 415

Thr Lys Asn Pro Gln Arg Gly Thr Phe Val Tyr Asp Ala Ala Thr Asp
        420                 425                 430

Arg Ala Lys Leu Asn Trp Thr Arg Asp Gln Asn Ala Pro Ala Val Asn
            435                 440                 445

Ala Ala Lys Ala Leu Phe Asp Arg Ile Asn Lys Ala Asn Gly Thr Ile
    450                 455                 460

Tyr Arg Tyr Asp Leu Phe Gly Thr Gln Leu Lys Ala Phe Ala Asp Asp
465                 470                 475                 480

Phe Cys Tyr His Pro Leu Gly Gly Cys Val Leu Gly Lys Ala Thr Asp
                485                 490                 495

Asp Tyr Gly Arg Val Ala Gly Tyr Lys Asn Leu Tyr Val Thr Asp Gly
            500                 505                 510

Ser Leu Ile Pro Gly Ser Thr Gly Val Asn Pro Phe Val Thr Ile Thr
        515                 520                 525

Ala Leu Ala Glu Arg Asn Val Glu Arg Ile Ile Lys Gln Asp Val Thr
    530                 535                 540

Ala Ser
545

<210> SEQ ID NO 19
<211> LENGTH: 1641
<212> TYPE: DNA
<213> ORGANISM: Streptomyces sp.

<400> SEQUENCE: 19
atgaccgctc aacaacatct gtcccgccgc cgcatgctgg gtatggccgc ctttggtgcc      60
gccgctctgg caggtggtac gacgattgct gcaccgcgtg cagcagcagc tgcaaaaagc     120
gcagcagata atggcggtta tgttccggcg gtggttattg gtacgggtta cggtgctgca     180
gtgtctgcac tgcgtctggg tgaagccggc gttcagaccc tgatgctgga aatgggtcag     240
ctgtggaacc aaccgggtcc ggacggcaat atcttttgcg catgctgaa cccggataaa      300 cgtagctctt ggtttaaaaa ccgcaccgaa gccccgctgg ttctttcct gtggctggac      360 gtcgtgaacc gtaatatcga tccgtatgca ggcgttctgg accgcgtcaa ttatgatcaa     420
atgagcgttt acgtcggtcg tggtgtgggc ggtggctctc tggttaacgg tggcatggcg     480
gtcgaaccga acgtagttta ttttgaagaa attctgccgc gcgtcgacag ttccgaaatg     540
tatgatcgtt acttcccgcg cgcgaactcc atgctgcgcg tgaatcatat cgacaccaaa     600
tggtttgaag atacggaatg gtataaattc gcccgtgtga gtcgcgaaca ggccggtaaa     660
gctggcctgg gtaccgtgtt tgttccgaat gtttatgatt cggttacat gcaacgtgaa      720 gccgcaggcg aagttccgaa agtgcactg gctaccgaag tcatctatgg taacaatcat      780
ggcaaacagt ccctggacaa aacgtacctg gctgcagcac tgggtaccgg taaagtgacc     840
attcagacgc tgcaccaagt taaaaccatc cgtcagacga agatggtgg ctatgcgctg      900 accgtggaac aaaaagatac ggacggtaaa ctgctggcca cgaaagaaat tagctgtcgc     960
tacctgtttc tgggcgccgg tagtctgggt tccaccgaac tgctggtccg tgcacgtgat    1020
accggtacgc tgccgaacct gaatagcgaa gtgggtgcag gttgggtcc gaacggcaat    1080 attatgaccg cgcgcgccaa ccatatgtgg aatccgaccg tgcccacca gtcatcgatt    1140 ccggcactgg gcatcgatgc ttgggacaac tcagatagct ctgttttgc ggaaattgcc    1200
```

-continued

```
ccgatgccgg caggtctgga aacctgggtc tcgctgtatc tggctatcac caaaaatccg    1260
cagcgtggca cgttcgttta cgacgcagct accgatcgtg cgaaactgaa ctggacccgc    1320
gatcaaaacg caccggctgt gaatgcggcc aaagcactgt ttgaccgtat taacaaagct    1380
aatggtacga tctatcgcta cgacctgttt ggcacccagc tgaaagcgtt tgccgatgac    1440
ttctgctatc acccgctggg tggctgtgtt ctgggtaaag caacggatga ctacggtcgt    1500
gtcgcaggtt ataaaaatct gtacgtgacc gatggctcac tgattccggg ttcggtcggc    1560
gtgaacccgt tcgtgaccat taccgcactg gcagaacgca acgtggaacg cattattaaa    1620
caggatgtca ccgcaagttg a                                              1641
```

<210> SEQ ID NO 20
<211> LENGTH: 1641
<212> TYPE: DNA
<213> ORGANISM: Artificial Sequence
<220> FEATURE:
<223> OTHER INFORMATION: Mutant L113E

<400> SEQUENCE: 20

```
atgaccgctc aacaacatct gtcccgccgc cgcatgctgg gtatggccgc ctttggtgcc     60
gccgctctgg caggtggtac gacgattgct gcaccgcgtg cagcagcagc tgcaaaaagc    120
gcagcagata tggcggttta tgttccggcg gtggttattg gtacgggtta cggtgctgca    180
gtgtctcgac tgcgtctggg tgaagccggc gttcagaccc tgatgctgga atgggtcag    240 ctgtggaacc aaccgggtcc ggacggcaat atcttttgcg gcatgctgaa cccggataaa    300
cgtagctctt ggtttaaaaa ccgcaccgaa gccccggaag ttcttttcct gtggctggac    360
gtcgtgaacc gtaatatcga tccgtatgca ggcgttctgg accgcgtcaa ttatgatcaa    420
atgagcgttt acgtcggtcg tggtgtgggc ggtggctctc tggttaacgg tggcatggcg    480
gtcgaaccga aacgtagtta ttttgaagaa attctgccgc gcgtcgacag ttccgaaatg    540
tatgatcgtt acttcccgcg cgcgaactcc atgctgcgcg tgaatcatat cgacaccaaa    600
tggtttgaag atacggaatg gtataaattc gcccgtgtga gtcgcgaaca ggccggtaaa    660
gctggcctgg gtaccgtgtt tgttccgaat gttatgatt cggttacat gcaacgtgaa    720 gccgcaggcg aagttccgaa agtgcactg gctaccgaag tcatctatgg taacaatcat    780
ggcaaacagt ccctggacaa aacgtacctg gctgcagcac tgggtaccgg taaagtgacc    840
attcagacgc tgcaccaagt taaaaccatc cgtcagacga agatggtgg ctatgcgctg    900 accgtggaac aaaagatac ggacggtaaa ctgctggcca cgaaagaaat tagctgtcgc    960
tacctgtttc tgggcgccgg tagtctgggt tccaccgaac tgctggtccg tgcacgtgat    1020
accggtacgc tgccgaacct gaatagcgaa gtgggtgcag ttgggggtcc gaacggcaat    1080
attatgaccg cgcgcgccaa ccatatgtgg aatccgaccg gtgcccacca gtcatcgatt    1140
ccggcactgg gcatcgatgc ttgggacaac tcagatagct ctgttttttgc ggaaattgcc    1200 ccgatgccgg caggtctgga aacctgggtc tcgctgtatc tggctatcac caaaaatccg    1260
cagcgtggca cgttcgttta cgacgcagct accgatcgtg cgaaactgaa ctggacccgc    1320
gatcaaaacg caccggctgt gaatgcggcc aaagcactgt ttgaccgtat taacaaagct    1380
aatggtacga tctatcgcta cgacctgttt ggcacccagc tgaaagcgtt tgccgatgac    1440
ttctgctatc acccgctggg tggctgtgtt ctgggtaaag caacggatga ctacggtcgt    1500
gtcgcaggtt ataaaaatct gtacgtgacc gatggctcac tgattccggg ttcggtcggc    1560
gtgaacccgt tcgtgaccat taccgcactg gcagaacgca acgtggaacg cattattaaa    1620
```

<210> SEQ ID NO 21
<211> LENGTH: 1641
<212> TYPE: DNA
<213> ORGANISM: Artificial Sequence
<220> FEATURE:
<223> OTHER INFORMATION: Mutant M362P

<400> SEQUENCE: 21

```
atgaccgctc aacaacatct gtcccgccgc cgcatgctgg gtatggccgc ctttggtgcc      60
gccgctctgg caggtggtac gacgattgct gcaccgcgtg cagcagcagc tgcaaaaagc     120
gcagcagata atggcggtta tgttccggcg gtggttattg gtacgggtta cggtgctgca     180
gtgtctgcac tgcgtctggg tgaagccggc gttcagaccc tgatgctgga atgggtcag     240
ctgtggaacc aaccgggtcc ggacggcaat atcttttgcg gcatgctgaa cccggataaa     300
cgtagctctt ggtttaaaaa ccgcaccgaa gccccgctgg ttctttcct gtggctggac     360
gtcgtgaacc gtaatatcga tccgtatgca ggcgttctgg accgcgtcaa ttatgatcaa     420
atgagcgttt acgtcggtcg tggtgtgggc ggtggctctc tggttaacgg tggcatggcg     480
gtcgaaccga acgtagtta ttttgaagaa attctgccgc gcgtcgacag ttccgaaatg     540
tatgatcgtt acttcccgcg cgcgaactcc atgctgcgcg tgaatcatat cgacaccaaa     600
tggtttgaag atacggaatg gtataaattc gcccgtgtga gtcgcgaaca ggccggtaaa     660
gctggcctgg gtaccgtgtt tgttccgaat gtttatgatt tcggttacat gcaacgtgaa     720
gccgcaggcg aagttccgaa agtgcactg gctaccgaag tcatctatgg taacaatcat     780
ggcaaacagt ccctggacaa aacgtacctg gctgcagcac tgggtaccgg taaagtgacc     840
attcagacgc tgcaccaagt taaaaccatc cgtcagacga agatggtgg ctatgcgctg     900
accgtggaac aaaagatac ggacggtaaa ctgctggcca cgaaagaaat tagctgtcgc     960
tacctgtttc tgggcgccgg tagtctgggt tccaccgaac tgctggtccg tgcacgtgat    1020
accggtacgc tgccgaacct gaatagcgaa gtgggtgcag ttgggggtcc gaacggcaat    1080
attccgaccg cgcgcgccaa ccatatgtgg aatccgaccg gtgcccacca gtcatcgatt    1140
ccggcactgg gcatcgatgc ttgggacaac tcagatagct ctgttttgc ggaaattgcc    1200
ccgatgccgc aggtctgga aacctgggtc tcgctgtatc tggctatcac caaaaatccg    1260
cagcgtggca cgttcgttta cgacgcagct accgatcgtg cgaaactgaa ctggacccgc    1320
gatcaaaacg caccggctgt gaatgcggcc aaagcactgt tgaccgtat taacaaagct    1380
aatggtacga tctatcgcta cgacctgttt ggcacccagc tgaaagcgtt tgccgatgac    1440
ttctgctatc acccgctggg tggctgtgtt ctgggtaaag caacggatga ctacggtcgt    1500
gtcgcaggtt ataaaatct gtacgtgacc gatggctcac tgattccggg ttcggtcggc    1560
gtgaacccgt tcgtgaccat taccgcactg gcagaacgca acgtggaacg cattattaaa    1620
caggatgtca ccgcaagttg a                                              1641
```

<210> SEQ ID NO 22
<211> LENGTH: 1641
<212> TYPE: DNA
<213> ORGANISM: Artificial Sequence
<220> FEATURE:
<223> OTHER INFORMATION: Mutant M362E

<400> SEQUENCE: 22

```
atgaccgctc aacaacatct gtcccgccgc cgcatgctgg gtatggccgc ctttggtgcc    60
gccgctctgg caggtggtac gacgattgct gcaccgcgtg cagcagcagc tgcaaaaagc   120
gcagcagata atggcggtta tgttccggcg gtggttattg gtacgggtta cggtgctgca   180
gtgtctgcac tgcgtctggg tgaagccggc gttcagaccc tgatgctgga aatgggtcag   240
ctgtggaacc aaccgggtcc ggacggcaat atcttttgcg gcatgctgaa cccggataaa   300
cgtagctctt ggtttaaaaa ccgcaccgaa gccccgctgg gttctttcct gtggctggac   360
gtcgtgaacc gtaatatcga tccgtatgca ggcgttctgg accgcgtcaa ttatgatcaa   420
atgagcgttt acgtcggtcg tggtgtgggc ggtggctctc tggttaacgg tggcatggcg   480
gtcgaaccga aacgtagtta ttttgaagaa attctgccgc gcgtcgacag ttccgaaatg   540
tatgatcgtt acttcccgcg cgcgaactcc atgctgcgcg tgaatcatat cgacaccaaa   600
tggtttgaag atacggaatg gtataaattc gcccgtgtga gtcgcgaaca ggccggtaaa   660
gctggcctgg gtaccgtgtt tgttccgaat gtttatgatt tcggttacat gcaacgtgaa   720
gccgcaggcg aagttccgaa aagtgcactg gctaccgaag tcatctatgg taacaatcat   780
ggcaaacagt ccctggacaa aacgtacctg gctgcagcac tgggtaccgg taaagtgacc   840
attcagacgc tgcaccaagt taaaaccatc cgtcagacga agatggtgg ctatgcgctg   900
accgtggaac aaaaagatac ggacggtaaa ctgctggcca cgaaagaaat tagctgtcgc   960
tacctgtttc tgggcgccgg tagtctgggt tccaccgaac tgctggtccg tgcacgtgat  1020
accggtacgc tgccgaacct gaatagcgaa gtgggtgcag gttggggtcc gaacggcaat  1080
attgaaaccg cgcgcgccaa ccatatgtgg aatccgaccg tgcccacca gtcatcgatt  1140
ccggcactgg gcatcgatgc ttgggacaac tcagatagct ctgttttttgc ggaaattgcc  1200
ccgatgccgg caggtctgga aacctgggtc tcgctgtatc tggctatcac caaaaatccg  1260
cagcgtggca cgttcgttta cgacgcagct accgatcgtg cgaaactgaa ctggacccgc  1320
gatcaaaacg caccggctgt gaatgcgcc aaagcactgt ttgaccgtat taacaaagct  1380
aatggtacga tctatcgcta cgacctgttt ggcacccagc tgaaagcgtt tgccgatgac  1440
ttctgctatc acccgctggg tggctgtgtt ctgggtaaag caacggatga ctacggtcgt  1500
gtcgcaggtt ataaaaatct gtacgtgacc gatggctcac tgattccggg ttcggtcggc  1560
gtgaacccgt tcgtgaccat taccgcactg gcagaacgca acgtggaacg cattattaaa  1620
caggatgtca ccgcaagttg a                                             1641
```

<210> SEQ ID NO 23  
<211> LENGTH: 1641  
<212> TYPE: DNA  
<213> ORGANISM: Artificial Sequence  
<220> FEATURE:  
<223> OTHER INFORMATION: Mutant M362R
<400> SEQUENCE: 23

```
atgaccgctc aacaacatct gtcccgccgc cgcatgctgg gtatggccgc ctttggtgcc    60
gccgctctgg caggtggtac gacgattgct gcaccgcgtg cagcagcagc tgcaaaaagc   120
gcagcagata atggcggtta tgttccggcg gtggttattg gtacgggtta cggtgctgca   180
gtgtctgcac tgcgtctggg tgaagccggc gttcagaccc tgatgctgga aatgggtcag   240
ctgtggaacc aaccgggtcc ggacggcaat atcttttgcg gcatgctgaa cccggataaa   300
cgtagctctt ggtttaaaaa ccgcaccgaa gccccgctgg gttctttcct gtggctggac   360
gtcgtgaacc gtaatatcga tccgtatgca ggcgttctgg accgcgtcaa ttatgatcaa   420
```

```
atgagcgttt acgtcggtcg tggtgtgggc ggtggctctc tggttaacgg tggcatggcg      480
gtcgaaccga aacgtagtta ttttgaagaa attctgccgc gcgtcgacag ttccgaaatg      540
tatgatcgtt acttcccgcg cgcgaactcc atgctgcgcg tgaatcatat cgacaccaaa      600
tggtttgaag atacggaatg gtataaattc gcccgtgtga gtcgcgaaca ggccggtaaa      660
gctggcctgg gtaccgtgtt tgttccgaat gtttatgatt tcggttacat gcaacgtgaa      720
gccgcaggcg aagttccgaa aagtgcactg gctaccgaag tcatctatgg taacaatcat      780
ggcaaacagt ccctggacaa aacgtacctg gctgcagcac tgggtaccgg taaagtgacc      840
attcagacgc tgcaccaagt taaaaccatc cgtcagacga agatggtgg ctatgcgctg       900 accgtggaac aaaaagatac ggacggtaaa ctgctggcca cgaaagaaat tagctgtcgc      960
tacctgtttc tgggcgccgg tagtctgggt tccaccgaac tgctggtccg tgcacgtgat     1020
accggtacgc tgccgaacct gaatagcgaa gtgggtgcag gttggggtcc gaacggcaat     1080
attcgtaccg cgcgcgccaa ccatatgtgg aatccgaccg tgcccacca gtcatcgatt     1140 ccggcactgg gcatcgatgc ttgggacaac tcagatagct ctgttttgc ggaaattgcc     1200 ccgatgccgg caggtctgga aacctgggtc tcgctgtatc tggctatcac caaaaatccg     1260
cagcgtggca cgttcgttta cgacgcagct accgatcgtg cgaaactgaa ctggacccgc     1320
gatcaaaacg caccggctgt gaatgcggcc aaagcactgt tgaccgtat taacaaagct      1380 aatggtacga tctatcgcta cgacctgttt ggcacccagc tgaaagcgtt tgccgatgac     1440
ttctgctatc acccgctggg tggctgtgtt ctgggtaaag caacggatga ctacggtcgt     1500
gtcgcaggtt ataaaaatct gtacgtgacc gatggctcac tgattccggg ttcggtcggc     1560
gtgaacccgt tcgtgaccat taccgcactg gcagaacgca acgtggaacg cattattaaa     1620
caggatgtca ccgcaagttg a                                               1641
```

<210> SEQ ID NO 24
<211> LENGTH: 1641
<212> TYPE: DNA
<213> ORGANISM: Artificial Sequence
<220> FEATURE:
<223> OTHER INFORMATION: Mutant M362A
<400> SEQUENCE: 24

```
atgaccgctc aacaacatct gtcccgccgc gcatgctgg gtatggccgc ctttggtgcc       60
gccgctctgg caggtggtac gacgattgct gcaccgcgtg cagcagcagc tgcaaaaagc      120
gcagcagata atggcggtta tgttccggcg gtggttattg gtacgggtta cggtgctgca      180
gtgtctgcac tgcgtctggg tgaagccggc gttcagaccc tgatgctgga aatgggtcag      240
ctgtggaacc aaccgggtcc ggacggcaat atcttttgcg catgctgaa cccggataaa       300 cgtagctctt ggtttaaaaa ccgcaccgaa gccccgctgg ttctttcct gtggctggac       360 gtcgtgaacc gtaatatcga tccgtatgca ggcgttctgg accgcgtcaa ttatgatcaa      420
atgagcgttt acgtcggtcg tggtgtgggc ggtggctctc tggttaacgg tggcatggcg      480
gtcgaaccga aacgtagtta ttttgaagaa attctgccgc gcgtcgacag ttccgaaatg      540
tatgatcgtt acttcccgcg cgcgaactcc atgctgcgcg tgaatcatat cgacaccaaa      600
tggtttgaag atacggaatg gtataaattc gcccgtgtga gtcgcgaaca ggccggtaaa      660
gctggcctgg gtaccgtgtt tgttccgaat gtttatgatt tcggttacat gcaacgtgaa      720
gccgcaggcg aagttccgaa aagtgcactg gctaccgaag tcatctatgg taacaatcat      780
```

| | |
|---|---|
| ggcaaacagt ccctggacaa aacgtacctg gctgcagcac tgggtaccgg taaagtgacc | 840 |
| attcagacgc tgcaccaagt taaaaccatc cgtcagacga agatggtgg ctatgcgctg | 900 |
| accgtggaac aaaaagatac ggacggtaaa ctgctggcca cgaaagaaat tagctgtcgc | 960 |
| tacctgtttc tgggcgccgg tagtctgggt tccaccgaac tgctggtccg tgcacgtgat | 1020 |
| accggtacgc tgccgaacct gaatagcgaa gtgggtgcag gttggggtcc gaacggcaat | 1080 |
| attgcgaccg cgcgcgccaa ccatatgtgg aatccgaccg tgcccacca gtcatcgatt | 1140 |
| ccggcactgg gcatcgatgc ttgggacaac tcagatagct ctgttttgc ggaaattgcc | 1200 |
| ccgatgccgg caggtctgga aacctgggtc tcgctgtatc tggctatcac caaaaatccg | 1260 |
| cagcgtggca cgttcgttta cgacgcagct accgatcgtg cgaaactgaa ctggacccgc | 1320 |
| gatcaaaacg caccggctgt gaatgcggcc aaagcactgt tgaccgtat taacaaagct | 1380 |
| aatggtacga tctatcgcta cgacctgttt ggcacccagc tgaaagcgtt tgccgatgac | 1440 |
| ttctgctatc acccgctggg tggctgtgtt ctgggtaaag caacggatga ctacggtcgt | 1500 |
| gtcgcaggtt ataaaaatct gtacgtgacc gatggctcac tgattccggg ttcggtcggc | 1560 |
| gtgaacccgt tcgtgaccat taccgcactg gcagaacgca acgtggaacg cattattaaa | 1620 |
| caggatgtca ccgcaagttg a | 1641 |

<210> SEQ ID NO 25
<211> LENGTH: 1641
<212> TYPE: DNA
<213> ORGANISM: Artificial Sequence
<220> FEATURE:
<223> OTHER INFORMATION: Mutant M362W

<400> SEQUENCE: 25

| | |
|---|---|
| atgaccgctc aacaacatct gtcccgccgc cgcatgctgg gtatggccgc ctttggtgcc | 60 |
| gccgctctgg caggtggtac gacgattgct gcaccgcgtg cagcagcagc tgcaaaaagc | 120 |
| gcagcagata atggcggtta tgttccggcg gtggttattg gtacgggtta cggtgctgca | 180 |
| gtgtctgcac tgcgtctggg tgaagccggc gttcagaccc tgatgctgga aatgggtcag | 240 |
| ctgtggaacc aaccgggtcc ggacggcaat atcttttgcg gcatgctgaa cccggataaa | 300 |
| cgtagctctt ggtttaaaaa ccgcaccgaa gccccgctgg gttctttcct gtggctggac | 360 |
| gtcgtgaacc gtaatatcga tccgtatgca ggcgttctgg accgcgtcaa ttatgatcaa | 420 |
| atgagcgttt acgtcggtcg tggtgtgggc ggtggctctc tggttaacgg tggcatggcg | 480 |
| gtcgaaccga acgtagtta ttttgaagaa attctgccgc gcgtcgacag ttccgaaatg | 540 |
| tatgatcgtt acttcccgcg cgcgaactcc atgctgcgcg tgaatcatat cgacaccaaa | 600 |
| tggtttgaag atacggaatg gtataaattc gcccgtgtga tcgcgaaca ggccggtaaa | 660 |
| gctggcctgg gtaccgtgtt tgttccgaat gtttatgatt tcggttacat gcaacgtgaa | 720 |
| gccgcaggcg aagttccgaa agtgcactg gctaccgaag tcatctatgg taacaatcat | 780 |
| ggcaaacagt ccctggacaa aacgtacctg gctgcagcac tgggtaccgg taaagtgacc | 840 |
| attcagacgc tgcaccaagt taaaaccatc cgtcagacga agatggtgg ctatgcgctg | 900 |
| accgtggaac aaaaagatac ggacggtaaa ctgctggcca cgaaagaaat tagctgtcgc | 960 |
| tacctgtttc tgggcgccgg tagtctgggt tccaccgaac tgctggtccg tgcacgtgat | 1020 |
| accggtacgc tgccgaacct gaatagcgaa gtgggtgcag gttggggtcc gaacggcaat | 1080 |
| atttggaccg cgcgcgccaa ccatatgtgg aatccgaccg tgcccacca gtcatcgatt | 1140 |
| ccggcactgg gcatcgatgc ttgggacaac tcagatagct ctgttttgc ggaaattgcc | 1200 |

```
ccgatgccgg caggtctgga aacctgggtc tcgctgtatc tggctatcac caaaaatccg    1260
cagcgtggca cgttcgttta cgacgcagct accgatcgtg cgaaactgaa ctggacccgc    1320
gatcaaaacg caccggctgt gaatgcggcc aaagcactgt ttgaccgtat taacaaagct    1380
aatggtacga tctatcgcta cgacctgttt ggcacccagc tgaaagcgtt tgccgatgac    1440
ttctgctatc acccgctggg tggctgtgtt ctgggtaaag caacggatga ctacggtcgt    1500
gtcgcaggtt ataaaaatct gtacgtgacc gatggctcac tgattccggg ttcggtcggc    1560
gtgaacccgt tcgtgaccat taccgcactg gcagaacgca acgtggaacg cattattaaa    1620
caggatgtca ccgcaagttg a                                              1641
```

<210> SEQ ID NO 26
<211> LENGTH: 1641
<212> TYPE: DNA
<213> ORGANISM: Artificial Sequence
<220> FEATURE:
<223> OTHER INFORMATION: Mutant M362P+L412Y

<400> SEQUENCE: 26

```
atgaccgctc aacaacatct gtcccgccgc cgcatgctgg gtatggccgc ctttggtgcc     60
gccgctctgg caggtggtac gacgattgct gcaccgcgtg cagcagcagc tgcaaaaagc    120
gcagcagata tggcggtta tgttccggcg gtggttattg gtacgggtta cggtgctgca    180
gtgtctgcac tgcgtctggg tgaagccggc gttcagaccc tgatgctgga aatgggtcag    240
ctgtggaacc aaccgggtcc ggacggcaat atcttttgcg gcatgctgaa cccggataaa    300
cgtagctctt ggtttaaaaa ccgcaccgaa gccccgctgg gttctttcct gtggctggac    360
gtcgtgaacc gtaatatcga tccgtatgca ggcgttctgg accgcgtcaa ttatgatcaa    420
atgagcgttt acgtcggtcg tggtgtgggc ggtggctctc tggttaacgg tggcatggcg    480
gtcgaaccga acgtagtta ttttgaagaa attctgccgc gcgtcgacag ttccgaaatg    540
tatgatcgtt acttcccgcg cgcgaactcc atgctgcgcg tgaatcatat cgacaccaaa    600
tggtttgaag atacggaatg gtataaattc gcccgtgtga tcgcgaaca ggccggtaaa    660 gctggcctgg gtaccgtgtt tgttccgaat gtttatgatt tcggttacat gcaacgtgaa    720
gccgcaggcg aagttccgaa aagtgcactg gctaccgaag tcatctatgg taacaatcat    780
ggcaaacagt ccctggacaa aacgtacctg gctgcagcac tgggtaccgg taaagtgacc    840
attcagacgc tgcaccaagt taaaaccatc cgtcagacga agatggtgg ctatgcgctg    900 accgtggaac aaaagagatac ggacggtaaa ctgctggcca cgaaagaaat tagctgtcgc    960
tacctgtttc tgggcgccgg tagtctgggt tccaccgaac tgctggtccg tgcacgtgat   1020
accggtacgc tgccgaacct gaatagcgaa gtgggtgcag ttgggggtcc gaacggcaat   1080
attccgaccg cgcgcgccaa ccatatgtgg aatccgaccg tgcccacca gtcatcgatt   1140 ccggcactgg gcatcgatgc ttgggacaac tcagatagcc tgttttttgc ggaaattgcc   1200
ccgatgccgg caggtctgga aacctgggtc tcgtattatc tggctatcac caaaaatccg   1260
cagcgtggca cgttcgttta cgacgcagct accgatcgtg cgaaactgaa ctggacccgc   1320
gatcaaaacg caccggctgt gaatgcggcc aaagcactgt ttgaccgtat taacaaagct   1380
aatggtacga tctatcgcta cgacctgttt ggcacccagc tgaaagcgtt tgccgatgac   1440
ttctgctatc acccgctggg tggctgtgtt ctgggtaaag caacggatga ctacggtcgt   1500
gtcgcaggtt ataaaaatct gtacgtgacc gatggctcac tgattccggg ttcggtcggc   1560
```

| gtgaacccgt tcgtgaccat taccgcactg gcagaacgca acgtggaacg cattattaaa | 1620 |
| caggatgtca ccgcaagttg a | 1641 |

<210> SEQ ID NO 27
<211> LENGTH: 1641
<212> TYPE: DNA
<213> ORGANISM: Artificial Sequence
<220> FEATURE:
<223> OTHER INFORMATION: Mutant M362P+Y483M

<400> SEQUENCE: 27

| atgaccgctc aacaacatct gtcccgccgc cgcatgctgg gtatggccgc ctttggtgcc | 60 |
| gccgctctgg caggtggtac gacgattgct gcaccgcgtg cagcagcagc tgcaaaaagc | 120 |
| gcagcagata atggcggtta tgttccggcg gtggttattg gtacgggtta cggtgctgca | 180 |
| gtgtctgcac tgcgtctggg tgaagccggc gttcagaccc tgatgctgga aatgggtcag | 240 |
| ctgtggaacc aaccgggtcc ggacggcaat atcttttgcg gcatgctgaa cccggataaa | 300 |
| cgtagctctt ggtttaaaaa ccgcaccgaa gccccgctgg ttctttcct gtggctggac | 360 |
| gtcgtgaacc gtaatatcga tccgtatgca ggcgttctgg accgcgtcaa ttatgatcaa | 420 |
| atgagcgttt acgtcggtcg tggtgtgggc ggtggctctc tggttaacgg tggcatggcg | 480 |
| gtcgaaccga acgtagtta ttttgaagaa attctgccgc gcgtcgacag ttccgaaatg | 540 |
| tatgatcgtt acttcccgcg cgcgaactcc atgctgcgcg tgaatcatat cgacaccaaa | 600 |
| tggtttgaag atacggaatg gtataaattc gcccgtgtga gtcgcgaaca ggccggtaaa | 660 |
| gctggcctgg gtaccgtgtt tgttccgaat gtttatgatt tcggttacat gcaacgtgaa | 720 |
| gccgcaggcg aagttccgaa agtgcactg gctaccgaag tcatctatgg taacaatcat | 780 |
| ggcaaacagt ccctggacaa aacgtacctg gctgcagcac tgggtaccgg taaagtgacc | 840 |
| attcagacgc tgcaccaagt taaaaccatc cgtcagacga agatggtgg ctatgcgctg | 900 |
| accgtggaac aaaaagatac ggacggtaaa ctgctggcca cgaaagaaat tagctgtcgc | 960 |
| tacctgttc tgggcgccgg tagtctgggt tccaccgaac tgctggtccg tgcacgtgat | 1020 |
| accggtacgc tgccgaacct gaatagcgaa gtgggtgcag ttgggggtcc gaacggcaat | 1080 |
| attccgaccg cgcgcgccaa ccatatgtgg aatccgaccg gtgcccacca gtcatcgatt | 1140 |
| ccggcactgg gcatcgatgc ttgggacaac tcagatagct ctgtttttgc ggaaattgcc | 1200 |
| ccgatgccgg caggtctgga aacctgggtc tcgctgtatc tggctatcac caaaaatccg | 1260 |
| cagcgtggca cgttcgttta cgacgcagct accgatcgtg cgaaactgaa ctggacccgc | 1320 |
| gatcaaaacg caccggctgt gaatgcggcc aaagcactgt ttgaccgtat taacaaagct | 1380 |
| aatggtacga tctatcgcta cgacctgttt ggcacccagc tgaaagcgtt tgccgatgac | 1440 |
| ttctgcatgc acccgctggg tggctgtgtt ctgggtaaag caacggatga ctacggtcgt | 1500 |
| gtcgcaggtt ataaaaatct gtacgtgacc gatggctcac tgattccggg ttcggtcggc | 1560 |
| gtgaacccgt tcgtgaccat taccgcactg gcagaacgca acgtggaacg cattattaaa | 1620 |
| caggatgtca ccgcaagttg a | 1641 |

<210> SEQ ID NO 28
<211> LENGTH: 1641
<212> TYPE: DNA
<213> ORGANISM: Artificial Sequence
<220> FEATURE:
<223> OTHER INFORMATION: Mutant M362P+Y483W

<400> SEQUENCE: 28

```
atgaccgctc aacaacatct gtcccgccgc cgcatgctgg gtatggccgc ctttggtgcc    60
gccgctctgg caggtggtac gacgattgct gcaccgcgtg cagcagcagc tgcaaaaagc   120
gcagcagata atggcggtta tgttccggcg gtggttattg gtacgggtta cggtgctgca   180
gtgtctgcac tgcgtctggg tgaagccggc gttcagaccc tgatgctgga atgggtcag   240
ctgtggaacc aaccgggtcc ggacggcaat atcttttgcg gcatgctgaa cccggataaa   300
cgtagctctt ggtttaaaaa ccgcaccgaa gccccgctgg gttctttcct gtggctggac   360
gtcgtgaacc gtaatatcga tccgtatgca ggcgttctgg accgcgtcaa ttatgatcaa   420
atgagcgttt acgtcggtcg tggtgtgggc ggtggctctc tggttaacgg tggcatggcg   480
gtcgaaccga acgtagttta ttttgaagaa attctgccgc gcgtcgacag ttccgaaatg   540
tatgatcgtt acttcccgcg cgcgaactcc atgctgcgcg tgaatcatat cgacaccaaa   600
tggtttgaag atacggaatg gtataaattc gcccgtgtga gtcgcgaaca ggccggtaaa   660
gctggcctgg gtaccgtgtt tgttccgaat gtttatgatt tcggttacat gcaacgtgaa   720
gccgcaggcg aagttccgaa agtgcactg gctaccgaag tcatctatgg taacaatcat   780
ggcaaacagt ccctggacaa aacgtacctg gctgcagcac tgggtaccgg taaagtgacc   840
attcagacgc tgcaccaagt taaaaccatc cgtcagacga agatggtgg ctatgcgctg   900
accgtggaac aaaagatac ggacggtaaa ctgctggcca cgaaagaaat tagctgtcgc   960
tacctgtttc tgggcgccgg tagtctgggt tccaccgaac tgctggtccg tgcacgtgat  1020
accggtacgc tgccgaacct gaatagcgaa gtgggtgcag ttggggtcc gaacggcaat  1080
attccgaccg cgcgcgccaa ccatatgtgg aatccgaccg gtgcccacca gtcatcgatt  1140
ccggcactgg gcatcgatgc ttgggacaac tcagatagct ctgttttgc ggaaattgcc  1200
ccgatgccgg caggtctgga aacctgggtc tcgctgtatc tggctatcac caaaaatccg  1260
cagcgtggca cgttcgttta cgacgcagct accgatcgtg cgaaactgaa ctggaccccgc 1320
gatcaaaacg caccggctgt gaatgcggcc aaagcactgt ttgaccgtat taacaaagct  1380
aatggtacga tctatcgcta cgacctgttt ggcacccagc tgaaagcgtt tgccgatgac  1440
ttctgctggc acccgctggg tggctgtgtt ctgggtaaag caacgatga ctacggtcgt   1500
gtcgcaggtt ataaaaatct gtacgtgacc gatggctcac tgattccggg ttcggtcggc  1560
gtgaacccgt tcgtgaccat taccgcactg gcagaacgca acgtggaacg cattattaaa  1620
caggatgtca ccgcaagttg a                                              1641
```

<210> SEQ ID NO 29
<211> LENGTH: 1641
<212> TYPE: DNA
<213> ORGANISM: Artificial Sequence
<220> FEATURE:
<223> OTHER INFORMATION: Mutant M362P+S518G

<400> SEQUENCE: 29

```
atgaccgctc aacaacatct gtcccgccgc cgcatgctgg gtatggccgc ctttggtgcc    60
gccgctctgg caggtggtac gacgattgct gcaccgcgtg cagcagcagc tgcaaaaagc   120
gcagcagata atggcggtta tgttccggcg gtggttattg gtacgggtta cggtgctgca   180
gtgtctgcac tgcgtctggg tgaagccggc gttcagaccc tgatgctgga atgggtcag   240
ctgtggaacc aaccgggtcc ggacggcaat atcttttgcg gcatgctgaa cccggataaa   300
cgtagctctt ggtttaaaaa ccgcaccgaa gccccgctgg gttctttcct gtggctggac   360
```

| | |
|---|---|
| gtcgtgaacc gtaatatcga tccgtatgca ggcgttctgg accgcgtcaa ttatgatcaa | 420 |
| atgagcgttt acgtcggtcg tggtgtgggc ggtggctctc tggttaacgg tggcatggcg | 480 |
| gtcgaaccga aacgtagtta ttttgaagaa attctgccgc gcgtcgacag ttccgaaatg | 540 |
| tatgatcgtt acttcccgcg cgcgaactcc atgctgcgcg tgaatcatat cgacaccaaa | 600 |
| tggtttgaag atacggaatg gtataaattc gcccgtgtga gtcgcgaaca ggccggtaaa | 660 |
| gctggcctgg gtaccgtgtt tgttccgaat gtttatgatt tcggttacat gcaacgtgaa | 720 |
| gccgcaggcg aagttccgaa aagtgcactg gctaccgaag tcatctatgg taacaatcat | 780 |
| ggcaaacagt ccctggacaa aacgtacctg gctgcagcac tgggtaccgg taaagtgacc | 840 |
| attcagacgc tgcaccaagt taaaaccatc cgtcagacga agatggtgg ctatgcgctg | 900 |
| accgtggaac aaaagatac ggacggtaaa ctgctggcca cgaaagaaat tagctgtcgc | 960 |
| tacctgtttc tgggcgccgg tagtctgggt tccaccgaac tgctggtccg tgcacgtgat | 1020 |
| accggtacgc tgccgaacct gaatagcgaa gtgggtgcag gttggggtcc gaacggcaat | 1080 |
| attccgaccg cgcgcgccaa ccatatgtgg aatccgaccg tgcccaccca gtcatcgatt | 1140 |
| ccggcactgg gcatcgatgc ttgggacaac tcagatagct ctgttttgc ggaaattgcc | 1200 |
| ccgatgccgc aggtctgga aacctgggtc tcgctgtatc tggctatcac caaaaatccg | 1260 |
| cagcgtggca cgttcgttta cgacgcagct accgatcgtg cgaaactgaa ctggacccgc | 1320 |
| gatcaaaacg caccggctgt gaatgcgccc aaagcactgt tgaccgtat aacaaagct | 1380 |
| aatggtacga tctatcgcta cgacctgttt ggcacccagc tgaaagcgtt tgccgatgac | 1440 |
| ttctgctatc acccgctggg tggctgtgtt ctgggtaaag caacggatga ctacggtcgt | 1500 |
| gtcgcaggtt ataaaaatct gtacgtgacc gatggctcac tgattccggg tggcgtcggc | 1560 |
| gtgaacccgt tcgtgaccat taccgcactg gcagaacgca acgtggaacg cattattaaa | 1620 |
| caggatgtca ccgcaagttg a | 1641 |

<210> SEQ ID NO 30
<211> LENGTH: 1641
<212> TYPE: DNA
<213> ORGANISM: Artificial Sequence
<220> FEATURE:
<223> OTHER INFORMATION: Mutant M362P+S518L

<400> SEQUENCE: 30

| | |
|---|---|
| atgaccgctc aacaacatct gtcccgccgc cgcatgctgg gtatggccgc ctttggtgcc | 60 |
| gccgctctgg caggtggtac gacgattgct gcaccgcgtg cagcagcagc tgcaaaaagc | 120 |
| gcagcagata atggcggtta tgttccggcg gtggttattg gtacgggtta cggtgctgca | 180 |
| gtgtctgcac tgcgtctggg tgaagccggc gttcagaccc tgatgctgga atgggtcag | 240 |
| ctgtggaacc aacggggtcc ggacggcaat atctttgcg gcatgctgaa cccggataaa | 300 |
| cgtagctctt ggtttaaaaa ccgcaccgaa gccccgctgg gttctttcct gtggctggac | 360 |
| gtcgtgaacc gtaatatcga tccgtatgca ggcgttctgg accgcgtcaa ttatgatcaa | 420 |
| atgagcgttt acgtcggtcg tggtgtgggc ggtggctctc tggttaacgg tggcatggcg | 480 |
| gtcgaaccga aacgtagtta ttttgaagaa attctgccgc gcgtcgacag ttccgaaatg | 540 |
| tatgatcgtt acttcccgcg cgcgaactcc atgctgcgcg tgaatcatat cgacaccaaa | 600 |
| tggtttgaag atacggaatg gtataaattc gcccgtgtga gtcgcgaaca ggccggtaaa | 660 |
| gctggcctgg gtaccgtgtt tgttccgaat gtttatgatt tcggttacat gcaacgtgaa | 720 |
| gccgcaggcg aagttccgaa aagtgcactg gctaccgaag tcatctatgg taacaatcat | 780 |

```
ggcaaacagt ccctggacaa aacgtacctg gctgcagcac tgggtaccgg taaagtgacc      840
attcagacgc tgcaccaagt taaaaccatc cgtcagacga agatggtgg ctatgcgctg       900 accgtggaac aaaaagatac ggacggtaaa ctgctggcca cgaaagaaat tagctgtcgc      960
tacctgtttc tgggcgccgg tagtctgggt tccaccgaac tgctggtccg tgcacgtgat     1020
accggtacgc tgccgaacct gaatagcgaa gtgggtgcag gttggggtcc gaacggcaat     1080
attccgaccg cgcgcgccaa ccatatgtgg aatccgaccg gtgcccacca gtcatcgatt     1140
ccggcactgg gcatcgatgc ttgggacaac tcagatagct ctgttttttgc ggaaattgcc    1200 ccgatgccgg caggtctgga aacctgggtc tcgctgtatc tggctatcac caaaaatccg     1260
cagcgtggca cgttcgttta cgacgcagct accgatcgtg cgaaactgaa ctggacccgc     1320
gatcaaaacg caccggctgt gaatgcggcc aaagcactgt ttgaccgtat taacaaagct     1380
aatggtacga tctatcgcta cgacctgttt ggcacccagc tgaaagcgtt tgccgatgac     1440
ttctgctatc acccgctggg tggctgtgtt ctgggtaaag caacggatga ctacggtcgt     1500
gtcgcaggtt ataaaaatct gtacgtgacc gatggctcac tgattccggg tctggtcggc     1560
gtgaacccgt tcgtgaccat taccgcactg cagaacgca acgtggaacg cattattaaa     1620
caggatgtca ccgcaagttg a                                              1641
```

<210> SEQ ID NO 31
<211> LENGTH: 1641
<212> TYPE: DNA
<213> ORGANISM: Artificial Sequence
<220> FEATURE:
<223> OTHER INFORMATION: Mutant M362P+S518T

<400> SEQUENCE: 31

```
atgaccgctc aacaacatct gtcccgccgc cgcatgctgg gtatggccgc ctttggtgcc       60
gccgctctgg caggtggtac gacgattgct gcaccgcgtg cagcagcagc tgcaaaaagc      120
gcagcagata atgcggttta tgttccggcg gtggttattg gtacgggtta cggtgctgca      180
gtgtctgcac tgcgtctggg tgaagccggc gttcagaccc tgatgctgga aatgggtcag      240
ctgtggaacc aaccgggtcc ggacggcaat atcttttgcg gcatgctgaa cccggataaa      300
cgtagctctt ggtttaaaaa ccgcaccgaa gccccgctgg gttctttcct gtggctggac      360
gtcgtgaacc gtaatatcga tccgtatgca ggcgttctgg accgcgtcaa ttatgatcaa      420
atgagcgttt acgtcggtcg tggtgtgggc ggtggctctc tggttaacgg tggcatggcg      480
gtcgaaccga acgtagtta ttttgaagaa attctgccgc gcgtcgacag ttccgaaatg      540
tatgatcgtt acttcccgcg cgcgaactcc atgctgcgcg tgaatcatat cgacaccaaa      600
tggtttgaag atacggaatg gtataaattc gcccgtgtga tcgcgaaca ggccggtaaa      660 gctggcctgg gtaccgtgtt tgttccgaat gtttatgatt tcggttacat gcaacgtgaa      720
gccgcaggcg aagttccgaa aagtgcactg gctaccgaag tcatctatgg taacaatcat      780
ggcaaacagt ccctggacaa aacgtacctg gctgcagcac tgggtaccgg taaagtgacc      840
attcagacgc tgcaccaagt taaaaccatc cgtcagacga agatggtgg ctatgcgctg       900 accgtggaac aaaaagatac ggacggtaaa ctgctggcca cgaaagaaat tagctgtcgc      960
tacctgtttc tgggcgccgg tagtctgggt tccaccgaac tgctggtccg tgcacgtgat     1020
accggtacgc tgccgaacct gaatagcgaa gtgggtgcag gttggggtcc gaacggcaat     1080
attccgaccg cgcgcgccaa ccatatgtgg aatccgaccg gtgcccacca gtcatcgatt     1140
```

```
ccggcactgg gcatcgatgc ttgggacaac tcagatagct ctgttttgc ggaaattgcc      1200 ccgatgccgg caggtctgga aacctgggtc tcgctgtatc tggctatcac caaaaatccg      1260
cagcgtggca cgttcgttta cgacgcagct accgatcgtg cgaaactgaa ctggacccgc      1320
gatcaaaacg caccggctgt gaatgcggcc aaagcactgt ttgaccgtat taacaaagct      1380
aatggtacga tctatcgcta cgacctgttt ggcacccagc tgaaagcgtt tgccgatgac      1440
ttctgctatc acccgctggg tggctgtgtt ctgggtaaag caacggatga ctacggtcgt      1500
gtcgcaggtt ataaaaatct gtacgtgacc gatggctcac tgattccggg taccgtcggc      1560
gtgaacccgt tcgtgaccat taccgcactg gcagaacgca acgtggaacg cattattaaa      1620
caggatgtca ccgcaagttg a                                              1641

<210> SEQ ID NO 32
<211> LENGTH: 1641
<212> TYPE: DNA
<213> ORGANISM: Artificial Sequence
<220> FEATURE:
<223> OTHER INFORMATION: Mutant M362P+S518A

<400> SEQUENCE: 32
atgaccgctc aacaacatct gtcccgccgc cgcatgctgg gtatggccgc ctttggtgcc       60
gccgctctgg caggtggtac gacgattgct gcaccgcgtg cagcagcagc tgcaaaaagc      120
gcagcagata atggcggtta tgttccggcg gtggttattg gtacgggtta cggtgctgca      180
gtgtctgcac tgcgtctggg tgaagccggc gttcagaccc tgatgctgga aatgggtcag      240
ctgtggaacc aaccgggtcc ggacggcaat atcttttgcg catgctgaa cccggataaa       300 cgtagctctt ggttttaaaaa ccgcaccgaa gccccgctgg ttctttcct gtggctggac     360 gtcgtgaacc gtaatatcga tccgtatgca ggcgttctgg accgcgtcaa ttatgatcaa      420
atgagcgttt acgtcggtcg tggtgtgggc ggtggctctc tggttaacgg tggcatggcg      480
gtcgaaccga acgtagtta ttttgaagaa attctgccgc gcgtcgacag ttccgaaatg       540
tatgatcgtt acttcccgcg cgcgaactcc atgctgcgcg tgaatcatat cgacaccaaa      600
tggtttgaag atacggaatg gtataaattc gcccgtgtga tcgcgaaaca ggccggtaaa      660
gctggcctgg gtaccgtgtt tgttccgaat gtttatgatt tcggttacat gcaacgtgaa      720
gccgcaggcg aagttccgaa agtgcactg gctaccgaag tcatctatgg taacaatcat      780
ggcaaacagt ccctggacaa aacgtacctg gctgcagcac tgggtaccgg taaagtgacc      840
attcagacgc tgcaccaagt taaaaccatc cgtcagacga agatggtgg ctatgcgctg      900 accgtggaac aaaaagatac ggacggtaaa ctgctggcca cgaaagaaat tagctgtcgc      960
tacctgtttc tgggcgccgg tagtctgggt tccaccgaac tgctggtccg tgcacgtgat     1020
accggtacgc tgccgaacct gaatagcgaa gtgggtgcag gttggggtcc gaacggcaat     1080
attccgaccg cgcgccaa ccatatgtgg aatccgaccg tgcccacca gtcatcgatt     1140 ccggcactgg gcatcgatgc ttgggacaac tcagatagct ctgttttgc ggaaattgcc      1200 ccgatgccgg caggtctgga aacctgggtc tcgctgtatc tggctatcac caaaaatccg      1260
cagcgtggca cgttcgttta cgacgcagct accgatcgtg cgaaactgaa ctggacccgc      1320
gatcaaaacg caccggctgt gaatgcggcc aaagcactgt ttgaccgtat taacaaagct      1380
aatggtacga tctatcgcta cgacctgttt ggcacccagc tgaaagcgtt tgccgatgac      1440
ttctgctatc acccgctggg tggctgtgtt ctgggtaaag caacggatga ctacggtcgt      1500
gtcgcaggtt ataaaaatct gtacgtgacc gatggctcac tgattccggg tgcggtcggc      1560
```

<210> SEQ ID NO 33
<211> LENGTH: 1641
<212> TYPE: DNA
<213> ORGANISM: Artificial Sequence
<220> FEATURE:
<223> OTHER INFORMATION: Mutant M362P+V519C

<400> SEQUENCE: 33

```
atgaccgctc aacaacatct gtcccgccgc cgcatgctgg gtatggccgc ctttggtgcc      60
gccgctctgg caggtggtac gacgattgct gcaccgcgtg cagcagcagc tgcaaaaagc     120
gcagcagata atggcggtta tgttccggcg gtggttattg gtacgggtta cggtgctgca     180
gtgtctgcac tgcgtctggg tgaagccggc gttcagaccc tgatgctgga aatgggtcag     240
ctgtggaacc aaccgggtcc ggacggcaat atcttttgcg gcatgctgaa cccggataaa     300
cgtagctctt ggtttaaaaa ccgcaccgaa gccccgctgg ttctttcct gtggctggac      360
gtcgtgaacc gtaatatcga tccgtatgca ggcgttctgg accgcgtcaa ttatgatcaa     420
atgagcgttt acgtcggtcg tggtgtgggc ggtggctctc tggttaacgg tggcatggcg     480
gtcgaaccga acgtagttta ttttgaagaa attctgccgc gcgtcgacag ttccgaaatg     540
tatgatcgtt acttcccgcg cgcgaactcc atgctgcgcg tgaatcatat cgacaccaaa     600
tggtttgaag atacggaatg gtataaattc gcccgtgtga gtcgcgaaca ggccggtaaa     660
gctggcctgg gtaccgtgtt tgttccgaat gtttatgatt tcggttacat gcaacgtgaa     720
gccgcaggcg aagttccgaa aagtgcactg gctaccgaag tcatctatgg taacaatcat     780
ggcaaacagt ccctggacaa aacgtacctg gctgcagcac tgggtaccgg taaagtgacc     840
attcagacgc tgcaccaagt taaaaccatc cgtcagacga agatggtgg ctatgcgctg      900
accgtggaac aaaaagatac ggacggtaaa ctgctggcca cgaaagaaat tagctgtcgc     960
tacctgtttc tgggcgccgg tagtctgggt tccaccgaac tgctggtccg tgcacgtgat    1020
accggtacgc tgccgaacct gaatagcgaa gtgggtgcag ttggggtcc gaacggcaat     1080
attccgaccg cgcgcgccaa ccatatgtgg aatccgaccg tgcccacca gtcatcgatt     1140
ccggcactgg gcatcgatgc ttgggacaac tcagatagct ctgtttttgc ggaaattgcc    1200
ccgatgccgg caggtctgga aacctgggtc tcgctgtatc tggctatcac caaaaatccg    1260
cagcgtggca cgttcgttta cgacgcagct accgatcgtg cgaaactgaa ctggacccgc    1320
gatcaaaacg caccggctgt gaatgcggcc aaagcactgt ttgaccgtat taacaaagct    1380
aatggtacga tctatcgcta cgacctgttt ggcacccagc tgaaagcgtt tgccgatgac    1440
ttctgctatc acccgctggg tggctgtgtt ctgggtaaag caacggatga ctacggtcgt    1500
gtcgcaggtt ataaaaatct gtacgtgacc gatggctcac tgattccggg ttcgtgcggc    1560
gtgaacccgt tcgtgaccat taccgcactg gcagaacgca acgtggaacg cattattaaa    1620
caggatgtca ccgcaagttg a                                              1641
```

<210> SEQ ID NO 34
<211> LENGTH: 1641
<212> TYPE: DNA
<213> ORGANISM: Artificial Sequence
<220> FEATURE:
<223> OTHER INFORMATION: Mutant M362P+V519I

<400> SEQUENCE: 34

```
atgaccgctc aacaacatct gtcccgccgc cgcatgctgg gtatggccgc ctttggtgcc      60
gccgctctgg caggtggtac gacgattgct gcaccgcgtg cagcagcagc tgcaaaaagc     120
gcagcagata atggcggtta tgttccggcg gtggttattg gtacgggtta cggtgctgca     180
gtgtctgcac tgcgtctggg tgaagccggc gttcagaccc tgatgctgga aatgggtcag     240
ctgtggaacc aaccgggtcc ggacggcaat atcttttgcg gcatgctgaa cccggataaa     300
cgtagctctt ggtttaaaaa ccgcaccgaa gccccgctgg gttctttcct gtggctggac     360
gtcgtgaacc gtaatatcga tccgtatgca ggcgttctgg accgcgtcaa ttatgatcaa     420
atgagcgttt acgtcggtcg tggtgtgggc ggtggctctc tggttaacgg tggcatggcg     480
gtcgaaccga acgtagtta ttttgaagaa attctgccgc gcgtcgacag ttccgaaatg     540
tatgatcgtt acttcccgcg cgcgaactcc atgctgcgcg tgaatcatat cgacaccaaa     600
tggtttgaag atacggaatg gtataaattc gcccgtgtga gtcgcgaaca ggccggtaaa     660
gctggcctgg gtaccgtgtt tgttccgaat gtttatgatt tcggttacat gcaacgtgaa     720
gccgcaggcg aagttccgaa aagtgcactg gctaccgaag tcatctatgg taacaatcat     780
ggcaaacagt ccctggacaa aacgtacctg gctgcagcac tgggtaccgg taaagtgacc     840
attcagacgc tgcaccaagt taaaaccatc cgtcagacga agatggtgg ctatgcgctg     900
accgtggaac aaaaagatac ggacggtaaa ctgctggcca gaaagaaat tagctgtcgc     960
tacctgtttc tgggcgccgg tagtctgggt tccaccgaac tgctggtccg tgcacgtgat    1020
accggtacgc tgccgaacct gaatagcgaa gtgggtgcag ttggggtcc gaacggcaat    1080
attccgaccg cgcgcgccaa ccatatgtgg aatccgaccg tgcccacca gtcatcgatt    1140
ccggcactgg gcatcgatgc ttgggacaac tcagatagct ctgttttgc ggaaattgcc    1200
ccgatgccgg caggtctgga aacctgggtc tcgctgtatc tggctatcac caaaaatccg    1260
cagcgtggca cgttcgttta cgacgcagct accgatcgtg cgaaactgaa ctggacccgc    1320
gatcaaaacg caccggctgt gaatgcggcc aaagcactgt ttgaccgtat taacaaagct    1380
aatggtacga tctatcgcta cgacctgttt ggcacccagc tgaaagcgtt tgccgatgac    1440
ttctgctatc acccgctggg tggctgtgtt ctgggtaaag caacggatga ctacggtcgt    1500
gtcgcaggtt ataaaaatct gtacgtgacc gatggctcac tgattccggg ttcgattggc    1560
gtgaacccgt tcgtgaccat taccgcactg gcagaacgca acgtggaacg cattattaaa    1620
caggatgtca ccgcaagttg a                                              1641
```

<210> SEQ ID NO 35
<211> LENGTH: 1641
<212> TYPE: DNA
<213> ORGANISM: Artificial Sequence
<220> FEATURE:
<223> OTHER INFORMATION: Mutant M362P+V519S

<400> SEQUENCE: 35

```
atgaccgctc aacaacatct gtcccgccgc cgcatgctgg gtatggccgc ctttggtgcc      60
gccgctctgg caggtggtac gacgattgct gcaccgcgtg cagcagcagc tgcaaaaagc     120
gcagcagata atggcggtta tgttccggcg gtggttattg gtacgggtta cggtgctgca     180
gtgtctgcac tgcgtctggg tgaagccggc gttcagaccc tgatgctgga aatgggtcag     240
ctgtggaacc aaccgggtcc ggacggcaat atcttttgcg gcatgctgaa cccggataaa     300
cgtagctctt ggtttaaaaa ccgcaccgaa gccccgctgg gttctttcct gtggctggac     360
```

```
gtcgtgaacc gtaatatcga tccgtatgca ggcgttctgg accgcgtcaa ttatgatcaa    420
atgagcgttt acgtcggtcg tggtgtgggc ggtggctctc tggttaacgg tggcatggcg    480
gtcgaaccga aacgtagtta ttttgaagaa attctgccgc gcgtcgacag ttccgaaatg    540
tatgatcgtt acttcccgcg cgcgaactcc atgctgcgcg tgaatcatat cgacaccaaa    600
tggtttgaag atacggaatg gtataaattc gcccgtgtga gtcgcgaaca ggccggtaaa    660
gctggcctgg gtaccgtgtt tgttccgaat gtttatgatt tcggttacat gcaacgtgaa    720
gccgcaggcg aagttccgaa aagtgcactg gctaccgaag tcatctatgg taacaatcat    780
ggcaaacagt ccctggacaa aacgtacctg gctgcagcac tgggtaccgg taaagtgacc    840
attcagacgc tgcaccaagt taaaaccatc cgtcagacga agatggtgg ctatgcgctg    900 accgtggaac aaaaagatac ggacggtaaa ctgctggcca cgaaagaaat tagctgtcgc    960
tacctgtttc tgggcgccgg tagtctgggt tccaccgaac tgctggtccg tgcacgtgat   1020
accggtacgc tgccgaacct gaatagcgaa gtgggtgcag gttggggtcc gaacggcaat   1080
attccgaccg cgcgcgccaa ccatatgtgg aatccgaccg tgcccacca gtcatcgatt   1140 ccggcactgg gcatcgatgc ttgggacaac tcagatagct ctgttttgc ggaaattgcc   1200 ccgatgccgg caggtctgga aacctgggtc tcgctgtatc tggctatcac caaaaatccg   1260
cagcgtggca cgttcgttta cgacgcagct accgatcgtg cgaaactgaa ctggaccccgc   1320 gatcaaaacg caccggctgt gaatgcggcc aaagcactgt ttgaccgtat taacaaagct   1380
aatggtacga tctatcgcta cgacctgttt ggcacccagc tgaaagcgtt tgccgatgac   1440
ttctgctatc acccgctggg tggctgtgtt ctgggtaaag caacggatga ctacggtcgt   1500
gtcgcaggtt ataaaaatct gtacgtgacc gatggctcac tgattccggg ttcgagcggc   1560
gtgaacccgt tcgtgaccat taccgcactg gcagaacgca acgtggaacg cattattaaa   1620
caggatgtca ccgcaagttg a                                            1641

<210> SEQ ID NO 36
<211> LENGTH: 1641
<212> TYPE: DNA
<213> ORGANISM: Artificial Sequence
<220> FEATURE:
<223> OTHER INFORMATION: Mutant M362P+V519T

<400> SEQUENCE: 36
atgaccgctc aacaacatct gtcccgccgc cgcatgctgg gtatggccgc ctttggtgcc     60
gccgctctgg caggtggtac gacgattgct gcaccgcgtg cagcagcagc tgcaaaaagc    120
gcagcagata tggcggtta tgttccggcg gtggttattg gtacgggtta cggtgctgca    180
gtgtctgcac tgcgtctggg tgaagccggc gttcagaccc tgatgctgga aatgggtcag    240
ctgtggaacc aaccgggtcc ggacggcaat atctttttgcg gcatgctgaa cccggataaa    300
cgtagctctt ggtttaaaaa ccgcaccgaa gccccgctgg ttctttcct gtggctggac    360 gtcgtgaacc gtaatatcga tccgtatgca ggcgttctgg accgcgtcaa ttatgatcaa    420
atgagcgttt acgtcggtcg tggtgtgggc ggtggctctc tggttaacgg tggcatggcg    480
gtcgaaccga aacgtagtta ttttgaagaa attctgccgc gcgtcgacag ttccgaaatg    540
tatgatcgtt acttcccgcg cgcgaactcc atgctgcgcg tgaatcatat cgacaccaaa    600
tggtttgaag atacggaatg gtataaattc gcccgtgtga gtcgcgaaca ggccggtaaa    660
gctggcctgg gtaccgtgtt tgttccgaat gtttatgatt tcggttacat gcaacgtgaa    720
```

```
gccgcaggcg aagttccgaa aagtgcactg gctaccgaag tcatctatgg taacaatcat    780
ggcaaacagt ccctggacaa aacgtacctg gctgcagcac tgggtaccgg taaagtgacc    840
attcagacgc tgcaccaagt taaaaccatc cgtcagacga agatggtgg ctatgcgctg     900 accgtggaac aaaagatac ggacggtaaa ctgctggcca cgaaagaaat tagctgtcgc    960
tacctgtttc tgggcgccgg tagtctgggt tccaccgaac tgctggtccg tgcacgtgat   1020
accggtacgc tgccgaacct gaatagcgaa gtgggtgcag gttggggtcc gaacggcaat   1080
attccgaccg cgcgcgccaa ccatatgtgg aatccgaccg gtgcccacca gtcatcgatt   1140
ccggcactgg gcatcgatgc ttgggacaac tcagatagct ctgtttttgc ggaaattgcc   1200
ccgatgccgg caggtctgga acctgggtc tcgctgtatc tggctatcac caaaaatccg    1260
cagcgtggca cgttcgttta cgacgcagct accgatcgtg cgaaactgaa ctggaccccgc  1320 gatcaaaacg caccggctgt gaatgcggcc aaagcactgt ttgaccgtat taacaaagct  1380
aatggtacga tctatcgcta cgacctgttt ggcacccagc tgaaagcgtt tgccgatgac   1440
ttctgctatc acccgctggg tggctgtgtt ctgggtaaag caacgatga ctacggtcgt    1500 gtcgcaggtt ataaaaatct gtacgtgacc gatggctcac tgattccggg ttcgaccggc   1560
gtgaacccgt tcgtgaccat taccgcactg gcagaacgca acgtggaacg cattattaaa   1620
caggatgtca ccgcaagttg a                                             1641
```

<210> SEQ ID NO 37
<211> LENGTH: 553
<212> TYPE: PRT
<213> ORGANISM: Streptomyces albulus

<400> SEQUENCE: 37

Met Phe Glu Asn Gln Gln Asn Gln His Leu Ser Arg Arg Arg Leu Leu
1               5                   10                  15

Gly Leu Ala Ala Leu Ser Gly Ala Ala Val Thr Gly Leu Thr Thr Ile
            20                  25                  30

Ser Ala Ala Pro Arg Ala Ala Ala Asp Lys Arg Ser Pro Arg Ala
        35                  40                  45

Asp Ser Gly Ser Leu Val Pro Ala Val Ile Gly Thr Gly Tyr Gly
    50                  55                  60

Ala Ala Val Ser Ala Leu Arg Leu Gly Glu Ala Gly Val Glu Thr Leu
65                  70                  75                  80

Met Leu Glu Met Gly Gln Leu Trp Asn Lys Pro Ala Glu Asp Gly Asn
                85                  90                  95

Val Phe Cys Gly Met Leu Thr Pro Asp Arg Arg Ser Ser Trp Phe Lys
            100                 105                 110

Ser Arg Thr Glu Ala Pro Leu Gly Ser Phe Leu Trp Leu Asp Val Ile
        115                 120                 125

Asn Arg Asp Ile Glu Pro Tyr Ala Gly Val Leu Asp Arg Val His Phe
    130                 135                 140

Asp Gln Met Ser Val Tyr Val Gly Arg Gly Val Gly Gly Gly Ser Leu
145                 150                 155                 160

Val Asn Gly Gly Met Ala Val Val Pro Lys Arg Ala Tyr Phe Glu Glu
                165                 170                 175

Val Leu Pro Gln Val Asp Ala Ala Gln Met Tyr Glu Arg Tyr Phe Pro
            180                 185                 190

Arg Ala Asn Ala Ala Leu Lys Val Asn His Ile Asp Pro Ala Trp Phe
        195                 200                 205

```
Glu Lys Thr Glu Trp Tyr Asn Phe Ala Arg Val Ser Arg Glu Gln Ala
210                 215                 220

Gly Lys Ala Gly Leu Ser Thr Thr Phe Val Pro Asn Val Tyr Asp Phe
225                 230                 235                 240

Asp His Met Gln Arg Glu Ala Ala Gly Thr Ala Pro Lys Ser Ala Leu
                245                 250                 255

Ala Gly Glu Val Ile Tyr Gly Asn Asn His Gly Lys Gln Ser Leu Asp
                260                 265                 270

Lys Thr Tyr Leu Ala Ala Ala Leu Gly Thr Gly Lys Val Thr Ile Glu
                275                 280                 285

Thr Leu His Arg Val Thr Ala Ile Arg Gln Gln Ala Asp Gly Ser Tyr
290                 295                 300

Val Leu Ser Val Asp Gln Ser Asp Ala Asn Gly Thr Val Ile Ala His
305                 310                 315                 320

Lys Glu Ile Ala Cys Arg His Leu Phe Leu Gly Ala Gly Ser Leu Gly
                325                 330                 335

Ser Thr Glu Leu Leu Val Arg Ala Arg Asp Thr Gly Ala Leu Pro His
                340                 345                 350

Leu Asn Ala Glu Val Gly Glu Gly Trp Gly Pro Asn Gly Asn Ile Met
                355                 360                 365

Thr Gly Arg Ala Asn His Val Trp Asn Pro Thr Gly Ala His Gln Ser
370                 375                 380

Ser Ile Pro Ala Leu Gly Ile Asp Asp Trp Asp Asn Pro Asp Ala Pro
385                 390                 395                 400

Val Phe Ala Glu Ile Ala Pro Met Pro Ala Gly Leu Glu Thr Trp Val
                405                 410                 415

Ser Leu Tyr Leu Ala Ile Thr Lys Asn Pro Glu Arg Gly Ser Phe Val
                420                 425                 430

Tyr Asp Lys Ala Thr Asp Arg Ala Met Leu Arg Trp Thr Arg Glu Gln
                435                 440                 445

Asn Ala Pro Ala Val Ala Ala Lys Ser Leu Phe Asp Arg Ile Asn
450                 455                 460

Lys Ala Asn Thr Thr Met Tyr Arg Tyr Asp Leu Phe Gly Pro Gln Leu
465                 470                 475                 480

Lys Asn Phe Ala Asp Asp Phe Cys Tyr His Pro Leu Gly Gly Cys Val
                485                 490                 495

Leu Gly Lys Ala Thr Asp Asp Tyr Gly Arg Val Ala Gly Tyr His Asn
                500                 505                 510

Leu Tyr Val Thr Asp Gly Ala Leu Ile Pro Gly Ser Ile Gly Val Asn
                515                 520                 525

Pro Phe Val Thr Ile Thr Ala Leu Ala Glu Arg Asn Ile Glu Arg Val
530                 535                 540

Ile Ala Glu Asp Val Arg Thr Ala Ala
545                 550

<210> SEQ ID NO 38
<211> LENGTH: 542
<212> TYPE: PRT
<213> ORGANISM: Streptomyces virginiae

<400> SEQUENCE: 38

Met Glu Gln His Leu Ser Arg Arg Leu Leu Gly Met Thr Ala Leu
1               5                   10                  15

Gly Ala Ala Ala Leu Ala Gly Ser Thr Thr Ile Gly Ala Pro Arg Ala
                20                  25                  30
```

```
Leu Ala Ala Asp Arg Ala Asp Gly Val Ala Phe Phe Pro Ala Val Val
        35                  40                  45

Ile Gly Thr Gly Tyr Gly Ala Ala Val Ser Ala Leu Arg Leu Gly Glu
    50                  55                  60

Ala Gly Val Arg Thr Val Met Leu Glu Met Gly Gln Leu Trp Asn Gln
65                  70                  75                  80

Pro Gly Pro Asp Gly Asn Val Phe Ala Gly Met Leu Lys Pro Asp Lys
                85                  90                  95

Arg Ser Ser Trp Phe Lys Asn Arg Thr Glu Ala Pro Leu Gly Ser Phe
                100                 105                 110

Leu Trp Leu Asp Leu Ala Asn Arg Asp Ile Asp Pro Tyr Ala Gly Val
            115                 120                 125

Leu Asp Arg Val Asn Phe Asp Gln Met Ser Val Tyr Val Gly Arg Gly
130                 135                 140

Val Gly Gly Ser Leu Val Asn Gly Gly Met Ala Val Ala Pro Lys
145                 150                 155                 160

Arg Ser Tyr Phe Glu Glu Val Leu Pro Arg Val Asp Ser Ala Glu Met
                165                 170                 175

Tyr Ser Arg Tyr Phe Pro Arg Ala Asn Ser Met Leu Arg Val Asn His
            180                 185                 190

Ile Asp Asp Gly Trp Phe Glu Ser Thr Glu Trp Tyr Lys Phe Ala Arg
        195                 200                 205

Val Ser Arg Asp Gln Ala Gln Lys Ala Gly Leu Gly Thr Val His Val
210                 215                 220

Pro Asn Val Tyr Asp Phe Asp His Met Arg Arg Glu Ala Ala Gly Glu
225                 230                 235                 240

Ala Pro Lys Ser Ala Leu Ala Gly Glu Val Ile Tyr Gly Asn Asn His
            245                 250                 255

Gly Lys Gln Ser Leu Asp Lys Thr Tyr Leu Ala Ala Ala Leu Gly Thr
            260                 265                 270

Gly Lys Val Thr Ile Glu Thr Leu His Gln Ala Arg Thr Ile Arg Gln
            275                 280                 285

Gln Lys Asp Gly Thr Tyr Leu Leu Thr Val Glu Gln Arg Asp Ala Asp
            290                 295                 300

Gly Arg Leu Leu Ala Thr Lys Glu Ile Ser Cys Arg His Leu Phe Leu
305                 310                 315                 320

Gly Ala Gly Ser Leu Gly Ser Thr Glu Leu Leu Arg Ala Arg Glu
                325                 330                 335

Thr Gly Thr Leu Pro Asp Leu Ser Ser Glu Ile Gly Ala Gly Trp Gly
            340                 345                 350

Pro Asn Gly Asn Ile Met Thr Ala Arg Ala Asn His Val Trp Asn Pro
            355                 360                 365

Thr Gly Ala Asn Gln Ser Ser Ile Pro Ala Leu Gly Ile Asp Asp Trp
    370                 375                 380

Asp Asn Pro Gln Asn Pro Val Phe Ala Glu Ile Ala Pro Met Pro Ala
385                 390                 395                 400

Gly Leu Glu Thr Trp Val Ser Leu Tyr Leu Ala Ile Thr Lys Asn Pro
                405                 410                 415

Glu Arg Gly Thr Phe Ala Tyr Asp Ala Ala Thr Asp Arg Ala Ala Leu
                420                 425                 430

Arg Trp Thr Arg Asp Gln Asn Thr Pro Ala Val Ser Ala Ala Lys Ser
            435                 440                 445
```

```
Leu Phe Asp Arg Ile Asn Lys Ala Asn Thr Thr Met Tyr Arg Tyr Asp
    450                 455                 460

Leu Phe Gly Lys Gln Leu Lys Ala Phe Ser Asp Asp Phe Thr Tyr His
465                 470                 475                 480

Pro Leu Gly Gly Cys Val Leu Gly Arg Ala Thr Asp Asp Tyr Gly Arg
                485                 490                 495

Val Lys Gly Tyr Lys Asn Leu Tyr Val Thr Asp Gly Ser Leu Ile Pro
                500                 505                 510

Gly Ser Ile Gly Val Asn Pro Phe Val Thr Ile Thr Ala Leu Ala Glu
            515                 520                 525

Arg Asn Ile Glu Arg Val Ile Arg Gln Asp Val Thr Ala Ala
530                 535                 540

<210> SEQ ID NO 39
<211> LENGTH: 533
<212> TYPE: PRT
<213> ORGANISM: Streptomyces lavendulae

<400> SEQUENCE: 39

Met Leu Gly Leu Ala Ala Leu Gly Ala Ala Ala Met Ala Gly Ser Thr
1               5                   10                  15

Thr Ile Gly Ala Thr Arg Ala Leu Ala Ala Asp Arg Ala Gly Thr Pro
                20                  25                  30

Ala Phe Val Pro Ala Val Val Ile Gly Thr Gly Tyr Gly Ala Ala Val
                35                  40                  45

Thr Ala Leu Arg Leu Gly Glu Ala Gly Val Arg Thr Val Met Leu Glu
        50                  55                  60

Met Gly Gln Leu Trp Asn Gln Gly Pro Asp Gly Asn Val Phe Ser
65                  70                  75              80

Gly Met Leu Lys Pro Asp Lys Arg Ser Ser Trp Phe Lys Thr Arg Thr
                85                  90                  95

Glu Ala Pro Leu Gly Ser Phe Leu Trp Leu Asp Leu Ala Asn Arg Asp
            100                 105                 110

Ile Asp Pro Tyr Ala Gly Val Leu Asp Arg Val Asn Tyr Asp Gln Met
        115                 120                 125

Ser Val Tyr Val Gly Arg Gly Val Gly Gly Ser Leu Val Asn Gly
130                 135                 140

Gly Met Ala Val Ala Pro Lys Arg Ser Tyr Phe Glu Glu Val Leu Pro
145                 150                 155                 160

Arg Val Asp Ser Ala Ala Met Tyr Asp Arg Tyr Phe Pro Arg Ala Asn
                165                 170                 175

Ser Met Leu Arg Val Asn His Ile Asp Asn Gly Trp Phe Glu Gly Thr
            180                 185                 190

Asp Trp Tyr Lys Phe Ala Arg Val Ser Arg Asp Gln Ala Gln Lys Ala
        195                 200                 205

Gly Leu Gly Thr Val His Val Pro Asn Val Tyr Asp Phe Asp Tyr Met
    210                 215                 220

Arg Arg Glu Ala Asn Gly Glu Val Pro Lys Ser Ala Leu Ala Glu
225                 230                 235                 240

Val Ile Tyr Gly Asn Asn His Gly Lys Gln Ser Leu Asp Lys Thr Tyr
                245                 250                 255

Leu Ala Ala Ala Leu Gly Thr Gly Lys Val Thr Ile Glu Thr Leu His
            260                 265                 270

Gln Ala Arg Thr Ile Arg Gln Gln Lys Asp Gly Thr Tyr Leu Leu Thr
        275                 280                 285
```

```
Val Glu Gln Lys Asp Ala Asp Gly Arg Leu Leu Ala Thr Arg Glu Ile
    290                 295                 300

Ser Cys Arg His Leu Phe Leu Gly Ala Gly Ser Leu Gly Ser Thr Glu
305                 310                 315                 320

Leu Leu Leu Arg Ala Arg Glu Thr Gly Thr Leu Pro Asp Leu Ser Ser
                325                 330                 335

Glu Ile Gly Ala Gly Trp Gly Pro Asn Gly Asn Ile Met Thr Ala Arg
                340                 345                 350

Ala Asn His Val Trp Asn Pro Thr Gly Ala Ser Gln Ser Ser Ile Pro
            355                 360                 365

Ala Leu Gly Ile Asp Asp Trp Asp Asn Pro Ala Ala Pro Val Phe Ala
    370                 375                 380

Glu Ile Ala Pro Met Pro Ala Gly Val Glu Thr Trp Val Ser Leu Tyr
385                 390                 395                 400

Leu Ala Ile Thr Lys Asn Pro Glu Arg Gly Ala Phe Val Tyr Asp Ala
                405                 410                 415

Ala Asn Asp Arg Ala Asn Leu Arg Trp Thr Arg Asp Gln Asn Thr Pro
                420                 425                 430

Ala Val Asn Ala Ala Lys Ser Leu Phe Asp Arg Val Asn Arg Ala Asn
            435                 440                 445

Thr Thr Met Tyr Arg Tyr Asp Leu Phe Gly Lys Gln Leu Lys Ala Phe
    450                 455                 460

Ser Asp Asp Phe Cys Tyr His Pro Leu Gly Gly Cys Val Leu Gly Lys
465                 470                 475                 480

Ala Thr Asp Asp Tyr Gly Arg Val Ser Gly Tyr Lys Asn Leu Tyr Val
                485                 490                 495

Thr Asp Gly Ala Leu Ile Pro Gly Ser Ile Gly Val Asn Pro Phe Val
            500                 505                 510

Thr Ile Thr Ala Leu Ala Glu Arg Asn Ile Glu Arg Val Ile Gln Gln
    515                 520                 525

Asp Ile Lys Ala Ser
    530

<210> SEQ ID NO 40
<211> LENGTH: 552
<212> TYPE: PRT
<213> ORGANISM: Streptomyces chattanoogensis

<400> SEQUENCE: 40

Met Phe Glu Asn Gln Gln Asn Gln His Leu Ser Arg Arg Arg Leu Leu
1               5                   10                  15

Gly Leu Ala Ala Leu Ser Gly Ala Ala Val Ala Gly Met Thr Thr Ile
            20                  25                  30

Ser Ala Ala Pro Arg Ala Ala Ala Asp Lys Arg Ser Pro Lys Ala
        35                  40                  45

Gly Ser Gly Ser Phe Val Pro Ala Val Val Ile Gly Thr Gly Tyr Gly
    50                  55                  60

Ala Ala Val Ser Ala Leu Arg Leu Gly Glu Ala Gly Ile Pro Thr Leu
65                  70                  75                  80

Met Leu Glu Met Gly Gln Leu Trp Asn Lys Pro Ala Asp Asp Gly Asn
                85                  90                  95

Val Phe Cys Gly Met Leu Lys Pro Asp Arg Arg Ser Ser Trp Phe Lys
                100                 105                 110

Ser Arg Thr Glu Ala Pro Leu Gly Ser Phe Leu Trp Leu Asp Val Ile
```

-continued

```
             115                 120                 125
Asn Arg Asp Ile Asp Pro Tyr Ala Gly Val Leu Asp Lys Val His Phe
         130                 135                 140

Asp Gln Met Ser Val Tyr Val Gly Arg Gly Val Gly Gly Gly Ser Leu
145                 150                 155                 160

Val Asn Gly Gly Met Ala Val Pro Lys Arg Ser Tyr Phe Glu Glu
                165                 170                 175

Val Leu Pro Arg Val Asp Ala Ala Glu Met Tyr Asp Arg Tyr Phe Pro
             180                 185                 190

Arg Ala Asn Ser Met Leu Lys Val Asn His Ile Asp Lys Gly Trp Phe
         195                 200                 205

Glu Glu Thr Glu Trp Tyr Lys Phe Ala Arg Val Ser Arg Glu Gln Ala
     210                 215                 220

Gly Lys Ala Gly Leu Ser Thr Thr Phe Val Pro Asn Val Tyr Asp Phe
225                 230                 235                 240

Asp Tyr Met Arg Arg Glu Ala Asn Gly Glu Ser Pro Lys Ser Ala Leu
                245                 250                 255

Ala Thr Glu Val Ile Tyr Gly Asn Asn His Gly Lys Gln Ser Leu Asp
             260                 265                 270

Lys Thr Tyr Leu Ala Ala Ala Leu Gly Thr Gly Lys Val Thr Ile Glu
         275                 280                 285

Thr Leu His Gln Val Lys Ala Ile His Gln Pro Asp Gly Ser Tyr
     290                 295                 300

Val Leu Ser Val Asp Gln Ile Asp Thr Ala Gly Gln Thr Val Ala His
305                 310                 315                 320

Lys Glu Ile Ala Cys Arg His Leu Phe Leu Gly Ala Gly Ser Leu Gly
                325                 330                 335

Ser Thr Glu Leu Leu Val Arg Ala Arg Asp Thr Gly Ala Leu Pro Asp
             340                 345                 350

Leu Asn Ala Glu Val Gly Ala Gly Trp Gly Pro Asn Gly Asn Ile Met
         355                 360                 365

Thr Gly Arg Ala Asn His Val Trp Asn Thr Thr Gly Ala His Gln Ser
     370                 375                 380

Ser Ile Pro Ala Leu Gly Ile Asp Asp Trp Asp Asn Pro Ala Ala Pro
385                 390                 395                 400

Val Phe Ala Glu Ile Ala Pro Met Pro Ala Gly Leu Glu Thr Trp Val
                405                 410                 415

Ser Leu Tyr Leu Ala Ile Thr Lys Asn Pro Glu Arg Gly Thr Phe Val
             420                 425                 430

Tyr Asp Lys Ala Thr Asp Arg Ala Ala Leu Arg Trp Thr Arg Asp Gln
         435                 440                 445

Asn Thr Pro Ala Val Asn Ala Ala Lys Ser Leu Phe Asp Arg Ile Asn
     450                 455                 460

Lys Ala Asn Thr Thr Met Tyr Arg Tyr Asp Leu Phe Gly Pro Gln Leu
465                 470                 475                 480

Lys Asn Phe Ser Asp Asp Phe Cys Tyr His Pro Leu Gly Gly Cys Val
                485                 490                 495

Leu Gly Lys Ala Thr Asp Gly Tyr Gly Arg Val Ala Gly Tyr Arg Asn
             500                 505                 510

Leu Tyr Val Thr Asp Gly Ala Leu Ile Pro Gly Ser Ile Gly Val Asn
         515                 520                 525

Pro Phe Val Thr Ile Thr Ala Leu Ala Glu Arg Asn Ile Glu Arg Ile
     530                 535                 540
```

```
Ile Ala Glu Asp Val Lys Ala Ala
545                 550
```

<210> SEQ ID NO 41
<211> LENGTH: 549
<212> TYPE: PRT
<213> ORGANISM: Streptomyces natalensis

<400> SEQUENCE: 41

```
Met Phe Glu Asn Gln His Leu Ser Arg Arg Leu Leu Gly Leu Ala
1               5                   10                  15

Ala Leu Gly Gly Ala Ala Ala Gly Met Thr Thr Ile Thr Ser Ala
            20                  25                  30

Pro His Ala Ala Ala Asp Arg Arg Ser Pro Gln Ala Arg Ser Gly
                35                  40                  45

Ser Phe Val Pro Ala Val Val Ile Gly Thr Gly Tyr Gly Ala Ala Val
        50                  55                  60

Ser Ala Leu Arg Leu Gly Glu Ala Gly Ile Pro Thr Leu Met Leu Glu
65                  70                  75                  80

Met Gly Gln Leu Trp Asn Lys Pro Ala Asp Asp Gly Asn Val Phe Cys
                85                  90                  95

Gly Met Leu Ser Pro Asp Arg Arg Ser Ser Trp Phe Lys Ser Arg Thr
            100                 105                 110

Glu Ala Pro Leu Gly Ser Phe Leu Trp Leu Asp Val Ile Asn Arg Asp
                115                 120                 125

Ile Asp Pro Tyr Ala Gly Val Leu Asp Lys Val His Phe Asp Gln Met
130                 135                 140

Ser Val Tyr Val Gly Arg Gly Val Gly Gly Ser Leu Val Asn Gly
145                 150                 155                 160

Gly Met Ala Val Val Pro Lys Arg Ser Tyr Phe Glu Glu Val Leu Pro
                165                 170                 175

Arg Val Asp Ala Ala Glu Met Tyr Asp Arg Tyr Phe Pro Arg Ala Asn
                180                 185                 190

Ser Met Leu Lys Val Asn His Ile Asp Lys Gly Trp Phe Glu Glu Thr
            195                 200                 205

Glu Trp Tyr Lys Phe Ala Arg Val Ser Arg Glu Gln Ala Gly Lys Ala
210                 215                 220

Gly Leu Gly Thr Thr Phe Val Pro Asn Val Tyr Asp Phe Asp Tyr Met
225                 230                 235                 240

Arg Arg Glu Ala Asn Gly Glu Ser Pro Lys Ser Ala Leu Ala Thr Glu
                245                 250                 255

Val Ile Tyr Gly Asn Asn His Gly Lys Gln Ser Leu Asp Lys Thr Tyr
            260                 265                 270

Leu Ala Ala Leu Gly Thr Gly Lys Val Thr Ile Glu Thr Leu His
            275                 280                 285

Gln Val Arg Ala Ile His Gln Gln Pro Asp Gly Ser Tyr Val Leu Ser
290                 295                 300

Val Asp Gln Ile Asp Thr Ala Gly Gln Thr Val Ala His Lys Glu Ile
305                 310                 315                 320

Ser Cys Arg His Leu Phe Leu Gly Ala Gly Ser Leu Gly Ser Thr Glu
                325                 330                 335

Leu Leu Val Arg Ala Arg Asp Thr Gly Ala Leu Pro Asp Leu Asn Ala
                340                 345                 350

Glu Val Gly Ala Gly Trp Gly Pro Asn Gly Asn Ile Met Thr Gly Arg
```

-continued

```
                  355                 360                 365
Ala Asn His Val Trp Asn Pro Thr Gly Ala His Gln Ser Ser Ile Pro
        370                 375                 380

Ala Leu Gly Ile Asp Asp Trp Asn Asn Pro Thr Ala Pro Val Phe Ala
385                 390                 395                 400

Glu Ile Ala Pro Met Pro Ala Gly Leu Glu Thr Trp Val Ser Leu Tyr
                405                 410                 415

Leu Ala Ile Thr Lys Asn Pro Glu Arg Gly Thr Phe Val Tyr Asp Lys
            420                 425                 430

Ala Thr Asp Arg Ala Ala Leu Arg Trp Thr Arg Asp Gln Asn Thr Pro
        435                 440                 445

Ala Val Asn Ala Ala Arg Ser Leu Phe Asp Arg Ile Asn Lys Ala Asn
        450                 455                 460

Gly Thr Met Tyr Arg Tyr Asp Leu Phe Gly Pro Gln Leu Lys Asn Phe
465                 470                 475                 480

Ser Asp Asp Phe Cys Tyr His Pro Leu Gly Gly Cys Val Leu Gly Lys
                485                 490                 495

Ala Thr Asp Gly Tyr Gly Arg Val Ala Gly Tyr His Asn Leu Tyr Val
            500                 505                 510

Thr Asp Gly Ala Leu Ile Pro Gly Ser Ile Gly Val Asn Pro Phe Val
        515                 520                 525

Thr Ile Thr Ala Leu Ala Glu Arg Asn Ile Glu Arg Ile Ile Ala Glu
        530                 535                 540

Asp Val Lys Ala Ala
545

<210> SEQ ID NO 42
<211> LENGTH: 547
<212> TYPE: PRT
<213> ORGANISM: Streptomyces avermitilis

<400> SEQUENCE: 42

Met Ile Ala His Gln Pro Leu Ser Arg Arg Met Leu Gly Val Ala
1               5                   10                  15

Ala Leu Gly Ala Ala Leu Ala Gly Gln Thr Thr Ile Thr Ala Ala
                20                  25                  30

Pro Arg Ala Ala Ala Thr Ala Thr Ser Gly Ser Gly Gly Thr Phe
        35                  40                  45

Val Pro Ala Val Val Gly Thr Gly Tyr Gly Ala Ala Val Ser Ala
50                  55                  60

Leu Arg Leu Gly Glu Ala Gly Val Pro Thr Leu Met Leu Glu Met Gly
65                  70                  75                  80

Arg Leu Trp Asn Gln Pro Gly Pro Asp Gly Asn Val Phe Ser Gly Met
                85                  90                  95

Leu Lys Pro Asp Lys Arg Ser Ser Trp Phe Lys Thr Arg Thr Glu Ala
            100                 105                 110

Pro Leu Gly Ser Phe Leu Trp Leu Asp Leu Ala Asn Arg Asp Ile Glu
        115                 120                 125

Pro Tyr Ala Gly Val Leu Asp Arg Val Asn Phe Asp Gln Met Ser Val
    130                 135                 140

Tyr Leu Gly Arg Gly Val Gly Gly Ser Leu Val Asn Gly Gly Met
145                 150                 155                 160

Ala Val Thr Pro Arg Arg Ser Tyr Phe Glu Glu Val Leu Pro Gln Val
                165                 170                 175
```

Asp Ala Glu Glu Met Tyr Thr Lys Tyr Phe Pro Arg Ala Asn Ser Thr
            180                 185                 190

Leu Arg Val Asn Asn Ile Asp Lys Ser Trp Phe Glu Gln Thr Asp Trp
        195                 200                 205

Tyr Ser Phe Ala Arg Val Ser Arg Arg Gln Ala Ser Asn Ala Gly Leu
    210                 215                 220

Ser Thr Thr Phe Val Pro Asn Val Tyr Asp Trp Asp Tyr Met Arg Arg
225                 230                 235                 240

Glu Ala Asp Gly Ala Val Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Ala Ala Leu Gly Thr Gly Lys Val Thr Ile Glu Thr Leu His Gln Val
        275                 280                 285

Lys Thr Ile Arg Gln Gln Asn Asp Gly Thr Tyr Leu Leu Thr Val Glu
    290                 295                 300

Gln Arg Asp Thr Gly Gly Lys Leu Leu Gly Thr Lys Glu Val Ser Cys
305                 310                 315                 320

Arg His Leu Phe Leu Gly Ala Gly Ser Leu Gly Ser Thr Glu Leu Leu
                325                 330                 335

Leu Arg Ala Arg Glu Thr Gly Thr Leu Pro Gly Leu Ser Pro Glu Val
            340                 345                 350

Gly Gly Gly Trp Gly Pro Asn Gly Asn Ile Met Thr Ala Arg Ala Asn
        355                 360                 365

His Met Trp Asn Pro Thr Gly Thr Lys Gln Ser Ser Ile Pro Ala Leu
    370                 375                 380

Gly Ile Asp Asp Trp Asp Asn Pro Asp Thr Pro Val Phe Ala Glu Ile
385                 390                 395                 400

Ala Pro Leu Pro Ala Gly Val Glu Thr Trp Val Ser Leu Tyr Leu Ala
                405                 410                 415

Ile Thr Lys Asn Pro Glu Arg Gly Thr Phe Val Tyr Asp Ala Ala Lys
            420                 425                 430

Asp Arg Ala Asp Leu Arg Trp Thr Arg Asp Gln Asn Ala Pro Ala Ile
        435                 440                 445

Ala Ala Ala Lys Ser Leu Phe Asp Arg Ile Asn Lys Ala Asn Ala Thr
    450                 455                 460

Ile Tyr Arg Tyr Asp Leu Phe Gly Lys Gln Ile Lys Ala Phe Ala Asp
465                 470                 475                 480

Asp Phe Cys Tyr His Pro Leu Gly Gly Cys Val Leu Gly Lys Ala Thr
                485                 490                 495

Asp Asp Tyr Gly Arg Val Thr Gly Tyr Lys Asn Leu Tyr Val Thr Asp
            500                 505                 510

Gly Ser Leu Ile Pro Gly Ser Ile Gly Val Asn Pro Phe Val Thr Ile
        515                 520                 525

Ala Ala Leu Ala Glu Arg Asn Ile Glu Arg Val Ile Lys Gln Asp Ile
    530                 535                 540

Ala Asp Ser
545

<210> SEQ ID NO 43
<211> LENGTH: 552
<212> TYPE: PRT
<213> ORGANISM: Streptomyces griseus

<400> SEQUENCE: 43

```
Met Phe Glu Asn Gln Asn Gln His Leu Ser Arg Arg Leu Leu
1               5                   10                  15

Gly Leu Ala Ala Leu Ser Gly Ala Ala Val Ala Gly Leu Thr Thr Ile
            20                  25                  30

Ser Ala Ala Pro Gln Ala Ala Ala Gly Arg Arg Ala Pro Arg Ala
        35                  40                  45

Gly Asp Gly Ser Phe Val Glu Ala Val Val Ile Gly Thr Gly Tyr Gly
    50                  55                  60

Ala Ala Val Ser Ala Leu Arg Leu Gly Glu Ala Gly Val Pro Thr Leu
65                  70                  75                  80

Met Leu Glu Met Gly Arg Leu Trp Asn Lys Pro Ala Glu Asp Gly Asn
                85                  90                  95

Ile Phe Cys Gly Met Leu Lys Pro Asp Arg Arg Ser Thr Trp Phe Lys
            100                 105                 110

Ser Arg Thr Glu Ala Pro Leu Gly Ser Phe Leu Trp Leu Asp Val Val
        115                 120                 125

Asn Arg Asp Ile Asp Pro Tyr Ala Gly Val Leu Asp Arg Val His Phe
    130                 135                 140

Asp Glu Met Ser Val Tyr Val Gly Arg Gly Val Gly Gly Ser Leu
145                 150                 155                 160

Val Asn Gly Gly Met Ala Val Val Pro Lys Arg Ala Tyr Phe Glu Glu
            165                 170                 175

Val Leu Pro Lys Val Asp Ala Ala Glu Met Tyr Asp Arg Tyr Phe Pro
        180                 185                 190

Arg Ala Asn Ser Met Leu Lys Val Asn His Ile Asp Lys Thr Trp Phe
    195                 200                 205

Glu Asp Thr Glu Trp Tyr Lys Phe Ala Arg Val Ser Arg Glu Gln Ala
210                 215                 220

Ser Lys Ala Gly Leu Gly Thr Thr Phe Val Pro Asn Val Tyr Asp Phe
225                 230                 235                 240

Gly His Met Arg Arg Glu Ala Thr Gly Glu Ala Pro Lys Ser Ala Leu
            245                 250                 255

Ala Gly Glu Val Ile Tyr Gly Asn Asn His Gly Lys Gln Ser Leu Asp
        260                 265                 270

Lys Thr Tyr Leu Ala Ala Ala Leu Gly Thr Gly Lys Val Thr Ile Glu
    275                 280                 285

Thr Leu His Gln Val Lys Ala Ile Arg Gln Gln Lys Asp Gly Gly Tyr
    290                 295                 300

Val Leu Ser Val Asp Gln Thr Asp Ala Asp Gly Lys Thr Val Gly His
305                 310                 315                 320

Lys Glu Ile Gly Cys Arg His Leu Phe Leu Gly Ala Gly Ser Leu Gly
            325                 330                 335

Ser Thr Glu Leu Leu Val Arg Ala Arg Asp Thr Gly Ala Leu Pro Asp
        340                 345                 350

Leu Asn Ala Glu Val Gly Gly Trp Gly Pro Asn Gly Asn Ile Met
    355                 360                 365

Thr Gly Arg Ala Asn His Val Trp Asn Pro Thr Gly Ala His Gln Ser
    370                 375                 380

Ser Ile Pro Ala Leu Gly Ile Asp Asp Trp Asn Asn Ala Ala Pro
385                 390                 395                 400

Val Phe Ala Glu Ile Ala Pro Met Pro Ala Gly Ala Glu Thr Trp Val
            405                 410                 415
```

```
Ser Leu Tyr Leu Ala Ile Thr Lys Asn Pro Glu Arg Gly Thr Phe Val
            420                 425                 430

Tyr Asp Lys Ala Thr Asp Arg Val Ala Leu Arg Trp Thr Arg Asp Gln
        435                 440                 445

Asn Thr Pro Ala Val Asn Ala Ala Lys Ser Leu Phe Asp Arg Ile Asn
    450                 455                 460

Gln Ala Asn Thr Thr Val Tyr Arg Tyr Asp Leu Phe Gly Lys Gln Val
465                 470                 475                 480

Lys Ala Phe Ser Asp Asp Phe Ser Tyr His Pro Leu Gly Gly Cys Val
                485                 490                 495

Leu Gly Lys Ala Thr Asp Leu Tyr Gly Arg Val Ala Gly His Arg Asn
            500                 505                 510

Leu Tyr Val Met Asp Gly Ser Leu Ile Pro Gly Ser Ile Gly Val Asn
        515                 520                 525

Pro Phe Val Thr Ile Thr Ala Leu Ala Glu Arg Asn Ile Glu Arg Ile
    530                 535                 540

Ile Ala Glu Asp Val Lys Ala Ala
545                 550

<210> SEQ ID NO 44
<211> LENGTH: 553
<212> TYPE: PRT
<213> ORGANISM: Streptomyces hygrospinosus

<400> SEQUENCE: 44

Met Phe Glu Asn Gln Gln Asn Gln His Leu Ser Arg Arg Arg Leu Leu
1               5                   10                  15

Gly Leu Ala Ala Leu Ser Gly Ala Ala Val Thr Gly Leu Thr Thr Ile
            20                  25                  30

Ser Ala Ala Pro Arg Ala Ala Ala Asp Lys Arg Ser Pro Arg Ala
        35                  40                  45

Asp Ser Gly Ser Phe Val Pro Ala Val Val Ile Gly Thr Gly Tyr Gly
    50                  55                  60

Ala Ala Val Ser Ala Leu Arg Leu Gly Glu Ala Gly Val Glu Thr Leu
65                  70                  75                  80

Met Leu Glu Met Gly Gln Leu Trp Asn Lys Pro Ala Glu Asp Gly Asn
                85                  90                  95

Val Phe Cys Gly Met Leu Thr Pro Asp Arg Arg Ser Ser Trp Phe Lys
            100                 105                 110

Ser Arg Thr Glu Ala Pro Leu Gly Ser Phe Leu Trp Leu Asp Val Ile
        115                 120                 125

Asn Arg Asp Ile Glu Pro Tyr Ala Gly Val Leu Asp Arg Val His Phe
    130                 135                 140

Asp Gln Met Ser Val Tyr Val Gly Arg Gly Val Gly Gly Gly Ser Leu
145                 150                 155                 160

Val Asn Gly Gly Met Ala Val Val Pro Lys Arg Ala Tyr Phe Glu Glu
                165                 170                 175

Val Leu Pro Gln Val Asp Ala Ala Gln Met Tyr Glu Arg Tyr Phe Pro
            180                 185                 190

Arg Ala Asn Ala Ala Leu Lys Val Asn His Ile Asp Pro Ala Trp Phe
        195                 200                 205

Glu Lys Thr Glu Trp Tyr Asn Phe Ala Arg Val Ser Arg Glu Gln Ala
    210                 215                 220

Gly Lys Ala Gly Leu Ser Thr Thr Phe Val Pro Asn Val Tyr Asp Phe
225                 230                 235                 240
```

```
Asp His Met Gln Arg Glu Ala Gly Thr Ala Pro Lys Ser Ala Leu
            245                 250                 255

Ala Gly Glu Val Ile Tyr Gly Asn Asn His Gly Lys Gln Ser Leu Asp
        260                 265                 270

Lys Thr Tyr Leu Ala Ala Leu Gly Thr Gly Lys Val Thr Ile Glu
            275                 280                 285

Thr Leu His Arg Val Thr Ala Ile Arg Gln Gln Ala Asp Gly Ser Tyr
        290                 295                 300

Val Leu Ser Val Asp Gln Ser Asp Ala Asn Gly Thr Val Ile Ala His
305                 310                 315                 320

Lys Glu Ile Ala Cys Arg His Leu Phe Leu Gly Ala Gly Ser Leu Gly
            325                 330                 335

Ser Thr Glu Leu Leu Val Arg Ala Arg Asp Thr Gly Ala Leu Pro His
            340                 345                 350

Leu Asn Ala Glu Val Gly Glu Gly Trp Gly Pro Asn Gly Asn Ile Met
            355                 360                 365

Thr Gly Arg Ala Asn His Val Trp Asn Pro Thr Gly Ala His Gln Ser
        370                 375                 380

Ser Ile Pro Ala Leu Gly Ile Asp Asp Trp Asp Asn Pro Asp Ala Pro
385                 390                 395                 400

Val Phe Ala Glu Ile Ala Pro Met Pro Ala Gly Leu Glu Thr Trp Val
            405                 410                 415

Ser Leu Tyr Leu Ala Ile Thr Lys Asn Pro Gln Arg Gly Ser Phe Val
            420                 425                 430

Tyr Asp Lys Ala Thr Asp Arg Ala Met Leu Arg Trp Thr Arg Glu Gln
            435                 440                 445

Asn Ala Pro Ala Val Ala Ala Lys Ser Leu Phe Asp Arg Ile Asn
        450                 455                 460

Lys Ala Asn Thr Thr Met Tyr Arg Tyr Asp Leu Phe Gly Pro Gln Leu
465                 470                 475                 480

Lys Asn Phe Ala Asp Asp Phe Cys Tyr His Pro Leu Gly Gly Cys Val
            485                 490                 495

Leu Gly Lys Ala Thr Asp Asp Tyr Gly Arg Val Ala Gly Tyr His Asn
            500                 505                 510

Leu Tyr Val Thr Asp Gly Ala Leu Ile Pro Gly Ser Ile Gly Val Asn
        515                 520                 525

Pro Phe Val Thr Ile Thr Ala Leu Ala Glu Arg Asn Ile Glu Arg Val
        530                 535                 540

Ile Ala Glu Asp Val Arg Thr Ala Ala
545                 550

<210> SEQ ID NO 45
<211> LENGTH: 549
<212> TYPE: PRT
<213> ORGANISM: Streptomyces rimosus

<400> SEQUENCE: 45

Met Ile Glu Asn Gln His Leu Ser Arg Arg Leu Leu Gly Leu Ala
1               5                   10                  15

Ala Leu Gly Gly Ala Ala Val Ala Gly Met Thr Thr Ile Ser Ala Ala
            20                  25                  30

Pro Arg Ala Ala Ala Ala Gly Gln Gly Ser Pro Arg Ala Gly Asp Gly
        35                  40                  45

Ala Phe Val Pro Ala Val Val Ile Gly Thr Gly Tyr Gly Ala Ala Val
```

-continued

```
            50                  55                  60
Ser Ala Leu Arg Leu Gly Glu Ala Gly Ile Pro Thr Leu Met Leu Glu
 65                      70                  75                  80

Met Gly Gln Leu Trp Asn Lys Pro Ala Asp Asp Gly Asn Ile Phe Cys
                     85                  90                  95

Gly Met Leu Lys Pro Asp Arg Arg Ser Ser Trp Phe Lys Ser Arg Thr
                    100                 105                 110

Glu Ala Pro Leu Gly Ser Phe Leu Trp Leu Asp Val Ile Asn Arg Asn
                115                 120                 125

Ile Asp Pro Tyr Ala Gly Val Leu Asp Lys Val His Phe Asp Glu Met
            130                 135                 140

Ser Val Tyr Val Gly Arg Gly Val Gly Gly Ser Leu Val Asn Gly
145                 150                 155                 160

Gly Met Ala Val Val Pro Lys Arg Ser Tyr Phe Glu Glu Val Leu Pro
                    165                 170                 175

Arg Val Asp Ala Ala Gln Met Tyr Asp Arg Tyr Phe Pro Arg Ala Asn
                180                 185                 190

Ser Met Leu Lys Val Asn His Ile Asp Lys Gly Trp Phe Glu Asp Thr
                195                 200                 205

Glu Trp Tyr Lys Tyr Ala Arg Val Ser Arg Glu Gln Ala Gly Lys Ala
210                 215                 220

Gly Leu Ser Thr Thr Phe Val Pro Asn Val Tyr Asp Phe Gly His Met
225                 230                 235                 240

Arg Arg Glu Ala Asp Gly Thr Ala Pro Lys Ser Ala Leu Ala Gly Glu
                    245                 250                 255

Val Ile Tyr Gly Asn Asn His Gly Lys Gln Ser Leu Asp Lys Thr Tyr
                260                 265                 270

Leu Ala Ala Ala Leu Gly Thr Gly Lys Val Thr Ile Glu Thr Leu His
                275                 280                 285

Gln Val Lys Ala Ile Arg Arg Gln Pro Asp Gly Ser Tyr Val Leu Ser
                290                 295                 300

Val Val Gln Ser Asp Ala Asp Gly Lys Val Val Ala Gln Lys Glu Ile
305                 310                 315                 320

Gly Cys Arg His Leu Phe Leu Gly Ala Gly Ser Leu Gly Ser Thr Glu
                    325                 330                 335

Leu Leu Val Arg Ala Arg Asp Thr Gly Thr Leu Pro Glu Leu Asn Ala
                340                 345                 350

Glu Val Gly Ala Gly Trp Gly Pro Asn Gly Asn Ile Met Thr Gly Arg
                355                 360                 365

Ala Asn His Val Trp Asn Pro Thr Gly Ala His Gln Ser Ser Ile Pro
370                 375                 380

Ala Leu Gly Ile Asp Asp Trp Asp Asn Pro Ala Pro Val Phe Ala
385                 390                 395                 400

Glu Ile Ala Pro Met Pro Ala Gly Leu Glu Thr Trp Val Ser Leu Tyr
                    405                 410                 415

Leu Ala Ile Thr Lys Asn Pro Glu Arg Gly Thr Phe Val Tyr Asp Lys
                420                 425                 430

Ala Thr Asp Arg Ala Lys Leu Arg Trp Thr Arg Asp Gln Asn Thr Pro
                435                 440                 445

Ala Val Asn Ala Ala Lys Ser Leu Phe Asp Arg Ile Asn Lys Ala Asn
                450                 455                 460

Thr Thr Met Tyr Arg Tyr Asp Leu Phe Gly Ser Gln Leu Lys Asn Phe
465                 470                 475                 480
```

Ser Asp Asp Phe Ser Tyr His Pro Leu Gly Gly Cys Val Leu Gly Lys
            485                 490                 495

Ala Thr Asp Leu Tyr Gly Arg Val Ala Gly Tyr Arg Asn Leu Tyr Val
            500                 505                 510

Met Asp Gly Ala Leu Val Pro Gly Ser Ile Gly Val Asn Pro Phe Val
            515                 520                 525

Thr Ile Thr Ala Leu Ala Glu Arg Asn Ile Glu Arg Ile Ile Ala Glu
            530                 535                 540

Asp Val Lys Ala Ala
545

<210> SEQ ID NO 46
<211> LENGTH: 547
<212> TYPE: PRT
<213> ORGANISM: Streptomyces durhamensis

<400> SEQUENCE: 46

Met Phe Ala His Gln Pro Leu Ser Arg Arg Met Leu Gly Met Ala
1               5                   10                  15

Ala Leu Gly Ala Ala Ala Leu Ala Gly Gln Thr Thr Ile Ala Ala Ala
            20                  25                  30

Pro Arg Ala Ala Ala Thr Ala Thr Ser Gly Ser Gly Gly Thr Phe
            35                  40                  45

Val Pro Ala Val Val Gly Thr Gly Tyr Gly Ala Ala Val Ser Ala
            50                  55                  60

Leu Arg Leu Gly Glu Ala Gly Val Thr Thr Leu Met Leu Glu Met Gly
65                  70                  75                  80

Gln Leu Trp Asn Gln Ala Gly Pro Asp Gly Asn Val Phe Cys Gly Met
                85                  90                  95

Leu Lys Pro Asp Lys Arg Ser Ser Trp Phe Lys Asn Arg Thr Glu Ala
            100                 105                 110

Pro Leu Gly Ser Phe Leu Trp Leu Asp Leu Ala Asn Arg Asp Ile Asp
            115                 120                 125

Pro Tyr Ala Gly Val Leu Asp Arg Val Asn Phe Asp Gln Met Ser Val
            130                 135                 140

Tyr Val Gly Arg Gly Val Gly Gly Ser Leu Val Asn Gly Gly Met
145                 150                 155                 160

Ala Val Thr Pro Arg Arg Ser Tyr Phe Glu Glu Val Leu Pro Gln Val
                165                 170                 175

Asp Ala Glu Glu Met Tyr Thr Lys Tyr Phe Pro Arg Ala Asn Ser Thr
            180                 185                 190

Leu Arg Val Asn Thr Val Asp Lys Ser Trp Phe Glu Gln Thr Asp Trp
            195                 200                 205

Tyr Thr Phe Ala Arg Val Ser Arg Gln Gln Ala Ala Asn Ala Gly Leu
            210                 215                 220

Gly Thr Thr Phe Val Pro Asn Val Tyr Asp Trp Asp Tyr Met Arg Arg
225                 230                 235                 240

Glu Ala Asp Gly Thr Val Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Ala Ala Leu Gly Thr Gly Lys Val Thr Ile Glu Thr Leu His Gln Val
            275                 280                 285

Arg Thr Ile Arg Gln Gln Asn Asp Gly Thr Tyr Leu Leu Thr Val Glu

```
            290                 295                 300
Gln Arg Asp Ala Asp Gly Lys Leu Leu Ala Thr Lys Glu Val Ser Cys
305                 310                 315                 320

Arg His Leu Phe Leu Gly Ala Gly Ser Leu Gly Ser Thr Glu Leu Leu
                325                 330                 335

Leu Arg Ala Arg Glu Thr Gly Thr Leu Pro Asp Leu Ser Ser Glu Ile
                340                 345                 350

Gly Gly Gly Trp Gly Pro Asn Gly Asn Ile Met Thr Ala Arg Ala Asn
                355                 360                 365

His Met Trp Asn Pro Thr Gly Thr Lys Gln Ser Ser Ile Pro Ala Leu
            370                 375                 380

Gly Ile Asp Asp Trp Asp Asn Pro Asn Asn Pro Val Phe Ala Glu Ile
385                 390                 395                 400

Ala Pro Met Pro Ala Gly Val Glu Thr Trp Val Ser Leu Tyr Leu Ala
                405                 410                 415

Ile Thr Lys Asn Pro Glu Arg Gly Thr Phe Val Tyr Asp Ala Ala Lys
            420                 425                 430

Asp Arg Ala Asp Leu Arg Trp Thr Arg Asp Gln Asn Ala Pro Ala Val
            435                 440                 445

Ala Ala Ala Lys Ser Leu Phe Asp Arg Ile Asn Lys Ala Asn Thr Thr
        450                 455                 460

Ile Tyr Arg Tyr Asp Leu Phe Gly Lys Gln Ile Lys Ala Phe Ala Asp
465                 470                 475                 480

Asp Phe Cys Tyr His Pro Leu Gly Gly Cys Val Leu Gly Lys Ala Thr
                485                 490                 495

Asp Asn Tyr Gly Arg Val Ala Gly Tyr Lys Asn Leu Tyr Val Thr Asp
                500                 505                 510

Gly Ser Leu Ile Pro Gly Ser Ile Gly Val Asn Pro Phe Val Thr Ile
            515                 520                 525

Thr Ala Leu Ala Glu Arg Asn Val Glu Arg Ile Ile Lys Glu Asp Val
        530                 535                 540

Ala Asn Ser
545

<210> SEQ ID NO 47
<211> LENGTH: 547
<212> TYPE: PRT
<213> ORGANISM: Streptomyces sclerotialus

<400> SEQUENCE: 47

Met Asn Ala His Gln Pro Leu Ser Arg Arg Met Leu Gly Leu Ala
1               5                   10                  15

Ala Leu Gly Ala Ala Leu Ala Gly Gln Thr Thr Ile Thr Ala Ala
                20                  25                  30

Pro Arg Ala Ala Ala Thr Thr Thr Gly Val Ser Asp Gly Thr Phe
            35                  40                  45

Val Pro Ala Val Val Val Gly Thr Gly Tyr Gly Ala Ala Val Ser Ala
        50                  55                  60

Leu Arg Leu Gly Glu Ala Gly Ile Ser Thr Leu Met Leu Glu Met Gly
65                  70                  75                  80

Gln Leu Trp Asn Gln Pro Gly Pro Asp Gly Asn Ile Phe Cys Gly Thr
                85                  90                  95

Leu Ala Pro Asp Lys Arg Ser Ser Trp Phe Lys Thr Arg Thr Glu Ala
                100                 105                 110
```

```
Pro Leu Gly Ser Phe Leu Trp Leu Asp Leu Ala Asn Arg Asp Ile Glu
        115                 120                 125

Pro Tyr Ala Gly Val Leu Asp Arg Val Asn Phe Asp Gln Met Ser Val
130                 135                 140

Tyr Val Gly Arg Gly Val Gly Gly Ser Leu Val Asn Gly Gly Met
145                 150                 155                 160

Ala Val Thr Pro Arg Arg Ser Tyr Phe Glu Glu Val Leu Pro Gln Val
                    165                 170                 175

Asp Ala Asp Glu Met Tyr Ser Thr Tyr Phe Pro Arg Ala Asn Ser Gly
            180                 185                 190

Leu Arg Val Lys Asn Ile Asp Glu Ala Trp Phe Glu Gln Thr Glu Trp
        195                 200                 205

Tyr Lys Tyr Ala Arg Val Gly Arg Asp Gln Ala Ala Asn Ala Gly Leu
    210                 215                 220

Gly Thr Thr Phe Val Pro Asn Val Tyr Asp Trp Asp Tyr Met Arg Arg
225                 230                 235                 240

Glu Ala Asp Gly Ser Val Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Asp Ala Leu Gly Thr Gly Lys Val Ala Ile Glu Thr Leu His Gln Val
        275                 280                 285

Arg Thr Ile Arg Gln Arg Asn Asp Gly Thr Tyr Leu Leu Thr Val Glu
    290                 295                 300

Gln Lys Asp Ala Gln Gly Gly Leu Ile Ala Thr Lys Glu Ile Ser Cys
305                 310                 315                 320

Arg His Leu Phe Leu Gly Ala Gly Ser Leu Gly Ser Thr Glu Leu Leu
                325                 330                 335

Leu Arg Ala Arg Glu Thr Gly Thr Leu Ala Asn Leu Ser Ser Glu Ile
            340                 345                 350

Gly Gly Gly Trp Gly Pro Asn Gly Asn Ile Met Thr Ala Arg Ala Asn
        355                 360                 365

His Val Trp Asn Thr Thr Gly Ser Asn Gln Ser Ser Ile Pro Ala Leu
    370                 375                 380

Gly Ile Asp Asp Trp Asp Asn Pro Asp Ser Pro Val Phe Ala Glu Ile
385                 390                 395                 400

Ala Pro Met Pro Ala Gly Leu Glu Thr Trp Val Ser Leu Tyr Leu Ala
                405                 410                 415

Ile Thr Lys Asn Pro Glu Arg Gly Thr Phe Val Tyr Asp Ala Ala Lys
            420                 425                 430

Asp Arg Ala Asp Leu Arg Trp Thr Arg Glu Gln Asn Ala Pro Ala Val
        435                 440                 445

Ala Ala Ala Lys Ser Leu Phe Asp Arg Ile Asn Arg Ala Asn Ser Thr
    450                 455                 460

Ile Tyr Arg Tyr Asp Leu Phe Gly Pro Gln Ile Lys Ala Phe Ala Asp
465                 470                 475                 480

Asp Phe Cys Tyr His Pro Leu Gly Gly Cys Val Leu Gly Lys Ala Thr
                485                 490                 495

Asp Asn Tyr Gly Arg Val Thr Gly Tyr Lys Asn Leu Tyr Val Thr Asp
            500                 505                 510

Gly Ser Leu Ile Pro Gly Ser Ile Gly Val Asn Pro Phe Val Thr Ile
        515                 520                 525

Thr Ala Leu Ala Glu Arg Asn Val Glu Arg Ile Ile Lys Glu Asp Val
```

530                 535                 540

Thr Gly Ser
545

<210> SEQ ID NO 48
<211> LENGTH: 547
<212> TYPE: PRT
<213> ORGANISM: Streptomyces mutabilis

<400> SEQUENCE: 48

Met Asn Ala His Gln Pro Leu Ser Arg Arg Met Leu Gly Leu Ala
1               5                   10                  15

Ala Leu Gly Ala Ala Leu Ala Gly Gln Thr Thr Ile Thr Ala Ala
                20                  25                  30

Pro Arg Ala Ala Ala Thr Arg Thr Gly Val Ser Asp Gly Thr Leu
            35                  40                  45

Val Pro Ala Val Val Gly Thr Gly Tyr Gly Ala Ala Val Ser Ala
    50                  55                  60

Leu Arg Leu Gly Glu Ala Gly Ile Ser Thr Leu Met Leu Glu Met Gly
65                  70                  75                  80

Gln Leu Trp Asn Gln Pro Gly Pro Asp Gly Asn Ile Phe Cys Gly Thr
                85                  90                  95

Leu Ala Pro Asp Lys Arg Ser Ser Trp Phe Lys Thr Arg Thr Glu Ala
                100                 105                 110

Pro Leu Gly Ser Phe Leu Trp Leu Asp Leu Ala Asn Arg Asp Ile Glu
            115                 120                 125

Pro Tyr Ala Gly Val Leu Asp Arg Val Asn Phe Asp Gln Met Ser Val
    130                 135                 140

Tyr Val Gly Arg Gly Val Gly Gly Ser Leu Val Asn Gly Gly Met
145                 150                 155                 160

Ala Val Thr Pro Arg Arg Ser Tyr Phe Glu Glu Val Leu Pro Gln Val
                165                 170                 175

Asp Ala Asp Glu Met Tyr Ser Thr Tyr Phe Pro Arg Ala Asn Ser Gly
            180                 185                 190

Leu Arg Val Lys Asn Val Asp Glu Ala Trp Phe Glu Gln Thr Glu Trp
    195                 200                 205

Tyr Gln Tyr Ala Arg Val Gly Arg Glu Gln Ala Arg Asn Ala Gly Leu
    210                 215                 220

Ser Thr Thr Phe Val Pro Asn Val Tyr Asp Trp Asp Tyr Met Arg Arg
225                 230                 235                 240

Glu Ala Asp Gly Ser Val Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Asp Ala Leu Gly Thr Gly Lys Val Ala Ile Glu Thr Leu His Gln Val
    275                 280                 285

Lys Thr Ile Arg Gln Arg Asn Asp Gly Thr Tyr Leu Leu Thr Val Glu
    290                 295                 300

Gln Lys Asp Ala Gln Gly Gly Leu Leu Ala Thr Lys Glu Ile Ser Cys
305                 310                 315                 320

Arg His Leu Phe Leu Gly Ala Gly Ser Leu Gly Ser Thr Glu Leu Leu
                325                 330                 335

Leu Arg Ala Arg Glu Thr Gly Leu Ala Asp Leu Ser Pro Glu Ile
            340                 345                 350

```
Gly Gly Gly Trp Gly Pro Asn Gly Asn Ile Met Thr Ala Arg Ala Asn
            355                 360                 365

His Met Trp Asn Pro Thr Gly Ser Asn Gln Ser Ile Pro Ala Leu
    370                 375                 380

Gly Ile Asp Asp Trp Asp Asn Pro Asp Asn Pro Val Phe Ala Glu Ile
385                 390                 395                 400

Ala Pro Met Pro Ala Gly Leu Glu Thr Trp Val Ser Leu Tyr Leu Ala
                405                 410                 415

Ile Ala Lys Asn Pro Glu Arg Gly Thr Phe Val Tyr Asp Ala Ala Lys
                420                 425                 430

Asp Arg Ala Asp Leu Arg Trp Thr Arg Glu Gln Asn Ala Pro Ala Val
                435                 440                 445

Ala Ala Ala Lys Ser Leu Phe Asp Arg Ile Asn Lys Ala Asn Ser Thr
                450                 455                 460

Ile Tyr Arg Tyr Asp Leu Phe Gly Ser Gln Ile Lys Ala Phe Ala Asp
465                 470                 475                 480

Asp Phe Cys Tyr His Pro Leu Gly Gly Cys Val Leu Gly Lys Ala Thr
                485                 490                 495

Asp Asn Tyr Gly Arg Val Thr Gly Tyr Lys Asn Leu Tyr Val Thr Asp
                500                 505                 510

Gly Ser Leu Ile Pro Gly Ser Ile Gly Val Asn Pro Phe Val Thr Ile
        515                 520                 525

Thr Ala Leu Ala Glu Arg Asn Val Glu Arg Ile Ile Lys Glu Asp Val
        530                 535                 540

Thr Gly Ser
545

<210> SEQ ID NO 49
<211> LENGTH: 540
<212> TYPE: PRT
<213> ORGANISM: Streptomyces scabiei

<400> SEQUENCE: 49

Met Gln Arg Gln Leu Thr Arg Arg His Ile Leu Gly Met Ala Ala Leu
1               5                   10                  15

Gln Thr Ala Ala Gly Leu Gly Leu Thr Arg Ile Gly Leu Gln Ser Ala
                20                  25                  30

Arg Ala Ala Glu Pro Asp Ala Val Asp Asn Ala Pro Ala Leu Val Ile
            35                  40                  45

Gly Ser Gly Tyr Gly Ala Ala Val Ala Ala Leu Arg Leu Gly Gln Ala
    50                  55                  60

Gly Ile Arg Thr Leu Val Leu Glu Met Gly Arg Ala Trp Thr Thr Pro
65                  70                  75                  80

Gly Ala Asp Gly Lys Ile Phe Cys Ser Thr Lys Glu Pro Asp Glu Arg
                85                  90                  95

Ser Met Trp Phe Lys Thr Arg Thr Glu Ala Pro Leu Ala Thr Phe Leu
                100                 105                 110

Trp Leu Asp Val Val Asn Gln Asp Ile Ser Arg Tyr Pro Gly Val Leu
            115                 120                 125

Asp Arg Val Arg His Ala Asn Met Ser Val Phe Leu Gly Arg Gly Val
    130                 135                 140

Gly Gly Gly Ser Leu Val Asn Gly Ser Met Ala Val Thr Pro Leu Arg
145                 150                 155                 160

Ser Tyr Phe Ala Glu Gln Phe Pro Thr Val Asp Thr Ala Glu Met Tyr
                165                 170                 175
```

Ser Thr Tyr Phe Pro Arg Ala Arg Ser Met Leu Gly Val Asn Thr Val
            180                 185                 190

Asp Pro Ala Trp Phe Glu Ser Thr Glu Trp Tyr Arg Phe Ser Arg Val
            195                 200                 205

Ser Arg Ala His Ala Ala Lys Ala Gly Leu Arg Thr Thr Phe Val Pro
210                 215                 220

Ser Val Tyr Asp Phe Asp His Met Gln Arg Glu Ala Ala Gly Thr Ala
225                 230                 235                 240

Thr Lys Ser Ala Leu Ala Gly Glu Val Ile Tyr Gly Asn Asn His Gly
            245                 250                 255

Lys Lys Ser Leu Asp Lys Thr Tyr Leu Ala Ala Leu Gly Thr Gly
            260                 265                 270

Asn Val Thr Ile His Thr Met Glu Arg Ala Arg Gly Ile Arg Arg Leu
            275                 280                 285

Gly Asp Gly Thr Tyr Val Val Thr Ala Asp Arg Ile Asp Gly Thr Gly
            290                 295                 300

Ala Val Val Glu Thr Lys Glu Tyr Gly Cys Thr Tyr Leu Phe Leu Gly
305                 310                 315                 320

Ala Gly Ser Val Gly Thr Thr Glu Leu Leu Val Arg Ala Arg Ala Lys
            325                 330                 335

Gly Thr Leu Pro Ala Leu Asn Ala Ser Val Gly Ala Gly Trp Gly Pro
            340                 345                 350

Asn Gly Asn Val Met Leu Gly Arg Ala Asn His Leu Trp Asp Thr Val
            355                 360                 365

Gly Ala Asn Gln Ser Thr Met Pro Val Met Gly Ile Asp Asp Trp Ala
            370                 375                 380

Asn Thr Ala Asn Pro Val Phe Ala Glu Ile Ala Pro Leu Pro Thr Gly
385                 390                 395                 400

Leu Glu His Trp Val Ser Leu Tyr Leu Ala Ile Thr Lys Asn Thr Glu
            405                 410                 415

Arg Ala Ser Phe Thr Tyr Asp Ala Ala Thr Asp Ser Ala Lys Leu Gly
            420                 425                 430

Trp Ser Ala Ala Gln Ser Ala Val Ser Ser Met Ala Lys Lys Leu
            435                 440                 445

Phe Asp Arg Ile Asn Ser Ala Asn Ser Thr Met Tyr Arg Tyr Asp Leu
450                 455                 460

Phe Gly Ser Ser Asn Lys Val Phe Ala Asp Asp Phe Thr Tyr His Pro
465                 470                 475                 480

Leu Gly Gly Cys Val Leu Gly Arg Ala Thr Asp Tyr Gly Arg Val
            485                 490                 495

Lys Gly Tyr Glu Asn Leu Tyr Val Thr Asp Gly Ser Leu Val Pro Gly
            500                 505                 510

Ser Ile Gly Val Asn Pro Phe Val Thr Ile Thr Ala Leu Ala Glu Arg
            515                 520                 525

Asn Val Ala Arg Val Leu Val Glu Asp Thr Ala Pro
530                 535                 540

<210> SEQ ID NO 50
<211> LENGTH: 533
<212> TYPE: PRT
<213> ORGANISM: Streptomyces mobaraensis

<400> SEQUENCE: 50

Met Gly Ala Ala Ala Phe Gly Gly Gly Ile Leu Ser Gly Ala Ser Gly

-continued

```
  1               5                  10                 15
Ala Glu Ala Ala Glu Ala Asp Val Ala Arg Asp Gly Ala Phe Val
             20                 25                 30
Pro Ala Val Val Val Gly Thr Gly Tyr Gly Ala Ala Val Thr Ala Leu
             35                 40                 45
Arg Leu Ala Glu Ala Gly Glu Arg Val Leu Met Leu Glu Met Gly Arg
         50                 55                 60
Trp Trp Asp Arg Pro Gly Ala Asp Gly Arg Val Phe Cys Gly Met Leu
 65                 70                 75                 80
Asp Pro Asp Arg Arg Ser Ser Trp Phe Arg Thr Arg Thr Ala Ala Pro
                 85                 90                 95
Leu Gly Ser Phe Leu Trp Leu Asp Val Val Asp Arg Asn Ile Glu Pro
             100                105                110
Tyr Ala Gly Val Leu Asp Arg Val Asp Phe Gly Ser Met Ala Val Tyr
             115                120                125
Ala Gly Arg Gly Val Gly Gly Ser Leu Val Asn Gly Gly Met Ala
             130                135                140
Val Ala Pro Arg Arg Asp Tyr Leu Gln Arg Val Leu Pro Arg Val Asp
145                150                155                160
Ala Ala Glu Met Tyr Arg Arg Tyr Phe Pro Arg Ala Arg Ala Met Leu
                 165                170                175
Arg Val Asn Gly Ile Asp Arg Thr Trp Phe Glu Gly Thr Glu Trp Tyr
             180                185                190
Arg Tyr Ser Arg Val Ala Arg Glu Gln Ala Ala Arg Ala Gly Leu Arg
             195                200                205
Ser Val Phe Leu Asp Asn Val Tyr Asp Phe Arg His Met Arg Arg Glu
210                215                220
Ala Asp Gly Thr Ala Pro Arg Ser Ala Leu Ala Gly Glu Leu Ile Tyr
225                230                235                240
Gly Asn Asn His Gly Arg Met Ser Leu Asp Lys Thr Tyr Val Ala Ala
                 245                250                255
Ala Leu Arg Thr Gly Arg Val Thr Ile Ala Pro Leu His Arg Ala Lys
             260                265                270
Ser Leu Arg Arg Arg Ala Gly Gly Tyr Val Leu Thr Val Glu Arg
             275                280                285
Ser Asp Glu Thr Gly Arg Arg Thr Ala Val Lys Glu Ile Gly Cys Arg
290                295                300
Arg Leu Phe Leu Gly Ala Gly Ser Leu Gly Thr Thr Glu Leu Leu Leu
305                310                315                320
Arg Ala Arg Glu Thr Gly Ala Leu Pro Asp Leu Gly Pro Glu Ile Gly
                 325                330                335
Arg Gly Trp Gly Pro Asn Gly Asn Val Met Ala Ala Arg Ala Asn His
             340                345                350
Gly Thr Asp Pro Thr Gly Cys His Gln Ser Thr Val Pro Ala Leu Gly
             355                360                365
Leu Asp Asp Trp Asp Asp Pro Arg His Pro Val Phe Ala Glu Val Thr
         370                375                380
Pro Val Pro Ala Gly Thr Glu Thr Trp Ile Ser Leu Tyr Ile Ala Ile
385                390                395                400
Thr Arg Asn Pro Glu Arg Gly Thr Phe Val Tyr Asp Arg Ala Thr Asp
                 405                410                415
Arg Met Gly Leu Arg Trp Thr Arg Asp Gln Asn Arg Pro Ala Val Asp
             420                425                430
```

```
Ala Ala Arg Ser Phe Phe Asp Arg Val Asn Arg Ala Asn Arg Thr Asp
            435                 440                 445

Tyr Arg Tyr Asp Leu Phe Gly Pro Arg Ala Lys Ala Phe Ala Asp Asp
450                 455                 460

Phe Thr Tyr His Pro Leu Gly Gly Cys Val Leu Gly Arg Ala Thr Asp
465                 470                 475                 480

Pro Tyr Gly Arg Ile Pro Gly His Pro Gly Leu Tyr Val Thr Asp Gly
                485                 490                 495

Ser Leu Val Pro Gly Ser Leu Gly Val Asn Pro Phe Leu Thr Ile Thr
            500                 505                 510

Ala Leu Ala Glu Arg Asn Ile Glu Arg Ile Val Arg Gln Asp Val Leu
            515                 520                 525

Pro Ala Ser Gly Arg
        530

<210> SEQ ID NO 51
<211> LENGTH: 528
<212> TYPE: PRT
<213> ORGANISM: Streptomyces cellulosae

<400> SEQUENCE: 51

Met Ala Ala Leu Gln Ser Ala Ala Leu Gly Phe Thr Arg Val Gly
1               5                   10                  15

Leu Gln Ser Ala Arg Ala Ala Glu Pro Asp Ala Val Glu Ser Ala Pro
            20                  25                  30

Ala Ile Val Ile Gly Ser Gly Tyr Gly Ala Ala Val Ala Ala Leu Arg
            35                  40                  45

Leu Gly Gln Ala Gly Ile Arg Thr Leu Val Leu Glu Met Gly Arg Leu
50                  55                  60

Trp Asn Thr Pro Gly Ser Asp Gly Lys Val Phe Cys Ser Thr Ala Ala
65                  70                  75                  80

Pro Asp Gln Arg Ser Met Trp Phe Arg Thr Arg Thr Glu Ala Pro Leu
                85                  90                  95

Ala Ser Phe Leu Trp Leu Asp Leu Val Asn Arg Asp Ile Thr Pro Tyr
            100                 105                 110

Pro Gly Val Leu Asp Arg Val His Tyr Asp Ala Met Ser Val Tyr Val
            115                 120                 125

Gly Arg Gly Val Gly Gly Gly Ser Leu Val Asn Gly Gly Met Ala Val
            130                 135                 140

Thr Pro Leu Arg Ser Tyr Phe Ala Glu Gln Phe Pro Thr Val Asp Ser
145                 150                 155                 160

Ala Glu Met Tyr Gly Thr Tyr Phe Pro Arg Ala Arg Ser Met Leu Gly
                165                 170                 175

Val Asn Ser Ile Asp Pro Ala Trp Phe Glu Ser Thr Glu Trp Tyr Gln
            180                 185                 190

Phe Thr Arg Thr Ser Arg Lys Ala Ala Asp Thr Gly Leu Lys Thr
            195                 200                 205

Thr Phe Val Pro Asn Val Tyr Asp Phe Gly His Met Gln Arg Glu Ala
210                 215                 220

Ala Gly Thr Ala Thr Lys Ser Ala Leu Gly Gln Glu Val Ile Tyr Gly
225                 230                 235                 240

Asn Asn Ser Gly Lys Arg Ser Leu Asp Lys Thr Tyr Leu Ala Ser Ala
                245                 250                 255

Leu Gly Thr Gly Asn Val Thr Ile His Thr Leu Glu Lys Val Arg Ala
```

```
                        260                 265                 270
Ile Ser Arg Ala Ala Asp Gly Thr Tyr Val Leu Thr Ala Asp Arg Ile
            275                 280                 285

Asp Leu Thr Gly Lys Val Val Glu Thr Lys Gln Tyr Gly Cys Thr Tyr
        290                 295                 300

Leu Phe Leu Gly Gly Ser Ile Gly Thr Thr Glu Leu Leu Val Arg
305                 310                 315                 320

Ala Arg Glu Thr Gly Thr Leu Pro Ala Leu Asn Ala Ser Val Gly Ser
                    325                 330                 335

Gly Trp Gly Thr Asn Gly Asn Val Met Leu Gly Arg Ala Asn His Val
                340                 345                 350

Trp Asp Thr Val Gly Ala Asn Gln Ser Thr Met Pro Val Met Gly Ile
            355                 360                 365

Asp Asp Trp Ala Asn Ala Ser Asn Pro Val Phe Ala Glu Ile Ala Pro
        370                 375                 380

Leu Pro Ile Gly Leu Glu His Trp Val Ser Leu Tyr Leu Ala Ile Thr
385                 390                 395                 400

Lys Asn Pro Gln Arg Ala Ser Phe Thr Tyr Asp Ser Gly Ser Asp Gly
                    405                 410                 415

Val Arg Leu Ser Trp Thr Ala Ala Gln Ser Ala Val Ser Val Asn Met
                420                 425                 430

Ala Lys Lys Leu Phe Asp Arg Ile Asn Ser Ala Asn Ser Thr Ile Tyr
            435                 440                 445

Arg Tyr Asp Leu Phe Gly Ser Ser Ser Lys Val Phe Ala Asp Asp Phe
        450                 455                 460

Cys Tyr His Pro Leu Gly Gly Cys Val Leu Gly Arg Ala Thr Asp Asp
465                 470                 475                 480

Tyr Gly Arg Val Lys Gly Tyr Ser Lys Leu Tyr Val Thr Asp Gly Ser
                    485                 490                 495

Leu Val Pro Gly Ser Ile Gly Val Asn Pro Phe Val Thr Ile Thr Ala
                500                 505                 510

Leu Ala Glu Arg Thr Met Ala Arg Val Leu Ala Glu Asp Thr Ala Pro
            515                 520                 525
```

<210> SEQ ID NO 52
<211> LENGTH: 526
<212> TYPE: PRT
<213> ORGANISM: Streptomyces prunicolor

<400> SEQUENCE: 52

```
Met Ile Ala Leu Gln Thr Ala Ala Thr Ala Gly Leu Thr Arg Ile Gly
1               5                   10                  15

Leu Gln Ser Ala Gln Ala Val Glu Pro Ala Ala Val Glu Thr Ala Pro
            20                  25                  30

Ala Ile Val Val Gly Ser Gly Tyr Gly Gly Ala Val Ala Ala Leu Arg
        35                  40                  45

Leu Gly Gln Ala Gly Ile Thr Thr Leu Val Leu Glu Met Gly Arg Leu
    50                  55                  60

Trp Asn Thr Pro Gly Thr Asp Gly Lys Ile Phe Cys Ser Thr Ala Ala
65                  70                  75                  80

Pro Asp Lys Arg Ser Met Trp Phe Lys Thr Arg Thr Glu Ala Pro Leu
                85                  90                  95

Ala Ser Phe Leu Trp Leu Asp Val Val Asn Lys Asp Ile Thr Ala Tyr
            100                 105                 110
```

-continued

```
Pro Gly Ala Leu Asp Arg Val His Tyr Asp Asn Met Ser Val Tyr Val
            115                 120                 125

Gly Arg Gly Val Gly Gly Ser Leu Val Asn Gly Gly Met Ala Val
130                 135                 140

Thr Pro Leu Gln Ser Tyr Phe Ala Glu Gln Phe Pro Thr Val Asp Ala
145                 150                 155                 160

Thr Ala Met Tyr Gly Thr Tyr Phe Pro Arg Ala Arg Thr Met Leu Gly
                165                 170                 175

Val Asn Thr Val Asp Pro Thr Trp Phe Glu Ser Thr Glu Trp Tyr Gln
            180                 185                 190

Phe Thr Arg Thr Ser Arg Lys Ala Ala Thr Asn Thr Gly Leu Lys Thr
        195                 200                 205

Thr Phe Val Pro Asn Val Tyr Asp Phe Gly Tyr Met Gln Gln Glu Ala
    210                 215                 220

Ala Gly Thr Ala Thr Lys Ser Ala Leu Ala Gln Glu Val Ile Tyr Gly
225                 230                 235                 240

Asn Asn Tyr Gly Lys Lys Ser Leu Asp Lys Thr Tyr Leu Ala Ser Ala
                245                 250                 255

Leu Gly Thr Gly Lys Val Thr Ile His Thr Met Glu Lys Val Lys Ala
            260                 265                 270

Val Thr Arg Ala Ser Asp Gly Ser Tyr Val Leu Thr Val Asp Arg Ile
        275                 280                 285

Asp Asp Thr Gly Thr Val Val Glu Thr Lys Gln Tyr Ser Cys Thr Tyr
    290                 295                 300

Leu Phe Leu Gly Gly Ser Leu Gly Thr Thr Glu Leu Leu Val Arg
305                 310                 315                 320

Ala Arg Glu Thr Gly Thr Leu Pro Ala Leu Asn Ser Ser Val Gly Ala
                325                 330                 335

Gly Trp Gly Pro Asn Gly Asn Thr Met Val Gly Arg Ala Asn His Ile
            340                 345                 350

Trp Asp Thr Thr Gly Ala Asn Gln Ser Thr Met Pro Val Met Gly Ile
        355                 360                 365

Asp Asp Trp Ala Asn Thr Asp Asn Pro Val Phe Ala Glu Ile Ala Pro
    370                 375                 380

Leu Pro Ile Gly Phe Glu Thr Trp Val Ser Leu Tyr Leu Ala Ile Thr
385                 390                 395                 400

Lys Asn Pro Gln Arg Ala Ser Phe Ala Tyr Asp Ser Ala Ser Gly Thr
                405                 410                 415

Val Lys Leu Gly Trp Thr Ala Ala Gln Ser Ala Val Ser Val Ala Met
            420                 425                 430

Ala Lys Lys Leu Phe Asp Arg Ile Asn Ser Ala Asn Ala Thr Leu Tyr
        435                 440                 445

Arg Tyr Asp Leu Phe Gly Ser Thr Ser Lys Val Phe Ala Asp Asp Phe
    450                 455                 460

Cys Tyr His Pro Leu Gly Gly Cys Val Leu Gly Ser Ala Thr Asp Asn
465                 470                 475                 480

Tyr Gly Arg Val Lys Gly Tyr Ser Lys Leu Tyr Val Thr Asp Gly Ser
                485                 490                 495

Leu Val Pro Gly Asn Ile Gly Val Asn Pro Phe Val Thr Ile Thr Ala
            500                 505                 510

Leu Ala Glu Arg Thr Leu Glu Arg Val Leu Ala Glu Asp Phe
        515                 520                 525
```

<210> SEQ ID NO 53
<211> LENGTH: 528
<212> TYPE: PRT
<213> ORGANISM: Streptomyces bottropensis

<400> SEQUENCE: 53

```
Met Ala Ala Leu Gln Thr Ala Thr Leu Gly Leu Thr Arg Ile Gly
1               5                   10                  15

Leu Gln Ser Ala Arg Ala Glu Pro Asp Ala Val Asp Asn Ala Pro
            20                  25                  30

Ala Ile Val Ile Gly Ser Gly Tyr Gly Ala Val Ala Ala Leu Arg
        35                  40                  45

Leu Gly Gln Ala Gly Ile Arg Thr Leu Val Leu Glu Met Gly Arg Ala
50                  55                  60

Trp Thr Thr Pro Gly Ala Asp Gly Lys Ile Phe Cys Ser Thr Arg Glu
65                  70                  75                  80

Pro Asp Glu Arg Ser Met Trp Phe Lys Thr Arg Thr Glu Ala Pro Leu
                85                  90                  95

Ala Thr Phe Leu Trp Leu Asp Val Val Asn Gln Asp Ile Ser Ser Tyr
            100                 105                 110

Pro Gly Val Leu Asp Arg Val Arg Tyr Ala Asn Met Ser Val Phe Leu
        115                 120                 125

Gly Arg Gly Val Gly Gly Gly Ser Leu Val Asn Gly Ser Met Ala Val
130                 135                 140

Thr Pro Leu Gln Ser Tyr Phe Ala Glu Gln Phe Pro Thr Val Asp Thr
145                 150                 155                 160

Ala Glu Met Tyr Ser Thr Tyr Phe Pro Arg Ala Arg Ser Met Leu Gly
                165                 170                 175

Val Asn Thr Ile Asp Pro Ala Trp Phe Glu Ser Thr Glu Trp Tyr Arg
            180                 185                 190

Phe Ser Arg Val Ser Arg Ala His Ala Glu Lys Ala Gly Leu Arg Thr
        195                 200                 205

Thr Phe Val Pro Ser Val Tyr Asp Phe Gly His Met Arg Arg Glu Ala
210                 215                 220

Ala Gly Thr Ala Pro Lys Ser Ala Leu Ala Gly Glu Val Ile Tyr Gly
225                 230                 235                 240

Asn Asn His Gly Lys Lys Ser Leu Asp Lys Thr Tyr Leu Ala Ala Ala
                245                 250                 255

Leu Gly Thr Gly Asn Val Thr Ile His Thr Met Glu Arg Ala Arg Gly
            260                 265                 270

Ile Arg Arg Leu Ser Asp Gly Thr Tyr Val Val Thr Val Asp Arg Ile
        275                 280                 285

Asp Asp Thr Gly Ala Val Val Glu Thr Lys Glu Tyr Gly Cys Thr Tyr
290                 295                 300

Leu Phe Leu Gly Ala Gly Ser Val Gly Thr Thr Glu Leu Leu Val Arg
305                 310                 315                 320

Ala Arg Ala Lys Gly Thr Leu Pro Ala Leu His Ala Ser Val Gly Ala
                325                 330                 335

Gly Trp Gly Ser Asn Gly Asn Val Met Leu Gly Arg Ala Asn His Leu
            340                 345                 350

Trp Asp Thr Val Gly Ala Asn Gln Ser Thr Met Pro Val Met Gly Ile
        355                 360                 365

Asp Asp Trp Ala Asn Thr Ala Asn Pro Val Phe Ala Glu Ile Ala Pro
370                 375                 380
```

-continued

Leu Pro Thr Gly Leu Glu His Trp Val Ser Leu Tyr Leu Ala Ile Thr
385                 390                 395                 400

Lys Asn Pro Glu Arg Ala Ser Phe Thr Tyr Asp Ala Ala Ser Asp Ser
            405                 410                 415

Ala Lys Leu Gly Trp Ser Ala Ala Gln Ser Ala Val Ser Ser Ser Met
            420                 425                 430

Ala Lys Lys Leu Phe Asp Arg Ile Asn Ser Ala Asn Ser Thr Met Tyr
            435                 440                 445

Arg Tyr Asp Leu Phe Gly Ser Ser Asn Lys Val Phe Ala Asp Asp Phe
450                 455                 460

Thr Tyr His Pro Leu Gly Gly Cys Val Leu Gly Arg Ala Thr Asp Asp
465                 470                 475                 480

Tyr Ala Arg Val Lys Gly Tyr Ser Lys Leu Tyr Ile Thr Asp Gly Ser
            485                 490                 495

Leu Val Pro Gly Ser Ile Gly Val Asn Pro Phe Val Thr Ile Thr Ala
            500                 505                 510

Leu Ala Glu Arg Thr Met Ala Arg Ile Leu Val Glu Asp Thr Ala Pro
            515                 520                 525

<210> SEQ ID NO 54
<211> LENGTH: 507
<212> TYPE: PRT
<213> ORGANISM: Brevibacterium sterolicum

<400> SEQUENCE: 54

Ala Pro Ser Arg Thr Leu Ala Asp Gly Asp Arg Val Pro Ala Leu Val
1               5                   10                  15

Ile Gly Ser Gly Tyr Gly Gly Ala Val Ala Ala Leu Arg Leu Thr Gln
                20                  25                  30

Ala Gly Ile Pro Thr Gln Ile Val Glu Met Gly Arg Ser Trp Asp Thr
            35                  40                  45

Pro Gly Ser Asp Gly Lys Ile Phe Cys Gly Met Leu Asn Pro Asp Lys
        50                  55                  60

Arg Ser Met Trp Leu Ala Asp Lys Thr Asp Gln Pro Val Ser Asn Phe
65                  70                  75                  80

Met Gly Phe Gly Ile Asn Lys Ser Ile Asp Arg Tyr Val Gly Val Leu
                85                  90                  95

Asp Ser Glu Arg Phe Ser Gly Ile Lys Val Tyr Gln Gly Arg Gly Val
            100                 105                 110

Gly Gly Gly Ser Leu Val Asn Gly Gly Met Ala Val Thr Pro Lys Arg
        115                 120                 125

Asn Tyr Phe Glu Glu Ile Leu Pro Ser Val Asp Ser Asn Glu Met Tyr
130                 135                 140

Asn Lys Tyr Phe Pro Arg Ala Asn Thr Gly Leu Gly Val Asn Asn Ile
145                 150                 155                 160

Asp Gln Ala Trp Phe Glu Ser Thr Glu Trp Tyr Lys Phe Ala Arg Thr
                165                 170                 175

Gly Arg Lys Thr Ala Gln Arg Ser Gly Phe Thr Thr Ala Phe Val Pro
            180                 185                 190

Asn Val Tyr Asp Phe Glu Tyr Met Lys Lys Glu Ala Ala Gly Gln Val
            195                 200                 205

Thr Lys Ser Gly Leu Gly Gly Glu Val Ile Tyr Gly Asn Asn Ala Gly
        210                 215                 220

Lys Lys Ser Leu Asp Lys Thr Tyr Leu Ala Gln Ala Ala Thr Gly
225                 230                 235                 240

```
Lys Leu Thr Ile Thr Thr Leu His Arg Val Thr Lys Val Ala Pro Ala
                245                 250                 255

Thr Gly Ser Gly Tyr Ser Val Thr Met Glu Gln Ile Asp Glu Gln Gly
            260                 265                 270

Asn Val Val Ala Thr Lys Val Val Thr Ala Asp Arg Val Phe Phe Ala
            275                 280                 285

Ala Gly Ser Val Gly Thr Ser Lys Leu Leu Val Ser Met Lys Ala Gln
            290                 295                 300

Gly His Leu Pro Asn Leu Ser Ser Gln Val Gly Glu Gly Trp Gly Asn
305                 310                 315                 320

Asn Gly Asn Ile Met Val Gly Arg Ala Asn His Met Trp Asp Ala Thr
                325                 330                 335

Gly Ser Lys Gln Ala Thr Ile Pro Thr Met Gly Ile Asp Asn Trp Ala
            340                 345                 350

Asp Pro Thr Ala Pro Ile Phe Ala Glu Ile Ala Pro Leu Pro Ala Gly
            355                 360                 365

Leu Glu Thr Tyr Val Ser Leu Tyr Leu Ala Ile Thr Lys Asn Pro Glu
            370                 375                 380

Arg Ala Arg Phe Gln Phe Asn Ser Gly Thr Gly Lys Val Asp Leu Thr
385                 390                 395                 400

Trp Ala Gln Ser Gln Asn Gln Lys Gly Ile Asp Met Ala Lys Lys Val
                405                 410                 415

Phe Asp Lys Ile Asn Gln Lys Glu Gly Thr Ile Tyr Arg Thr Asp Leu
            420                 425                 430

Phe Gly Val Tyr Tyr Lys Thr Trp Gly Asp Asp Phe Thr Tyr His Pro
            435                 440                 445

Leu Gly Gly Val Leu Leu Asn Lys Ala Thr Asp Asn Phe Gly Arg Leu
            450                 455                 460

Pro Glu Tyr Pro Gly Leu Tyr Val Asp Gly Ser Leu Val Pro Gly
465                 470                 475                 480

Asn Val Gly Val Asn Pro Phe Val Thr Ile Thr Ala Leu Ala Glu Arg
                485                 490                 495

Asn Met Asp Lys Ile Ile Ser Ser Asp Ile Gln
            500                 505

<210> SEQ ID NO 55
<211> LENGTH: 564
<212> TYPE: PRT
<213> ORGANISM: Nocardia sp.

<400> SEQUENCE: 55

Met Pro Asp Phe Asp Tyr Asp Val Val Ile Gly Ser Gly Phe Gly
1               5                   10                  15

Gly Ser Val Ser Ala Leu Arg Leu Thr Glu Lys Gly Tyr Arg Val Ala
            20                  25                  30

Val Leu Glu Ser Gly Arg Arg Trp Pro Ala Glu Ser Ile Pro Asn Ser
            35                  40                  45

Asn Trp Asn Val Arg Lys Ser Ile Trp Ala Pro Arg Leu Gly Leu Thr
        50                  55                  60

Gly Pro Gln Arg Ile Ser Val Leu Gly Lys Cys Ala Val Phe Ser Ala
65                  70                  75                  80

Ala Gly Val Gly Gly Gly Ser Leu Ile Tyr Gly Asn Thr Leu Tyr Glu
                85                  90                  95

Pro Leu Pro Asn Phe Tyr Thr Asp Lys Gln Trp Ala His Ile Ala Asp
```

```
                100             105                 110
Trp Arg Ser Glu Leu Ser Pro Tyr Tyr Asp Gln Ala Lys Arg Met Leu
            115                 120             125

Gly Val Ala Pro Asn Pro Arg Val Thr Pro Ala Asp Glu Val Ile Arg
            130                 135         140

Ser Ile Ala Asp Asp Leu Gly Val Gly Asp Thr Tyr His Pro Thr Asn
145             150                 155                     160

Val Gly Val Phe Phe Asn Glu Glu Gln Pro Gly Val Glu Val Asp Asp
                165                 170             175

Pro Tyr Phe Gly Gly Ala Gly Pro Arg Arg Ser Gly Cys Ile His Cys
            180                 185             190

Ala Arg Cys Phe Thr Gly Cys Pro His Asn Ala Lys Asn Thr Thr Pro
        195             200             205

Thr Asn Tyr Leu Tyr Leu Ala Glu Gln Ala Gly Ala Lys Val Phe Glu
        210             215             220

Leu Thr Thr Ala Thr Arg Val Arg Pro Met Val Gly Gly Tyr Ala
225             230                 235                 240

Ile Glu Thr Gln Arg Ser Asp Arg Trp Val Arg Lys Gly Arg Lys Thr
                245                 250             255

Phe Thr Ala Glu Gln Val Val Phe Ala Ala Ala Leu Gly Thr Gln
            260                 265             270

Lys Leu Leu His Lys Met Arg Asp Asp Lys Val Leu Pro Asn Leu Ser
            275                 280             285

Pro Arg Leu Gly Glu Leu Thr Arg Ser Asn Ser Glu Ala Ile Leu Asn
        290                 295             300

Val Val Ser Arg Gln Arg Ser Asp Phe Ala Glu Gly Ile Ala Ile Thr
305             310                 315                 320

Ser Ser Ile His Pro Glu Pro Asp Thr His Val Glu Val Cys His Tyr
                325                 330             335

Gly Lys Gly Gln Asn Ala Leu Phe Pro Met Ser Val Pro Ile Val Asp
            340                 345             350

Gly Gly Ala Phe Arg Phe Leu Arg Phe Leu Leu Ala Ile Val Leu His
            355                 360             365

Pro Leu Val Phe Ala Arg Ser Leu Asn Ala Arg His Ala Ser Glu Lys
        370                 375             380

Ser Val Ile Leu Leu Val Met Gln Ser Leu Asp Asn Ser Leu Thr Ser
385                 390                 395                 400

Phe Arg Arg Trp Gly Gln Leu Lys Thr Arg Gln Gly Thr Gly Gln Pro
                405                 410             415

Asn Pro Thr Trp Ile Pro Leu Ala His Glu Val Gly Arg Arg Phe Gly
            420                 425             430

Glu Lys Val Asp Gly Asp Val His Gly Leu Val Met Asp Val Phe Asn
            435                 440             445

Ile Pro Ala Thr Ala His Tyr Ile Gly Gly Cys Val Ile Gly Glu Gly
        450                 455             460

Pro Glu Ser Gly Val Val Asp Pro Tyr Gln Arg Val Phe Gly His Pro
465                 470                 475                 480

Gly Leu His Ile Ala Asp Gly Ser Ala Val Thr Ala Asn Leu Gly Val
                485                 490             495

Asn Pro Ser Leu Thr Ile Thr Ala Gln Ala Glu Arg Ala Met Ala Phe
            500                 505             510

Trp Pro Asn Lys Gly Glu Pro Asp Pro Arg Pro Glu Leu Gly Ala Gly
            515                 520             525
```

Tyr Arg Arg Ile Asp Pro Val Ala Pro His Tyr Ala Thr Val Pro Asp
            530                 535                 540

Thr Ala Pro Gly Ala Leu Arg Leu Pro Ile Thr Pro Ile Asp Pro Ala
545                 550                 555                 560

Pro Ala Glu Arg

<210> SEQ ID NO 56
<211> LENGTH: 582
<212> TYPE: PRT
<213> ORGANISM: Burkholderia cepacia

<400> SEQUENCE: 56

Met Ser Gln Asp Phe Arg Asp Glu Pro Ala Ser Arg Arg Ala Phe Leu
1               5                   10                  15

Ala Asp Met Ala Lys Leu Ala Ala Gly Val Val Thr Gly Trp Thr
            20                  25                  30

Pro Leu Tyr Gln Ile Ala Ala Asn Ala Arg Thr Ala Asp Ala Pro Pro
            35                  40                  45

Pro Gly Phe Pro Ala Asp Ile Pro Leu Tyr Lys Gln Ala Phe Gln Asn
    50                  55                  60

Trp Ser Gly Glu Ile Ala Val Gln Asp Val Trp Thr Ala Ala Pro Arg
65                  70                  75                  80

Ser Ala Asp Asp Val Ala Ala Val Asn Trp Ala Arg Ala Asn Gly
                85                  90                  95

Tyr Arg Ile Arg Pro Arg Gly Tyr Met His Asn Trp Ser Pro Leu Thr
            100                 105                 110

Leu Asp Pro Gly Ala Gly Ala Ala Asn Val Val Leu Leu Asp Thr Thr
            115                 120                 125

Lys Ser Leu Thr Ala Val Ser Val Asp Thr Ser Ala Arg Pro Ala Arg
130                 135                 140

Val Thr Ala Gln Thr Gly Ile Ser Leu Glu Ser Leu Leu Ala Thr Leu
145                 150                 155                 160

Glu Gln Tyr Gly Leu Gly Val Ile Ala Ala Pro Ala Pro Gly Asp Ile
                165                 170                 175

Thr Leu Gly Gly Ala Leu Ala Ile Asp Ala His Gly Thr Ala Val Pro
            180                 185                 190

Ala Val Gly Glu Thr Leu Gln Pro Gly His Thr Tyr Gly Ser Leu Ser
            195                 200                 205

Asn Leu Val Val Ala Leu Thr Ala Val Val Tyr Asp Pro Ala Arg Gln
    210                 215                 220

Gln Tyr Val Leu Arg Arg Phe Glu Arg Ser Asp Pro Glu Ile Gly Ala
225                 230                 235                 240

Phe Leu Ala His Ile Gly Arg Ala Phe Val Val Glu Val Thr Leu Thr
                245                 250                 255

Ala Gly Pro Asn Gln Arg Leu Arg Cys Gln Ser Tyr Val Asp Ile Pro
            260                 265                 270

Ala Ser Glu Leu Phe Ala Pro Ala Gly Thr Ser Gly Arg Thr Ile Thr
        275                 280                 285

Ser Phe Leu Asp Arg Ala Gly Val Glu Ala Ile Trp Phe Pro Phe
    290                 295                 300

Thr Ser Ser Pro Trp Leu Lys Val Trp Thr Pro Thr Pro Ser Lys Pro
305                 310                 315                 320

Phe Leu Ser Arg Ala Val Thr Gln Pro Tyr Asn Tyr Pro Phe Ser Asp
                325                 330                 335

```
Ser Ile Ser Gln Ser Ile Ser Asp Leu Val Lys Arg Ile Val Ile Gly
            340             345                 350

Gly Glu Gly Ala Leu Thr Pro Leu Phe Gly Gln Thr Gln Leu Ala Ile
        355             360             365

Thr Ala Ala Gly Leu Ala Leu Thr Leu Ser Gly Asp Ile Trp Gly Trp
    370             375             380

Ser Arg Thr Val Leu Gln Tyr Ile Arg Pro Thr Thr Leu Arg Val Thr
385             390             395                 400

Ala Asn Gly Tyr Ala Val Leu Ala Arg Arg Ala Asp Val Gln Arg Val
                405             410             415

Ile Ser Glu Phe Val Gln Phe Tyr Gln Asn Arg Val Asp Thr Tyr Lys
            420             425             430

Ala Arg Gly Glu Tyr Pro Met Asn Gly Pro Val Glu Ile Arg Ile Thr
        435             440             445

Gly Leu Asp Lys Pro Ala Asp Ala Gly Ala Gly Ala Ala Val Pro Ser
    450             455             460

Leu Ser Ala Leu Lys Pro Arg Pro Asp Arg Pro Glu Trp Asp Val Ala
465             470             475                 480

Val Trp Phe Asp Ile Leu Thr Leu Pro Gly Thr Pro Ser Ala Asp Arg
            485             490             495

Phe Tyr Arg Glu Ile Glu Gln Trp Met Leu Ala Asn Tyr Thr Gly Ser
            500             505             510

Tyr Ala Thr Leu Arg Pro Glu Trp Ser Lys Gly Trp Gly Tyr Thr Asp
        515             520             525

Thr Ala Ala Trp Gln Asp Asp Thr Met Leu Thr Thr Thr Ile Pro Asn
    530             535             540

Leu Gln Arg Glu Gly Gln Pro Ala Ser Ser Thr Trp Asp Thr Ala Arg
545             550             555                 560

Ala Thr Leu Glu Arg Tyr Asp Pro His Arg Ile Phe Arg Ser Pro Leu
            565             570             575

Leu Asp Arg Leu Met Pro
            580
```